(12) United States Patent
     Pajvani

(10) Patent No.: US 10,149,855 B2
(45) Date of Patent: Dec. 11, 2018

(54) GAMMA-SECRETASE INHIBITION REDUCE APOC3 LEVELS AND PLASMA TRIGLYCERIDES

(71) Applicant: Utpal Pajvani, Leonia, NJ (US)

(72) Inventor: Utpal Pajvani, Leonia, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 15/117,155

(22) PCT Filed: Feb. 4, 2015

(86) PCT No.: PCT/US2015/014481
§ 371 (c)(1),
(2) Date: Aug. 5, 2016

(87) PCT Pub. No.: WO2015/120065
PCT Pub. Date: Aug. 13, 2015

(65) Prior Publication Data
US 2016/0354382 A1    Dec. 8, 2016

Related U.S. Application Data

(60) Provisional application No. 62/032,324, filed on Aug. 1, 2014, provisional application No. 61/936,279, filed on Feb. 5, 2014.

(51) Int. Cl.
| | | |
|---|---|---|
| *C12N 15/113* | (2010.01) |
| *A61K 31/55* | (2006.01) |
| *A61K 45/06* | (2006.01) |
| *A61K 31/192* | (2006.01) |
| *A61K 31/7088* | (2006.01) |
| *A61K 31/4168* | (2006.01) |
| *A61K 31/5513* | (2006.01) |

(52) U.S. Cl.
CPC ............ *A61K 31/55* (2013.01); *A61K 31/192* (2013.01); *A61K 31/4168* (2013.01); *A61K 31/5513* (2013.01); *A61K 31/7088* (2013.01); *A61K 45/06* (2013.01); *C12N 15/1137* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2003/0092003 A1* | 5/2003 | Blatt ................. | C07H 19/10 435/6.16 |
| 2009/0203135 A1* | 8/2009 | Forst ................. | A61K 47/48092 435/375 |
| 2010/0120787 A1* | 5/2010 | Sutcliffe ............ | A61K 31/00 514/252.18 |

OTHER PUBLICATIONS

Burgess et al (Neurobiology of Disease 24 (2006) 114-127) (Year: 2006).*

* cited by examiner

*Primary Examiner* — Richard A Schnizer
(74) *Attorney, Agent, or Firm* — John P. White; Cooper & Dunham LLP

(57) ABSTRACT

A method of reducing a subject's plasma triglyceride level, comprising administering to a subject in need thereof a gamma-secretase inhibitor in an amount effective to reduce the subject's plasma triglyceride level.

19 Claims, 18 Drawing Sheets

Specification includes a Sequence Listing.

SEQUENCE LISTING

```
<160> NUMBER OF SEQ ID NOS: 59

<210> SEQ ID NO 1
<211> LENGTH: 709
<212> TYPE: PRT
<213> ORGANISM: Homo sapiens

<400> SEQUENCE: 1

Met Ala Thr Ala Gly Gly Gly Ser Gly Ala Asp Pro Gly Ser Arg Gly
1               5                   10                  15

Leu Leu Arg Leu Leu Ser Phe Cys Val Leu Leu Ala Gly Leu Cys Arg
                20                  25                  30

Gly Asn Ser Val Glu Arg Lys Ile Tyr Ile Pro Leu Asn Lys Thr Ala
            35                  40                  45

Pro Cys Val Arg Leu Leu Asn Ala Thr His Gln Ile Gly Cys Gln Ser
    50                  55                  60

Ser Ile Ser Gly Asp Thr Gly Val Ile Val Val Glu Lys Glu Glu
65                  70                  75                  80

Asp Leu Gln Trp Val Leu Thr Asp Gly Pro Asn Pro Tyr Met Val
                85                  90                  95

Leu Leu Glu Ser Lys His Phe Thr Arg Asp Leu Met Glu Lys Leu Lys
            100                 105                 110

Gly Arg Thr Ser Arg Ile Ala Gly Leu Ala Val Ser Leu Thr Lys Pro
        115                 120                 125

Ser Pro Ala Ser Gly Phe Ser Pro Ser Val Gln Cys Pro Asn Asp Gly
    130                 135                 140

Phe Gly Val Tyr Ser Asn Ser Tyr Gly Pro Glu Phe Ala His Cys Arg
145                 150                 155                 160

Glu Ile Gln Trp Asn Ser Leu Gly Asn Gly Leu Ala Tyr Glu Asp Phe
                165                 170                 175

Ser Phe Pro Ile Phe Leu Leu Glu Asp Glu Asn Glu Thr Lys Val Ile
            180                 185                 190

Lys Gln Cys Tyr Gln Asp His Asn Leu Ser Gln Asn Gly Ser Ala Pro
        195                 200                 205

Thr Phe Pro Leu Cys Ala Met Gln Leu Phe Ser His Met His Ala Val
    210                 215                 220
```

-continued

```
Ile Ser Thr Ala Thr Cys Met Arg Arg Ser Ser Ile Gln Ser Thr Phe
225                 230                 235                 240

Ser Ile Asn Pro Glu Ile Val Cys Asp Pro Leu Ser Asp Tyr Asn Val
            245                 250                 255

Trp Ser Met Leu Lys Pro Ile Asn Thr Thr Gly Thr Leu Lys Pro Asp
        260                 265                 270

Asp Arg Val Val Val Ala Ala Thr Arg Leu Asp Ser Arg Ser Phe Phe
    275                 280                 285

Trp Asn Val Ala Pro Gly Ala Glu Ser Ala Val Ala Ser Phe Val Thr
290                 295                 300

Gln Leu Ala Ala Ala Glu Ala Leu Gln Lys Ala Pro Asp Val Thr Thr
305                 310                 315                 320

Leu Pro Arg Asn Val Met Phe Val Phe Phe Gln Gly Glu Thr Phe Asp
                325                 330                 335

Tyr Ile Gly Ser Ser Arg Met Val Tyr Asp Met Glu Lys Gly Lys Phe
            340                 345                 350

Pro Val Gln Leu Glu Asn Val Asp Ser Phe Val Glu Leu Gly Gln Val
        355                 360                 365

Ala Leu Arg Thr Ser Leu Glu Leu Trp Met His Thr Asp Pro Val Ser
    370                 375                 380

Gln Lys Asn Glu Ser Val Arg Asn Gln Val Glu Asp Leu Leu Ala Thr
385                 390                 395                 400

Leu Glu Lys Ser Gly Ala Gly Val Pro Ala Val Ile Leu Arg Arg Pro
                405                 410                 415

Asn Gln Ser Gln Pro Leu Pro Pro Ser Ser Leu Gln Arg Phe Leu Arg
            420                 425                 430

Ala Arg Asn Ile Ser Gly Val Val Leu Ala Asp His Ser Gly Ala Phe
        435                 440                 445

His Asn Lys Tyr Tyr Gln Ser Ile Tyr Asp Thr Ala Glu Asn Ile Asn
    450                 455                 460

Val Ser Tyr Pro Glu Trp Leu Ser Pro Glu Glu Asp Leu Asn Phe Val
465                 470                 475                 480

Thr Asp Thr Ala Lys Ala Leu Ala Asp Val Ala Thr Val Leu Gly Arg
                485                 490                 495

Ala Leu Tyr Glu Leu Ala Gly Gly Thr Asn Phe Ser Asp Thr Val Gln
            500                 505                 510

Ala Asp Pro Gln Thr Val Thr Arg Leu Leu Tyr Gly Phe Leu Ile Lys
        515                 520                 525

Ala Asn Asn Ser Trp Phe Gln Ser Ile Leu Arg Gln Asp Leu Arg Ser
    530                 535                 540

Tyr Leu Gly Asp Gly Pro Leu Gln His Tyr Ile Ala Val Ser Ser Pro
545                 550                 555                 560

Thr Asn Thr Thr Tyr Val Val Gln Tyr Ala Leu Ala Asn Leu Thr Gly
                565                 570                 575

Thr Val Val Asn Leu Thr Arg Glu Gln Cys Gln Asp Pro Ser Lys Val
            580                 585                 590

Pro Ser Glu Asn Lys Asp Leu Tyr Glu Tyr Ser Trp Val Gln Gly Pro
        595                 600                 605

Leu His Ser Asn Glu Thr Asp Arg Leu Pro Arg Cys Val Arg Ser Thr
    610                 615                 620

Ala Arg Leu Ala Arg Ala Leu Ser Pro Ala Phe Glu Leu Ser Gln Trp
625                 630                 635                 640
```

```
Ser Ser Thr Glu Tyr Ser Thr Trp Thr Glu Ser Arg Trp Lys Asp Ile
                645                 650                 655

Arg Ala Arg Ile Phe Leu Ile Ala Ser Lys Glu Leu Glu Leu Ile Thr
            660                 665                 670

Leu Thr Val Gly Phe Gly Ile Leu Ile Phe Ser Leu Ile Val Thr Tyr
        675                 680                 685

Cys Ile Asn Ala Lys Ala Asp Val Leu Phe Ile Ala Pro Arg Glu Pro
    690                 695                 700

Gly Ala Val Ser Tyr
705

<210> SEQ ID NO 2
<211> LENGTH: 2949
<212> TYPE: DNA
<213> ORGANISM: Homo sapiens

<400> SEQUENCE: 2
tctgcagaat tcggcttgcg cctggaaaca cgaacttccg gtctcttagg ctccgggcca      60
cagagacggt gtcagtggta gcctagagag gccgctaaca gacaggagcc gaacggggc     120 ttccgctcag cagagaggca agatggctac ggcaggggt ggctctgggg ctgacccggg     180
aagtcggggt ctccttcgcc ttctgtcttt ctgcgtccta ctagcaggtt tgtgcagggg     240
aaactcagtg gagaggaaga tatatatccc cttaaataaa acagtccct gtgttcgcct      300 gctcaacgcc actcatcaga ttggctgcca gtcttcaatt agtggagaca caggggttat     360
ccacgtagta gagaaagagg aggacctaca gtgggtattg actgatggcc caaccccc       420 ttacatggtt ctgctggaga gcaagcattt taccagggat ttaatggaga gctgaaagg      480 gagaaccagc cgaattgctg gtcttgcagt gtccttgacc aagcccagtc ctgcctcagg     540
cttctctcct agtgtacagt gcccaaatga tgggtttggt gtttactcca attcctatgg     600
gccagagttt gctcactgca gagaaataca gtggaattcg ctgggcaatg gtttggctta     660
tgaagacttt agtttcccca tcttcttct tgaagatgaa aatgaaacca aagtcatcaa      720
gcagtgctat caagatcaca acctgagtca gaatggctca gcaccaacct tcccactatg     780
tgccatgcag ctcttttcac acatgcatgc tgtcatcagc actgccacct gcatgcggcg     840
cagctccatc caaagcacct tcagcatcaa cccagaaatc gtctgtgacc ccctgtctga     900
ttacaatgtg tggagcatgc taaagcctat aaatacaact gggacattaa agcctgacga     960
cagggttgtg gttgctgcca cccggctgga tagtcgttcc ttttctgga atgtggcccc    1020 aggggctgaa agcgcagtgg cttcctttgt cacccagctg ctgctgctg aagctttgca    1080 aaaggcacct gatgtgacca ccctgccccg caatgtcatg tttgtcttct ttcaagggga    1140
aacttttgac tacattggca gctcgaggat ggtctacgat atggagaagg gcaagttcc     1200 cgtgcagtta gagaatgttg actcattttgt ggagctggga caggtggcct taagaacttc    1260
attagagctt tggatgcaca cagatcctgt ttctcagaaa aatgagtctg tacgaaccaa    1320
ggtggaggat ctcctggcca cattggagaa gagtggtgct ggtgtccctg ctgtcatcct    1380
caggaggcca aatcagtccc agcctctccc accatcttcc ctgcagcgat ttcttcgagc    1440
tcgaaacatc tctggcgttg ttctggctga ccactctggt gccttccata acaaatatta    1500
ccagagtatt tacgacactg ctgagaacat taatgtgagc tatcccgaat ggctgagccc    1560
tgaagaggac ctgaactttg taacagacac tgccaaggcc ctggcagatg tggcacggt    1620 gctgggacgt gctctgtatg agcttgcagg aggaaccaac ttcagcgaca cagttcaggc    1680
```

| | |
|---|---|
| tgatccccaa acggttaccc gcctgctcta tgggttcctg attaaagcca acaactcatg | 1740 |
| gttccagtct atcctcaggc aggacctaag gtcctacttg ggtgacgggc ctcttcaaca | 1800 |
| ttacatcgct gtctccagcc ccaccaacac cacttatgtt gtacagtatg ccttggcaaa | 1860 |
| tttgactggc acagtggtca acctcacccg agagcagtgc caggatccaa gtaaagtccc | 1920 |
| aagtgaaaac aaggatctgt atgagtactc atgggtccag ggccctttgc attctaatga | 1980 |
| gacggaccga ctcccccggt gtgtgcgttc tactgcacga ttagccaggg ccttgtctcc | 2040 |
| tgcctttgaa ctgagtcagt ggagctctac tgaatactct acatggactg agagccgctg | 2100 |
| gaaagatatc cgtgcccgga tatttctcat cgccagcaaa gagcttgagt tgatcaccct | 2160 |
| gacagtgggc ttcggcatcc tcatcttctc cctcatcgtc acctactgca tcaatgccaa | 2220 |
| agctgatgtc cttttcattg ctccccggga gccaggagct gtgtcatact gagsaggacc | 2280 |
| scagcttttc ttgccagctc agcagttcac ttcctagagc atctgtccca ctgggacaca | 2340 |
| accactaatt tgtcactgga acctccctgg gcctgtctca gattgggatt aacataaaag | 2400 |
| agtggaacta tccaaaagag acaggagaa ataaataaat tgcctccctt cctccgctcc | 2460 |
| cctttcccat cacccttcc ccatttcctc ttccttctct actcatgcca gattttggga | 2520 |
| ttacaaatag aagcttcttg ctcctgttta actcccctagt tacccaccct aatttgccct | 2580 |
| tcaggaccct tctacttttt ccttcctgcc ctgtacctct ctctgctcct cacccccacc | 2640 |
| cctgtaccca gccaccttcc tgactgggaa ggacataaaa ggtttaatgt cagggtcaaa | 2700 |
| ctacattgag cccctgagga caggggcatc tctgggctga gcctactgtc tccttcccac | 2760 |
| tgtcctttct ccaggccctc agatggcaca ttagggtggg cgtgctgcgg gtgggtatcc | 2820 |
| cacctccagc ccacagtgct cagttgtact ttttattaag ctgtaatatc tattttgtt | 2880 |
| tttgtctttt tcctttattc ttttttgtaaa tatatatata atgagtttca ttaaaataga | 2940 |
| ttatcccac | 2949 |

```
<210> SEQ ID NO 3
<211> LENGTH: 1912
<212> TYPE: DNA
<213> ORGANISM: Homo sapiens

<400> SEQUENCE: 3
```

| | |
|---|---|
| ttactccaat tcctatgggc cagagtttgc tcactgcaga gaaatacagt ggaattcgct | 60 |
| gggcaatggt ttggcttatg aagactttag tttccccatc tttcttcttg aagatgaaaa | 120 |
| tgaaaccaaa gtcatcaagc agaaatcgtc tgtgaccccc tgtctgatta caatgtgtgg | 180 |
| agcatgctaa agcctataaa tacaactggg acattaaagc ctgacgacag ggttgtggtt | 240 |
| gctgccaccc ggctggatag tcgttccttt tctggaatg tggccccagg ggctgaaagc | 300 |
| gcagtggctt cctttgtcac ccagctggct gctgctgaag ctttgcaaaa ggcacctgat | 360 |
| gtgaccaccc tgccccgcaa tgtcatgttt gtcttctttc aagggaaac ttttgactac | 420 |
| attggcagct cgaggatggt ctacgatatg agaaagggca gtttcccgt gcagttagag | 480 |
| aatgttgact catttgtgga gctgggacag gtggccttaa gaacttcatt agagctttgg | 540 |
| atgcacacag atcctgtttc tcagaaaaat gagtctgtac ggaaccaggt ggaggatctc | 600 |
| ctggccacat ggagaagag tggtgctggt gtccctgctg tcatcctcag gaggccaaat | 660 |
| cagtcccagc ctctcccacc atcttccctg cagcgatttc ttcgagctcg aaacatctct | 720 |
| ggcgttgttc tggctgacca ctctggtgcc ttcataacaa aatattacca gagtatttac | 780 |
| gacactgctg agaacattaa tgtgagctat cccgaatggc tgagccctga agaggacctg | 840 |

```
aactttgtaa cagacactgc caaggccctg gcagatgtgg ccacggtgct gggacgtgct    900
ctgtatgagc ttgcaggagg aaccaacttc agcgacacag ttcaggctga tccccaaacg    960
gttacccgcc tgctctatgg gttcctgatt aaagccaaca actcatggtt ccagtctatc   1020
ctcaggcagg acctaaggtc ctacttgggt gacgggcctc ttcaacatta catcgctgtc   1080
tccagcccca ccaacaccac ttatgttgta cagtatgcct tggcaaattt gactggcaca   1140
gtggtcaacc tcacccgaga gcagtgccag gatccaagta aagtcccaag tgaaaacaag   1200
gatctgtatg agtactcatg ggtccagggc cctttgcatt ctaatgagac ggaccgactc   1260
ccccggtgtg tgcgttctac tgcacgatta gccagggcct gtctcctgc ctttgaactg    1320 agtcagtgga gctctactga atactctaca tggactgaga gccgctggaa agatatccgt   1380
gcccggatat ttctcatcgc cagcaaagag cttgagttga tcaccctgac agtgggcttc   1440
ggcatcctca tcttctccct catcgtcacc tactgcatca atgccaaagc tgatgtcctt   1500
ttcattgttc cccgggagcc aggagctgtg tcatactgag gaggaccccca gcttttcttg   1560 ccagctcagc agttcacttc ctagagcatc tgtcccactg gacacaacc actaatttgt    1620 cactggaacc tccctgggcc tgtctcagat tgggattaac ataaaagagt ggaactatcc   1680
aaaagagaca gggagaaata ataaaattgc ctcccttcct ccgctcccct ttcccatcac   1740
cccttcccca tttcctcttc cttctctact catgccagat tttgggatta caaatagaag   1800
cttcttgctc ctgtttaact ccctagttac ccaccctaat ttgcccttca ggaccttct    1860 acttttcct tcctgccctg tacctctctc tgctcctcac ccccacccct gt             1912
```

<210> SEQ ID NO 4
<211> LENGTH: 1979
<212> TYPE: DNA
<213> ORGANISM: Homo sapiens

<400> SEQUENCE: 4

```
agagaggcaa gatggctacg gcaggggtg gctctggggc tgacccggga agtcggggtc      60
tccttcgcct tctgtctttc tgcgtcctac tagcaggttt gtgcagggga aactcagtgg    120
agaggaagat atatatccccc ttaaataaaa cagctccctg tgttcgcctg ctcaacgcca   180
ctcatcagat tggctgccag tcttcaatta gtggagacac aggggttatc cacgtagtag   240
agaaagagga ggacctacag tgggtattga ctgatggccc caaccccccct tacatggttc   300 tgctggagag caagcatttt accagggatt taatggagaa gctgaaaggg agaaccagcc   360
gaattgctgt tcttgcagtg tccttgacca agcccagtcc tgcctcaggc ttctctccta   420
gtgtacagtg cccaaatgat gggtttggtg tttactccaa ttcctatggg ccagagtttg   480
ctcactgcag agaaatacag tggaattcgc tgggcaatgg tttggcttat gaagacttta   540
gtttccccat ctttcttctt gaagatgaaa atgaaaccaa agtcatcaag caggaaactt   600
ttgactacat tggcagctcg aggatggtct acgatatgga gaagggcaag tttcccgtgc   660
agttagagaa tgttgactca tttgtggagc tgggacaggt ggccttaaga acttcattag   720
agcttttgat gcacacagat cctgtttctc agaaaaatga gtctgtacgg aaccaggtgg   780
aggatctcct ggccacattg gagaagagtg gtgctggtgt ccctgctgtc atcctcagga   840
ggccaaatca gtcccagcct ctcccaccat cttccctgca gcgatttctt cgagctcgaa   900
acatctctgg cgttgttctg gctgaccacc ctggtgcctt ccataacaaa tattaccaga   960
gtatttacga cactgctgag aacattaatg tgagctatcc cgaatggctg agccctgaag   1020
```

| | |
|---|---|
| aggacctgaa ctttgtaaca gacactgcca aggccctggc agatgtggcc acggtgctgg | 1080 |
| gacgtgctct gtatgagctt gcaggaggaa ccaacttcag cgacacagtt caggctgatc | 1140 |
| cccaaacggt tacccgcctg ctctatgggt tcctgattaa agccaacaac tcatggttcc | 1200 |
| agtctatcct caggcaggac ctaaggtcct acttgggtga cgggcctctt caacattaca | 1260 |
| tcgctgtctc cagccccacc aacaccactt atgttgtaca gtatgccttg caaatttga | 1320 |
| ctggcacagt ggtcaacctc acccgagagc agtgccagga tccaagtaaa gtcccaagtg | 1380 |
| aaaacaagga tctgtatgag tactcatggg tccagggccc tttgcattct aatgagacgg | 1440 |
| accgactccc ccgtgtgtg cgttctactg cacgattagc cagggccttg tctcctgcct | 1500 |
| ttgaactgag ccagtggagc tctactgaat actctacatg gactgagagc cgctggaaag | 1560 |
| atatccgtgc ccggatattt ctcatcgcca gcaaagagct tgagttgatc accctgacag | 1620 |
| tgggcttcgg catcctcatc ttctccctca tcgtcaccta ctgcatcaat gccaaagctg | 1680 |
| atgtccttt cattgctccc cgggagccag gagctgtgtc atactgagga ggaccccagc | 1740 |
| ttttcttgcc agctcagcag ttcacttcct agagcatctg tcccactggg acacaaccac | 1800 |
| taatttgtca ctggaacctc cctgggcctg tctcagattg ggattaacat aaaagagtgg | 1860 |
| aactatccaa aagagacagg gagaaataaa taaattgcct cccttcctcc gctccccttt | 1920 |
| cccatcaccc cttccccatt tcctcttcct tctctactca tgccagattt tgggattac | 1979 |

```
<210> SEQ ID NO 5
<211> LENGTH: 580
<212> TYPE: DNA
<213> ORGANISM: Homo sapiens

<400> SEQUENCE: 5
```

| | |
|---|---|
| cgctcagcag agaggcaaga tggctacggc aggggggtggc tctggggctg acccgggaag | 60 |
| tcggggtctc cttcgccttc tgtctttctg cgtcctacta gcaggcctct tcctggactt | 120 |
| cgagcctgac cctctcccac tttgtccaga tgtctcgttt ttcccacaac cccagccacc | 180 |
| caccccacag tcgaaaggaa caggtgtgaa agttagcttt cttcctcgcg tttagacttt | 240 |
| ttgagacgaa agcaatcttg ttctgtgggt gctgtgcggc gcttaaaagg tttgtgcagg | 300 |
| ggaaactcag tggagaggaa gatatatatc cccttaaata aaacagctcc ctgtgttcgc | 360 |
| ctgctcaacg ccactcatca gattggctgc cagtcttcaa ttagtggaga cacgggggtt | 420 |
| atccacgtag tagagaaaga ggaggaccta cagtgggtat tgactgatgg ccccaacccc | 480 |
| ccttacatgg ttctgctgga gagcaagcat tttaccaggg atttaatgga gaagctgaaa | 540 |
| gggagaacca gccgaattgc tggtcttgca gtgtccttga | 580 |

```
<210> SEQ ID NO 6
<211> LENGTH: 2161
<212> TYPE: DNA
<213> ORGANISM: Homo sapiens

<400> SEQUENCE: 6
```

| | |
|---|---|
| aacgggggct tccgctcagc agagaggcaa gatggctacg gcaggggggtg ctctgggggc | 60 |
| tgacccggga agtcggggtc tccttcgcct tctgtctttc tgcgtcctac tagcaggttt | 120 |
| gtgcagggga aactcagtgg agaggaagat atatatcccc ttaaataaaa cagctccctg | 180 |
| tgttcgcctg ctcaacgcca ctcatcagat tggctgccag tcttcaatta gtggagacac | 240 |
| agggggttatc cacgtagtag agaaagagga ggacctacag tgggtattga ctgatggccc | 300 |
| caaccccct tacatggttc tgctggagag caagcatttt accagggatt taatggagaa | 360 |

```
gctgaaaggg agaaccagcc gaattgctgg tcttgcagtg tccttgacca agcccagtcc    420
tgcctcaggc ttctctccta gtgtacagtg cccaaatgat gggtttggtg tttactccaa    480
ttcctatggg ccagagtttg ctcactgcag agaaatacag tggaattcgc tgggcaatgg    540
tttggcttat gaagacttta gtttccccat cttccttctt gaagatgaaa atgaaaccaa    600
agtcatcaag cagtgctatc aagatcacaa cctgagtcag aatggctcag caccaacctt    660
cccactatgc gccatgcagc tcttttcaca catgcatgct gtcatcagca ctgccacctg    720
catgcggcgc agctccatcc aaagcacctt cagcatcaac ccagaaatcg tctgtgaccc    780
cctgtctgat tacaatgtgt ggagcatgct aaagcctata aatacaactg gacattaaa     840 gcctgacgac agggttgtgg ttgctgccac ccggctggat agtcgttcct ttttctggaa    900
tgtggcccca ggggctgaaa gcgcagtggc ttcctttgtc acccagctgg ctgctgctga    960
agctttgcaa aaggcacctg atgtgaccac cctgccccgc aatgtcatgt ttgtcttctt   1020
tcaaggggaa acttttgact acattggcag ctcgaggatg gtctacgata tggagaaggg   1080
caagtttccc gtgcagttag agaatgttga ctcatttgtg gagctgggac aggtggcctt   1140
aagaacttca ttagagcttt ggatgcacac agatcctgtt tctcagaaaa atgagtctgt   1200
acggaaccag gtggaggatc tcctggccac attggagaag agtggtgctg tgtccctgc    1260 tgtcatcctc aggaggccaa atcagtccca gcctctccca ccatcttccc tgcagcgatt   1320
tcttcgagct cgaaacatct ctggcgttgt tctggctgac cactctggtg ccttccataa   1380
caaatattac cagagtattt acgacactgc tgagaacatt aatgtgagct atcccgaatg   1440
gctgagccct gaagaggacc tgaactttgt aacagacact gccaaggccc tggcagatgt   1500
ggccacggtg ctgggacgtg ctctgtatga gcttgcagga ggaaccaact tcagcgacac   1560
agttcaggct gatccccaaa cggttacccg cctgctctat gggttcctga ttaaagccaa   1620
caactcatgg ttccagtcta tcctcaggca ggacctaagg tcctacttgg gtgacgggcc   1680
tcttcaacat tacatcgctg tctccagccc caccaacacc acttatgttg tacagtatgc   1740
cttggcgaat ttgactggca cagtggtcaa cctcacccga gagcagtgcc aggatccaag   1800
taaagtccca agtgaaaaca aggatctgta tgagtactca tgggtccagg gccctttgca   1860
ttctaatgag acggaccgac tcccccggtg tgtgcgttct actgcacgat tagccagggc   1920
cttgtctcct gcctttgaac tgagtcagtg gagctctact gaatactcta catggactga   1980
gagccgctgg aaagatatcc gtgcccggat atttctcatc gccagcaaag agcttgagtt   2040
gatcaccctg acagtgggct tcggcatcct catcttctcc ctcatcgtca cctactgcat   2100
caatgccaaa gctgatgtcc ttttcattgc tccccgggag ccaggagctg tgtcatactg   2160
a                                                                   2161
```

<210> SEQ ID NO 7
<211> LENGTH: 2806
<212> TYPE: DNA
<213> ORGANISM: Homo sapiens
<220> FEATURE:
<221> NAME/KEY: misc_feature
<222> LOCATION: (2157)..(2157)
<223> OTHER INFORMATION: n is a, c, g, or t

<400> SEQUENCE: 7

```
gatggctacg gcaggggtg gctctggggc tgacccggga agtcgggtc tccttcgcct       60 tctgtctttc tgcgtcctac tagcaggttt gtgcagggga aactcagtgg agaggaagat    120
```

```
atatatcccc ttaaataaaa cagctccctg tgttcgcctg ctcaacgcca ctcatcagat      180
tggctgccag tcttcaatta gtggagacac aggggttatc cacgtagtag agaaagagga      240
ggacctacag tgggtattga ctgatggccc aaccccccct tacatggttc tgctggagag      300
caagcatttt accagggatt taatggaaa gctgaaaggg agaaccagcc gaattgctgg       360
tcttgcagtg tccttgacca agcccagtcc tgcctcaggc ttctctccta gtgtacagtg      420
cccaaatgat gggtttggtg tttactccaa ttcctatggg ccagagtttg ctcactgcag      480
agaaatacag tggaattcgc tgggcaatgg tttggcttat gaagacttta gtttccccat      540
ctttcttctt gaagatgaaa atgaaaccaa agtcatcaag cagtgctatc aagatcacaa      600
cctgagtcag aatggctcag caccaacctt cccactatgt gccatgcagc tcttttcaca      660
catgcatgct gtcatcagca ctgccacctg catgcggcgc agctccatcc aaagcacctt      720
cagcatcaac ccagaaatcg tctgtgaccc cctgtctgat acaatgtgt ggagcatgct      780
aaagcctata aatacaactg gacattaaa gcctgacgac agggttgtgg ttgctgccac       840
ccggctggat agtcgttcct ttttctggaa tgtggcccca ggggctgaaa gcgcagtggc      900
ttcctttgtc acccagctgg ctgctgctga agctttgcaa aaggcacctg atgtgaccac      960
cctgccccgc aatgtcatgt ttgtcttctt tcaaggggaa acttttgact acattggcag     1020
ctcgaggatg gtctacgata tggagaaggg caagtttccc gtgcagttag agaatgttga     1080
ctcatttgtg gagctgggac aggtggcctt aagaacttca ttagagcttt ggatgcacac     1140
agatcctgtt tctcagaaaa atgagtctgt acggaaccag gtggaggatc cctggccac     1200
attggagaag agtggtgctg gtgtccctgc tgtcatcctc aggaggccaa atcagtccca     1260
gcctctccca ccatcttccc tgcagcgatt tcttcgagct cgaaacatct ctggcgttgt     1320
tctggctgac cactctggtg ccttccataa caaatattac cagagtattt acgacactgc     1380
tgagaacatt aatgtgagct atcccgaatg gctgagccct gaagaggacc tgaactttgt     1440
aacagacact gccaaggccc tggcagatgt ggccacggtg ctgggacgtg ctctgtatga     1500
gcttgcagga ggaaccaact tcagcgacac agttcaggct gatccccaaa cggttacccg     1560
cctgctctat gggttcctga ttaaagccaa caactcatgg ttccagtcta tcctcaggca     1620
ggacctaagg tcctacttgg gtgacgggcc tcttcaacat tacatcgctg tctccagccc     1680
caccaacacc acttatgttg tacagtatgc cttggcaaat ttgactggca cagtggtcaa     1740
cctcacccga gagcagtgcc aggatccaag taaagtccca agtgaaaaca aggatctgta     1800
tgagtactca tgggtccagg gcccctttgca ttctaatgag acggaccgac tccccggtg     1860
tgtgcgttct actgcacgat tagccagggc cttgtctcct gcctttgaac tgagtcagtg     1920
gagctctact gaatactcta catggactga gagccgctgg aaagatatcc gtgcccggat     1980
atttctcatc gccagcaaag agcttgagtt gatcaccctg acagtgggct tcggcatcct     2040
catcttctcc ctcatcgtca cctactgcat caatgccaaa gctgatgtcc ttttcattgc     2100
tccccgggag ccaggagctg tgtcatactg aggaggaccc cagcttttct tgccagntca     2160
gcagttcact tcctagagca tctgtcccac tgggacacaa ccactaattt gtcactggaa     2220
cctccctggg cctgtctcag attgggatta acataaaaga gtggaactat ccaaaagaga     2280
cagggagaaa taaataaatt gcctcccttc ctccgctccc ctttcccatc accccttccc     2340
catttcctct tccttctcta ctcatgccag attttgggat tacaaataga agcttcttgc     2400
tcctgtttaa ctccctagtt acccacccta atttgccctt caggacccct ctactttttc     2460
cttcctgccc tgtacctctc tctgctcctc accccacccc ctgtacccag ccaccttcct     2520
```

-continued

| | | | | |
|---|---|---|---|---|
| gactgggaag | gacataaaag | gtttaatgtc | agggtcaaac | tacattgagc ccctgaggac | 2580 |
| aggggcatct | ctgggctgag | cctactgtct | ccttcccact | gtcctttctc caggccctca | 2640 |
| gatggcacat | tagggtgggc | gtgctgcggg | tgggtatccc | acctccagcc cacagtgctc | 2700 |
| agttgtactt | tttattaagc | tgtaatatct | attttttgttt | ttgtcttttt cctttattct | 2760 |
| ttttgtaaat | atatatataa | tgagtttcat | taaaatagat | tatccc | 2806 |

<210> SEQ ID NO 8
<211> LENGTH: 3041
<212> TYPE: DNA
<213> ORGANISM: Homo sapiens

<400> SEQUENCE: 8

| | | | | |
|---|---|---|---|---|
| agagacggtg | tcagtggtag | cctagagagg | ccgctaacag | acaggagccg aacgggggct | 60 |
| tccgctcagc | agagaggcaa | gatggctacg | gcagggggtg | gctctgggc tgacccggga | 120 |
| agtcggggtc | tccttcgcct | tctgtctttc | tgcgtcctac | tagcagtgtc actgtcaatg | 180 |
| gcgctacatg | gactttgtaa | taacccttg | aggcacatag | ctgggtgcca tgtagaacat | 240 |
| gtatctgtta | cgataagtgt | gtgcccaaga | aatcagaaga | atggacttta atctcatttt | 300 |
| agaaagtttg | tgcaggggaa | actcagtgga | gaggaagata | tatatcccct taaataaaac | 360 |
| agctccctgt | gttcgcctgc | tcaacgccac | tcatcagatt | ggctgccagt cttcaattag | 420 |
| tggagacaca | ggggttatcc | acgtagtaga | gaaagaggag | gacctacagt gggtattgac | 480 |
| tgatggcccc | aaccccccctt | acatggttct | gctggagagc | aagcatttta ccagggattt | 540 |
| aatggagaag | ctgaaaggga | gaaccagccg | aattgctggt | cttgcagtgt ccttgaccaa | 600 |
| gcccagtcct | gcctcaggct | tctctcctag | tgtacagtgc | ccaaatgatg ggtttggtgt | 660 |
| ttactccaat | tcctatgggc | cagagtttgc | tcactgcaga | gaaatacagt ggaattcgct | 720 |
| gggcaatggt | ttggcttatg | aagactttag | ttttccccatc | tttcttcttg aagatgaaaa | 780 |
| tgaaaccaaa | gtcatcaagc | agtgctatca | agatcacaaac | ctgagtcaga atggctcagc | 840 |
| accaaccttc | ccactatgtg | ccatgcagct | cttttcacac | atgcatgctg tcatcagcac | 900 |
| tgccacctgc | atgcggcgca | gctccatcca | aagcaccttc | agcatcaacc cagaaatcgt | 960 |
| ctgtgacccc | ctgtctgatt | acaatgtgtg | gagcatgcta | aagcctataa atacaactgg | 1020 |
| gacattaaag | cctgacgaca | gggttgtggt | tgctgccacc | cggctggata gtcgttcctt | 1080 |
| tttctggaat | gtggcccag | gggctgaaag | cgcagtggct | tcctttgtca cccagctggc | 1140 |
| tgctgctgaa | gctttgcaaa | aggcacctga | tgtgaccacc | ctgccccgca atgtcatgtt | 1200 |
| tgtcttcttt | caaggggaaa | cttttgacta | cattggcagc | tcgaggatgg tctacgatat | 1260 |
| ggagaagggc | aagtttcccg | tgcagttaga | gaatgttgac | tcatttgtgg agctgggaca | 1320 |
| ggtggcctta | gaacttcat | tagagctttg | gatgcacaca | gatcctgttt ctcagaaaaa | 1380 |
| tgagtctgta | cggaaccagg | tggaggatct | cctggcacca | ttggagaaga gtggtgctgg | 1440 |
| tgtccctgct | gtcatcctca | ggaggccaaa | tcagtcccag | cctctcccac catcttccct | 1500 |
| gcagcgattt | cttcgagctc | gaaacatctc | tggcgttgtt | ctggctgacc actctggtgc | 1560 |
| cttccataac | aaatattacc | agagtattta | cgacactgct | gagaacatta atgtgagcta | 1620 |
| tcccgaatgg | ctgagccctg | aagaggacct | gaactttgta | acagacactg ccaaggccct | 1680 |
| ggcagatgtg | gccacggtgc | tgggacgtgc | tctgtatgag | cttgcaggag gaaccaactt | 1740 |
| cagcgacaca | gttcaggctg | atccccaaac | ggttacccgc | ctgctctatg ggttcctgat | 1800 |

| | |
|---|---|
| taaagccaac aactcatggt tccagtctat cctcaggcag gacctaaggt cctacttggg | 1860 |
| tgacgggcct cttcaacatt acatcgctgt ctccagcccc accaacacca cttatgttgt | 1920 |
| acagtatgcc ttggcaaatt tgactggcac agtggtcaac ctcacccgag agcagtgcca | 1980 |
| ggatccaagt aaagtcccaa gtgaaaacaa ggatctgtat gagtactcat gggtccaggg | 2040 |
| cccctttgcat tctaatgaga cggaccgact ccccggtgt gtgcgttcta ctgcacgatt | 2100 |
| agccagggcc ttgtctcctg cctttgaact gagtcagtgg agctctactg aatactctac | 2160 |
| atggactgag agccgctgga aagatatcca tgcccggata tttctcatcg ccagcaaaga | 2220 |
| gcttgagttg atcaccctga cagtgggctt cggcatcctc atcttctccc tcatcgtcac | 2280 |
| ctactgcatc aatgccaaag ctgatgtcct tttcattgct ccccgggagc caggagctgt | 2340 |
| gtcatactga ggaggacccc agcttttctt gccagctcag cagttcactt cctagagcat | 2400 |
| ctgtcccact gggacacaac cactaatttg tcactggaac ctccctgggc ctgtctcaga | 2460 |
| ttgggattaa cataaaagag tggaactatc caaagagac agggagaaat aaataaattg | 2520 |
| cctcccttcc tccgctcccc tttcccatca cccccttccc atttcctctt ccttctctac | 2580 |
| tcatgccaga ttttgggatt acaaatagaa gcttcttgct cctgtttaac tccctagtta | 2640 |
| cccacccctaa tttgcccttc aggacccttc tactttttcc ttcctgccct gtacctctct | 2700 |
| ctgctcctca cccccacccc tgtacccagc caccttcctg actgggaagg acataaaagg | 2760 |
| tttaatgtca gggtcaaact acattgagcc cctgaggaca ggggcatctc tgggctgagc | 2820 |
| ctactgtctc cttcccactg tccttctcc aggccctcag atggcacatt agggtgggcg | 2880 |
| tgctgcgggt gggtatccca cctccagccc acagtgctca gttgtacttt ttattaagct | 2940 |
| gtaatatcta tttttgtttt tgtctttttc ctttattctt tttgtaaata tatatataat | 3000 |
| gagtttcatt aaaatagatt atcccaaaaa aaaaaaaaaa a | 3041 |

<210> SEQ ID NO 9
<211> LENGTH: 2821
<212> TYPE: DNA
<213> ORGANISM: Homo sapiens

<400> SEQUENCE: 9

| | |
|---|---|
| tggctacggc aggggtggc tctgggctg acccgggaag tcggggtctc cttcgccttc | 60 |
| tgtcttctg cgtcctacta gcaggtttgt gcagggaaa ctcagtggag aggaagatat | 120 |
| atatccccctt aaataaaaca gctccctgtg ttcgcctgct caacgccact catcagattg | 180 |
| gctgccagtc ttcaattagt ggagacacag gggttatcca cgtagtagag aaagaggagg | 240 |
| acctacagtg ggtattgact gatggcccca acccccctta catggttctg ctggagagca | 300 |
| agcattttac cagggattta atggagaagc tgaaagggag aaccagccga attgctggtc | 360 |
| ttgcagtgtc cttgaccaag cccagtcctg cctcaggctt ctctcctagt gtacagtgcc | 420 |
| caaatgatgg gtttggtgtt tactccaatt cctatgggcc agagtttgct cactgcagag | 480 |
| aaatacagtg gaattcgctg ggcaatggtt tggcttatga agactttagt ttccccatct | 540 |
| ttcttcttga agatgaaaat gaaaccaaag tcatcaagca gtgctatcaa gatcacaacc | 600 |
| tgagtcagaa tggctcagca ccaaccttcc cactatgtgc catgcagctc ttttcacaca | 660 |
| tgcatgctgt catcagcact gccacctgca tgcggcgcag ctccatccaa agcaccttca | 720 |
| gcatcaaccc agaaatcgtc tgtgaccccc tgtctgatta caatgtgtgg agcatgctaa | 780 |
| agcctataaa tacaactggg acattaaagc ctgacgacag ggttgtggtt gctgccaccc | 840 |
| ggctggatag tcgttccttt ttctggaatg tggccccagg ggctgaaagc gcagtggctt | 900 |

```
cctttgtcac ccagctggct gctgctgaag ctttgcaaaa ggcacctgat gtgaccaccc      960
tgccccgcaa tgtcatgttt gtcttctttc aaggggaaac ttttgactac attggcagct     1020
cgaggatggt ctacgatgga aagggcaag tttcccgtgc agttagagaa tgttgactca      1080
tttgtggagc tgggacaggt ggccttaaga acttcattag agctttggat gcacacagat    1140
cctgtttctc agaaaaatga gtctgtacgg aaccaggtgg aggatctcct ggccacattg    1200
gagaagagtg tgtgctggtgt ccctgctgtc atcctcagga ggccaaatca gtcccagcct   1260
ctcccaccat cttccctgca gcgatttctt cgagctcgaa acatctctgg cgttgttctg    1320
gctgaccact ctggtgcctt ccataacaaa tattaccaga gtatttacga cactgctgag    1380
aacattaatg tgagctatcc cgaatggctg agccctgaag aggacctgaa ctttgtaaca    1440
gacactgcca aggccctggc agatgtggcc acggtgctgg acgtgctct gtatgagctt     1500
gcaggaggaa ccaacttcag cgacacagtt caggctgatc cccaaacggt tacccgcctg    1560
ctctatgggt tcctgattaa agccaacaac tcatggttcc agtctatcct caggcaggac    1620
ctaaggtcct acttgggtga cgggcctctt caacattaca tcgctgtctc cagccccacc    1680
aacaccactt atgttgtaca gtatgccttg gcaaatttga ctggcacagt ggtcaacctc    1740
acccgagagc agtgccagga tccaagtaaa gtcccaagtg aaaacaagga tctgtatgag    1800
tactcatggg tccagggccc tttgcattct aatgagacgg accgactccc ccggtgtgtg    1860
cgttctactg cacgattagc cagggccttg tctcctgcct ttgaactgag tcagtggagc    1920
tctactgaat actctacatg gactgagagc cgctggaaag atatccgtgc ccggatattt    1980
ctcatcgcca gcaaagagct tgagttgatc accctgacag tgggcttcgg catcctcatc    2040
ttctccctca tcgtcaccta ctgcatcaat gccaaagctg atgtcctttt cattgctccc    2100
cgggagccag gagctgtgtc atactgagga ggaccccagc ttttcttgcc agctcagcag    2160
ttcacttcct agagcatctg tcccactggg acacaaccac taatttgtca ctggaacctc    2220
cctgggcctg tctcagattg ggattaacat aaaagagtgg aactatccaa agagacagg    2280
gagaaataaa taaattgcct cccttcctcc gctcccttt cccatcaccc cttccccatt     2340
tcctcttcct tctctactca tgccagattt tgggattaca aatagaagct tcttgctcct   2400
gtttaactcc ctagttaccc accctaattt gcccttcagg accttctac ttttttcctcc   2460
ctgccctgta cctctctctg ctcctcaccc ccacccctgt acccagccac cttcctgact   2520
gggaaggaca taaaaggttt aatgtcaggg tcaaactaca ttgagcccct gaggacaggg   2580
gcatctctgg gctgagccta ctgtctcctt cccactgtcc tttctccagg ccctcagatg   2640
gcacattagg gtgggcgtgc tgcgggtggg tatcccacct ccagcccaca gtgctcagtt   2700
gtactttta ttaagctgta atatctattt ttgttttgt cttttccttt tattcttttt     2760
gtaaatatat atataatgag tttcattaaa atagattatc ccaaaaaaaa aaaaaaaaa    2820
a                                                                    2821

<210> SEQ ID NO 10
<211> LENGTH: 557
<212> TYPE: DNA
<213> ORGANISM: Homo sapiens

<400> SEQUENCE: 10
aactatccaa aagagacagg gagaaataaa taaattgcct cccttcctcc gctcccttt      60
cccatcaccc cttccccatt tcctcttcct tctctactca tgccagattt tgggattaca   120
```

```
aatagaagct tcttgctcct gtttaactcc ctagttaccc accctaattt gcccttcagg    180
acccttctac ttttttcctt ctgccctgta cctctctctg ctcctcaccc ccaccccgt     240 acccagccac cttcctgact gggaaggaca taaaaggttt aatgtcaggg tcaaactaca    300
ttgagcccct gaggacaggg gcatctctgg gctgagccta ctgtctcctt cccactgtcc    360
tttctccagg ccctcagatg gcacattagg gtgggcgtgc tgcgggtggg tatcccacct    420
ccagcccaca gtgctcagtt gtacttttta ttaagctgga atatctattt ttgttttgt     480 cttttccctt tattctttt gtaaatatat atataatgag tttcattaaa atagattatc     540
ccacacgaaa aaaaaaa                                                   557
```

<210> SEQ ID NO 11
<211> LENGTH: 2805
<212> TYPE: DNA
<213> ORGANISM: Homo sapiens
<400> SEQUENCE: 11

```
ggctacggca gggggtggct ctggggctga cccgggaagt cggggtctcc ttcgccttct    60
gtctttctgc gtcctactag caggtttgtg caggggaaac tcagtggaga ggaagatata    120 tatccctta aataaaacag ctccctgtgt tcgcctgctc aacgccactc atcagattgg     180
ctgccagtct tcaattagtg gagacacagg ggttatccac gtagtagaga aagaggagga    240
cctacagtgg gtattgactg atggcccaa ccccccttac atggttctgc tggagagcaa     300
gcattttacc agggatttaa tggagaagct gaaagggaga accagccgaa ttgctggtct    360
tgcagtgtcc ttgaccaagc ccagtcctgc ctcaggcttc tctcctagtg tacagtgccc    420
aaatgatggg tttggtgttt actccaattc ctatgggcca gagtttgctc actgcagaga    480
aatacagtgg aattcgctgg gcaatggttt ggcttatgaa gactttagtt tccccatctt    540
tcttcttgaa gatgaaaatg aaaccaaagt catcaagcag tgctatcaag atcacaacct    600
gagtcagaat ggctcagcac caaccttccc actatgtgcc atgcagctct tttcacacat    660
gcatgctgtc atcagcactg ccacctgcat gcggcgcagc tccatccaaa gcaccttcag    720
catcaaccca gaaatcgtct gtgacccct gtctgattac aatgtgtgga gcatgctaaa    780
gcctataaat acaactggga cattaaagcc tgacgacagg gttgtggttg ctgccacccg    840
gctggatagt cgttccttt tctggaatgt ggccccaggg gctgaaagcg cagtggcttc     900
ctttgtcacc cagctggctg ctgctgaagc tttgcaaaag gcacctgatg tgaccaccct    960
gccccgcaat gtcatgtttg tcttctttca aggggaaact tttgactaca ttggcagctc    1020
gaggatggtc tacgatatgg agaagggcaa gtttcccgtg cagttagaga atgttgactc    1080
atttgtggag ctgggacagg tggccttaag aacttcatta gagctttgga tgcacacaga    1140
tcctgtttct cagaaaaatg agtctgtacg gaaccaggtg gaggatctcc tggccacatt    1200
ggagaagagt ggtgctggtg tccctgctgt catcctcagg aggccaaatc agtcccagcc    1260
tctcccacca tcttccctgc agcgatttct tcgagctcga acatctctg gcgttgttct     1320 ggctgaccac tctggtgcct tccataacaa atattaccag agtatttacg acactgctga    1380
gaacattaat gtgagctatc ccgaatggct gagccctgaa gaggacctga actttgtaac    1440
agacactgcc aaggccctgg cagatgtggc cacggtgctg ggacgtgctc tgtatgagct    1500
tgcaggagga accaacttca gcgacacagt tcaggctgat ccccaaacgg ttacccgcct    1560
gctctatggg ttcctgatta aagccaacaa ctcatggttc cagtctatcc tcaggcagga    1620
cctaaggtcc tacttgggtg acgggcctct tcaacattac atcgctgtct ccagccccac    1680
```

-continued

```
caacaccact tatgttgtac agtatgcctt ggcaaatttg actggcacag tggtcaacct    1740
cacccgagag cagtgccagg atccaagtaa agtcccaagt gaaaacaagg atctgtatga    1800
gtactcatgg gtccagggcc ctttgcattc taatgagacg gaccgactcc cccggtgtgt    1860
gcgttctact gcacgattag ccagggcctt gtctcctgcc tttgaactga gtcagtggag    1920
ctctactgaa tactctacat ggactgagag ccgctggaaa gatatccgtg cccggatatt    1980
tctcatcgcc agcaaagagc ttgagttgat caccctgaca gtgggcttcg gcatcctcat    2040
cttctccctc atcgtcacct actgcatcaa tgccaaagct gatgtccttt tcattgctcc    2100
ccgggagcca ggagctgtgt catactgagg aggaccccag cttttcttgc cagctcagca    2160
gttcacttcc tagagcatct gtcccactgg gacacaacca ctaatttgtc actggaacct    2220
ccctgggcct gtctcagatt gggattaaca taaaagagtg gaactatcca aaagagacag    2280
ggagaaataa ataaattgcc tcccttcctc cgctccccctt tcccatcacc ccttccccat    2340
ttcctcttcc ttctctactc atgccagatt ttgggattac aaatagaagc ttcttgctcc    2400
tgtttaactc cctagttacc caccctaatt tgcccttcag gacccttcta cttttttcctt    2460
cctgccctgt acctctctct gctcctcacc cccaccctg tacccagcca ccttcctgac    2520
tgggaaggac ataaaaggtt taatgtcagg gtcaaactac attgagcccc tgaggacagg    2580
ggcatctctg ggctgagcct actgtctcct tcccactgtc ctttctccag gccctcagat    2640
ggcacattag ggtgggcgtg ctgcgggtgg gtatcccacc tccagcccac agtgctcagt    2700
tgtactttt attaagctgt aatatctatt tttgttttg tcttttttcct ttattcttttt    2760
tgtaaatata tatataatga gtttcattaa aatagattat cccac                    2805
```

<210> SEQ ID NO 12
<211> LENGTH: 467
<212> TYPE: PRT
<213> ORGANISM: Homo sapiens

<400> SEQUENCE: 12

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
                20                  25                  30

Arg Glu Arg Gln Glu His Asn Asp Arg Arg Ser Leu Gly His Pro Glu
            35                  40                  45

Pro Leu Ser Asn Gly Arg Pro Gln Gly Asn Ser Arg Gln Val Val Glu
        50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175
```

```
Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 13
<211> LENGTH: 378
<212> TYPE: PRT
<213> ORGANISM: Homo sapiens

<400> SEQUENCE: 13

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
```

```
                65                  70                  75                  80
His Val Ile Met Leu Phe Val Pro Val Thr Leu Cys Met Val Val
                    85                  90                  95
Val Ala Thr Ile Lys Ser Val Ser Phe Tyr Thr Arg Lys Asp Gly Gln
                100                 105                 110
Leu Ile Tyr Thr Pro Phe Thr Glu Asp Thr Glu Thr Val Gly Gln Gly
                115                 120                 125
Ala Leu His Ser Ile Leu Asn Ala Ala Ile Met Ile Ser Val Ile Val
                130                 135                 140
Val Met Thr Ile Leu Leu Val Val Leu Tyr Lys Tyr Arg Cys Tyr Lys
145                 150                 155                 160
Val Ile His Ala Trp Leu Ile Ile Ser Ser Leu Leu Leu Leu Phe Phe
                    165                 170                 175
Phe Ser Phe Ile Tyr Leu Gly Glu Val Phe Lys Thr Tyr Asn Val Ala
                180                 185                 190
Val Asp Tyr Ile Thr Val Ala Leu Leu Ile Trp Asn Phe Gly Val Val
                195                 200                 205
Gly Met Ile Ser Ile His Trp Lys Gly Pro Leu Arg Leu Gln Gln Ala
                210                 215                 220
Tyr Leu Ile Met Ile Ser Ala Leu Met Ala Leu Val Phe Ile Lys Tyr
225                 230                 235                 240
Leu Pro Glu Trp Thr Ala Trp Leu Ile Leu Ala Val Ile Ser Val Tyr
                    245                 250                 255
Asp Leu Val Ala Val Leu Cys Pro Lys Gly Pro Leu Arg Met Leu Val
                260                 265                 270
Glu Thr Ala Gln Glu Arg Asn Glu Thr Leu Phe Pro Ala Leu Ile Tyr
                275                 280                 285
Ser Ser Thr Met Val Trp Leu Val Asn Met Ala Glu Gly Asp Pro Glu
                290                 295                 300
Ala Gln Arg Arg Val Ser Lys Asn Ser Lys Tyr Asn Ala Glu Arg Ala
305                 310                 315                 320
Cys Leu Pro Pro Ala Ala Ile Asn Leu Leu Ser Ile Ala Pro Met Ala
                    325                 330                 335
Pro Arg Leu Phe Met Pro Lys Gly Ala Cys Arg Pro Thr Ala Gln Lys
                340                 345                 350
Gly Ser His Lys Thr Leu Leu Gln Arg Met Met Met Ala Gly Ser Val
                355                 360                 365
Arg Asn Gly Lys Pro Arg Gly Thr Val Ile
                370                 375

<210> SEQ ID NO 14
<211> LENGTH: 184
<212> TYPE: PRT
<213> ORGANISM: Homo sapiens

<400> SEQUENCE: 14

Met Thr Glu Leu Pro Ala Pro Leu Ser Tyr Phe Gln Asn Ala Gln Met
1               5                   10                  15
Ser Glu Asp Asn His Leu Ser Asn Thr Val Arg Ser Gln Asn Asp Asn
                20                  25                  30
Arg Glu Arg Gln Glu His Asn Asp Arg Arg Ser Leu Gly His Pro Glu
                35                  40                  45
Pro Leu Ser Asn Gly Arg Pro Gln Gly Asn Ser Arg Gln Val Val Glu
                50                  55                  60
```

```
Gln Asp Glu Glu Asp Glu Glu Leu Thr Leu Lys Tyr Gly Ala Lys
 65                  70                  75                  80

His Val Ile Met Leu Phe Val Pro Val Thr Leu Cys Met Val Val
                 85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ser Met Arg His Arg Ser Leu Leu Ser Thr Leu Phe Phe Leu Trp
                165                 170                 175

Leu Gly Ile Leu Val Thr Val Thr
                180

<210> SEQ ID NO 15
<211> LENGTH: 463
<212> TYPE: PRT
<213> ORGANISM: Homo sapiens

<400> SEQUENCE: 15

Met Thr Glu Leu Pro Ala Pro Leu Ser Tyr Phe Gln Asn Ala Gln Met
  1               5                  10                  15

Ser Glu Asp Asn His Leu Ser Asn Thr Asn Asp Asn Arg Glu Arg Gln
             20                  25                  30

Glu His Asn Asp Arg Arg Ser Leu Gly His Pro Glu Pro Leu Ser Asn
         35                  40                  45

Gly Arg Pro Gln Gly Asn Ser Arg Gln Val Val Glu Gln Asp Glu Glu
     50                  55                  60

Glu Asp Glu Glu Leu Thr Leu Lys Tyr Gly Ala Lys His Val Ile Met
 65                  70                  75                  80

Leu Phe Val Pro Val Thr Leu Cys Met Val Val Val Ala Thr Ile
                 85                  90                  95

Lys Ser Val Ser Phe Tyr Thr Pro Lys Asp Gly Gln Leu Ile Tyr Thr
            100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Val Met Thr Ile
        130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Phe Phe Ser Phe Ile
                165                 170                 175

Tyr Leu Gly Glu Val Phe Lys Thr Tyr Asn Val Ala Val Asp Tyr Ile
            180                 185                 190

Thr Val Ala Leu Leu Ile Trp Asn Phe Gly Val Val Gly Met Ile Ser
        195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
            245                 250                 255
```

```
Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285

Val Trp Leu Val Asn Met Ala Glu Gly Asp Pro Gly Ala Gln Arg Arg
    290                 295                 300

Val Ser Lys Asn Ser Lys Tyr Asn Ala Glu Ser Thr Glu Arg Glu Ser
305                 310                 315                 320

Gln Asp Thr Val Ala Glu Asn Asp Asp Gly Gly Phe Ser Glu Glu Trp
                325                 330                 335

Glu Ala Gln Arg Asp Ser His Leu Gly Pro His Arg Ser Thr Pro Glu
            340                 345                 350

Ser Arg Ala Ala Val Gln Glu Leu Ser Ser Ser Ile Leu Ala Gly Glu
        355                 360                 365

Asp Pro Glu Glu Arg Gly Val Lys Leu Gly Leu Gly Asp Phe Ile Phe
    370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
                405                 410                 415

Thr Leu Leu Leu Leu Ala Ile Phe Lys Lys Ala Leu Pro Ala Leu Pro
            420                 425                 430

Ile Ser Ile Thr Phe Gly Leu Val Phe Tyr Phe Ala Thr Asp Tyr Leu
        435                 440                 445

Val Gln Pro Phe Met Asp Gln Leu Ala Phe His Gln Phe Tyr Ile
    450                 455                 460

<210> SEQ ID NO 16
<211> LENGTH: 264
<212> TYPE: PRT
<213> ORGANISM: Homo sapiens

<400> SEQUENCE: 16

Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
            20                  25                  30

Glu His Asn Asp Arg Arg Ser Leu Gly His Pro Glu Pro Leu Ser Asn
        35                  40                  45

Gly Arg Pro Gln Gly Asn Ser Arg Gln Val Val Glu Gln Asp Glu Glu
    50                  55                  60

Glu Asp Glu Glu Leu Thr Leu Lys Tyr Gly Ala Lys His Val Ile Met
65                  70                  75                  80

Leu Phe Val Pro Val Thr Leu Cys Met Val Trp Leu Val Asn Met Ala
                85                  90                  95

Glu Gly Asn Pro Glu Ala Gln Arg Arg Val Ser Lys Asn Ser Lys Tyr
            100                 105                 110

Asn Ala Glu Ser Thr Glu Arg Glu Ser Gln Asp Thr Val Ala Glu Asn
        115                 120                 125

Asp Asp Gly Gly Phe Ser Glu Glu Trp Glu Ala Gln Arg Asp Ser His
    130                 135                 140

Leu Gly Pro His Arg Ser Thr Pro Glu Ser Arg Ala Ala Val Gln Glu
145                 150                 155                 160

Leu Ser Ser Ser Ile Leu Ala Gly Glu Asp Pro Glu Glu Arg Gly Val
```

```
            165                 170                 175
Lys Leu Gly Leu Gly Asp Phe Ile Phe Tyr Ser Val Leu Val Gly Lys
            180                 185                 190

Ala Ser Ala Thr Ala Ser Gly Asp Trp Asn Thr Thr Ile Ala Cys Phe
            195                 200                 205

Val Ala Ile Leu Ile Gly Leu Cys Leu Thr Leu Leu Leu Leu Ala Ile
        210                 215                 220

Phe Lys Lys Ala Leu Pro Ala Leu Pro Ile Ser Ile Thr Phe Gly Leu
225                 230                 235                 240

Val Phe Tyr Phe Ala Thr Asp Tyr Leu Val Gln Pro Phe Met Asp Gln
            245                 250                 255

Leu Ala Phe His Gln Phe Tyr Ile
            260

<210> SEQ ID NO 17
<211> LENGTH: 467
<212> TYPE: PRT
<213> ORGANISM: Homo sapiens

<400> SEQUENCE: 17

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
            85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
            165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
            245                 250                 255

Asp Leu Val Ala Val Leu Cys Pro Lys Gly Pro Leu Arg Met Leu Val
            260                 265                 270
```

```
Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
450                 455                 460

Phe Tyr Ile
465

<210> SEQ ID NO 18
<211> LENGTH: 463
<212> TYPE: PRT
<213> ORGANISM: Homo sapiens

<400> SEQUENCE: 18

Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
                20                  25                  30

Glu His Asn Asp Arg Arg Ser Leu Gly His Pro Glu Pro Leu Ser Asn
            35                  40                  45

Gly Arg Pro Gln Gly Asn Ser Arg Gln Val Val Glu Gln Asp Glu Glu
50                  55                  60

Glu Asp Glu Glu Leu Thr Leu Lys Tyr Gly Ala Lys His Val Ile Met
65                  70                  75                  80

Leu Phe Val Pro Val Thr Leu Cys Met Val Val Val Ala Thr Ile
                85                  90                  95

Lys Ser Val Ser Phe Tyr Thr Arg Lys Asp Gly Gln Leu Ile Tyr Thr
                100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Met Thr Ile
130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Phe Ser Phe Ile
                165                 170                 175
```

```
Tyr Leu Gly Glu Val Phe Lys Thr Tyr Asn Val Ala Val Asp Tyr Ile
            180                 185                 190

Thr Val Ala Leu Leu Ile Trp Asn Phe Gly Val Val Gly Met Ile Ser
        195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
                245                 250                 255

Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285

Val Trp Leu Val Asn Met Ala Glu Gly Asp Pro Glu Ala Gln Arg Arg
    290                 295                 300

Val Ser Lys Asn Ser Lys Tyr Asn Ala Glu Ser Thr Glu Arg Glu Ser
305                 310                 315                 320

Gln Asp Thr Val Ala Glu Asn Asp Asp Gly Gly Phe Ser Glu Glu Trp
                325                 330                 335

Glu Ala Gln Arg Asp Ser His Leu Gly Pro His Arg Ser Thr Pro Glu
            340                 345                 350

Ser Arg Ala Ala Val Gln Glu Leu Ser Ser Ser Ile Leu Ala Gly Glu
        355                 360                 365

Asp Pro Glu Glu Arg Gly Val Lys Leu Gly Leu Gly Asp Phe Ile Phe
    370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
                405                 410                 415

Thr Leu Leu Leu Leu Ala Ile Phe Lys Lys Ala Leu Pro Ala Leu Pro
            420                 425                 430

Ile Ser Ile Thr Phe Gly Leu Val Phe Tyr Phe Ala Thr Asp Tyr Leu
        435                 440                 445

Val Gln Pro Phe Met Asp Gln Leu Ala Phe His Gln Phe Tyr Ile
    450                 455                 460

<210> SEQ ID NO 19
<211> LENGTH: 467
<212> TYPE: PRT
<213> ORGANISM: Homo sapiens

<400> SEQUENCE: 19

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
```

```
                  85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
                115                 120                 125

Ala Leu His Ser Ile Leu Asn Ala Ala Ile Met Ile Ser Val Ile Val
                130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
                195                 200                 205

Gly Met Ile Ser Ile His Trp Lys Gly Pro Leu Arg Leu Gln Gln Ala
                210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
                275                 280                 285

Ser Ser Thr Met Val Trp Leu Val Asn Met Ala Glu Gly Asp Pro Glu
                290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
                355                 360                 365

Leu Ala Gly Glu Asp Pro Glu Glu Arg Gly Val Lys Leu Gly Leu Gly
                370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
                435                 440                 445

Thr Asp Tyr Leu Val Gln Pro Phe Met Asp Gln Leu Ala Phe His Gln
                450                 455                 460

Phe Tyr Ile
465

<210> SEQ ID NO 20
<211> LENGTH: 463
<212> TYPE: PRT
<213> ORGANISM: Homo sapiens
```

<400> SEQUENCE: 20

```
Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
            20                  25                  30

Glu His Asn Asp Arg Arg Ser Leu Gly His Pro Glu Pro Leu Ser Asn
        35                  40                  45

Gly Arg Pro Gln Gly Asn Ser Arg Gln Val Val Gln Asp Glu Glu
50                  55                  60

Glu Asp Glu Glu Leu Thr Leu Lys Tyr Gly Ala Lys His Val Ile Met
65                  70                  75                  80

Leu Phe Val Pro Val Thr Leu Cys Met Val Val Val Ala Thr Ile
                85                  90                  95

Lys Ser Val Ser Phe Tyr Thr Arg Lys Asp Gly Gln Leu Ile Tyr Thr
                100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Val Met Thr Ile
130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Phe Phe Phe Ser Phe Ile
                165                 170                 175

Tyr Leu Gly Glu Val Phe Lys Thr Tyr Asn Val Ala Val Asp Tyr Ile
            180                 185                 190

Thr Val Ala Leu Leu Ile Trp Asn Leu Gly Val Val Gly Met Ile Ser
            195                 200                 205

Ile His Trp Lys Gly Pro Leu Arg Leu Gln Gln Ala Tyr Leu Ile Met
        210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
                245                 250                 255

Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285

Val Trp Leu Val Asn Met Ala Glu Gly Asp Pro Glu Ala Gln Arg Arg
    290                 295                 300

Val Ser Lys Asn Ser Lys Tyr Asn Ala Glu Ser Thr Glu Arg Glu Ser
305                 310                 315                 320

Gln Asp Thr Val Ala Glu Asn Asp Asp Gly Gly Phe Ser Glu Glu Trp
                325                 330                 335

Glu Ala Gln Arg Asp Ser His Leu Gly Pro His Arg Ser Thr Pro Glu
            340                 345                 350

Ser Arg Ala Ala Val Gln Glu Leu Ser Ser Ile Leu Ala Gly Glu
        355                 360                 365

Asp Pro Glu Glu Arg Gly Val Lys Leu Gly Leu Gly Asp Phe Ile Phe
    370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
```

```
                    405                 410                 415
Thr Leu Leu Leu Leu Ala Ile Phe Lys Lys Ala Leu Pro Ala Leu Pro
            420                 425                 430

Ile Ser Ile Thr Phe Gly Leu Val Phe Tyr Phe Ala Thr Asp Tyr Leu
            435                 440                 445

Val Gln Pro Phe Met Asp Gln Leu Ala Phe His Gln Phe Tyr Ile
            450                 455                 460

<210> SEQ ID NO 21
<211> LENGTH: 463
<212> TYPE: PRT
<213> ORGANISM: Homo sapiens

<400> SEQUENCE: 21

Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
            20                  25                  30

Glu His Asn Asp Arg Arg Ser Leu Gly His Pro Glu Pro Leu Ser Asn
        35                  40                  45

Gly Arg Pro Gln Gly Asn Ser Arg Gln Val Val Glu Gln Asp Glu Glu
    50                  55                  60

Glu Asp Glu Glu Leu Thr Leu Lys Tyr Gly Ala Lys His Val Ile Met
65                  70                  75                  80

Leu Phe Val Pro Val Thr Leu Cys Met Val Val Val Ala Thr Ile
            85                  90                  95

Lys Ser Val Ser Phe Tyr Thr Arg Lys Asp Gly Gln Leu Ile Tyr Thr
            100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Val Met Thr Ile
        130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Phe Ser Phe Ile
            165                 170                 175

Tyr Leu Gly Glu Val Phe Lys Thr Tyr Asn Val Ala Val Asp Tyr Ile
            180                 185                 190

Thr Val Ala Leu Leu Ile Trp Asn Phe Gly Val Val Gly Met Ile Ser
        195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
            245                 250                 255

Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285

Val Trp Leu Val Asn Met Ala Glu Gly Asp Pro Glu Ala Gln Arg Arg
    290                 295                 300

Val Ser Lys Asn Ser Lys Tyr Asn Ala Glu Ser Thr Glu Arg Glu Ser
305                 310                 315                 320
```

-continued

```
Gln Asp Thr Val Ala Glu Asn Asp Asp Gly Gly Phe Ser Glu Glu Trp
                325                 330                 335

Glu Ala Gln Arg Asp Ser His Leu Gly Pro His Arg Ser Thr Pro Glu
            340                 345                 350

Ser Arg Ala Ala Val Gln Glu Leu Ser Ser Ile Leu Ala Gly Glu
        355                 360                 365

Asp Pro Glu Glu Arg Gly Val Lys Leu Gly Leu Gly Asp Phe Ile Phe
    370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
                405                 410                 415

Thr Leu Leu Leu Leu Ala Ile Phe Lys Lys Ala Leu Pro Ala Leu Pro
            420                 425                 430

Ile Ser Ile Thr Phe Gly Leu Val Phe Tyr Phe Ala Thr Asp Tyr Leu
        435                 440                 445

Val Gln Pro Phe Met Asp Gln Leu Ala Phe His Gln Phe Tyr Ile
    450                 455                 460

<210> SEQ ID NO 22
<211> LENGTH: 374
<212> TYPE: PRT
<213> ORGANISM: Homo sapiens

<400> SEQUENCE: 22

Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
            20                  25                  30

Glu His Asn Asp Arg Arg Ser Leu Gly His Pro Glu Pro Leu Ser Asn
        35                  40                  45

Gly Arg Pro Gln Gly Asn Ser Arg Gln Val Val Glu Gln Asp Glu Glu
    50                  55                  60

Glu Asp Glu Glu Leu Thr Leu Lys Tyr Gly Ala Lys His Val Ile Met
65                  70                  75                  80

Leu Phe Val Pro Val Thr Leu Cys Met Val Val Val Ala Thr Ile
                85                  90                  95

Lys Ser Val Ser Phe Tyr Thr Arg Lys Asp Gly Gln Leu Ile Tyr Thr
            100                 105                 110

Pro Phe Thr Glu Asp Thr Glu Thr Val Gly Gln Arg Ala Leu His Ser
        115                 120                 125

Ile Leu Asn Ala Ala Ile Met Ile Ser Val Ile Val Val Met Thr Ile
    130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Phe Ser Phe Ile
                165                 170                 175

Tyr Leu Gly Glu Val Phe Lys Thr Tyr Asn Val Ala Val Asp Tyr Ile
            180                 185                 190

Thr Val Ala Leu Leu Ile Trp Asn Phe Gly Val Val Gly Met Ile Ser
        195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
225                 230                 235                 240
```

```
Thr Ala Trp Leu Ile Leu Ala Val Ile Ser Val Tyr Asp Leu Val Ala
                245                 250                 255

Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285

Val Trp Leu Val Asn Met Ala Glu Gly Asp Pro Glu Ala Gln Arg Arg
290                 295                 300

Val Ser Lys Asn Ser Lys Tyr Asn Ala Glu Arg Ala Cys Leu Pro Pro
305                 310                 315                 320

Ala Ala Ile Asn Leu Leu Ser Ile Ala Pro Met Ala Pro Arg Leu Phe
                325                 330                 335

Met Pro Lys Gly Ala Cys Arg Pro Thr Ala Gln Lys Gly Ser His Lys
            340                 345                 350

Thr Leu Leu Gln Arg Met Met Met Ala Gly Ser Val Arg Asn Gly Lys
        355                 360                 365

Pro Arg Gly Thr Val Ile
    370
```

<210> SEQ ID NO 23
<211> LENGTH: 463
<212> TYPE: PRT
<213> ORGANISM: Homo sapiens
<400> SEQUENCE: 23

```
Met Thr Glu Leu Pro Ala Pro Leu Ser Tyr Phe Gln Asn Ala Gln Met
1               5                   10                  15

Ser Glu Asp Asn His Leu Ser Asn Thr Asn Asp Asn Arg Glu Arg Gln
                20                  25                  30

Glu His Asn Asp Arg Arg Ser Leu Gly His Pro Glu Pro Leu Ser Asn
            35                  40                  45

Gly Arg Pro Gln Gly Asn Ser Arg Gln Val Val Glu Gln Asp Glu Glu
        50                  55                  60

Glu Asp Glu Glu Leu Thr Leu Lys Tyr Gly Ala Lys His Val Ile Met
65                  70                  75                  80

Leu Phe Val Pro Val Thr Leu Cys Met Val Val Val Val Ala Thr Ile
                85                  90                  95

Lys Ser Val Ser Phe Tyr Thr Arg Lys Asp Gly Gln Leu Ile Tyr Thr
                100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Val Met Thr Ile
        130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Phe Ser Phe Ile
                165                 170                 175

Tyr Leu Gly Glu Val Phe Lys Thr Tyr Asn Val Ala Val Asp Tyr Ile
            180                 185                 190

Thr Val Ala Leu Leu Ile Trp Asn Phe Gly Val Val Gly Met Ile Ser
        195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
```

```
            225                 230                 235                 240
    Thr Ala Trp Leu Ile Leu Ala Val Ile Ser Val Tyr Asp Leu Val Ala
                    245                 250                 255

Val Leu Cys Pro Lys Gly Pro Leu Arg Met Leu Val Glu Thr Ala Gln
                    260                 265                 270

Glu Arg Asn Glu Thr Leu Phe Pro Ala Leu Ile Tyr Ser Ser Thr Met
                    275                 280                 285

Val Trp Leu Val Asn Met Ala Glu Gly Asp Pro Glu Ala Gln Arg Arg
                290                 295                 300

Val Ser Lys Asn Ser Lys Tyr Asn Ala Glu Ser Thr Glu Arg Glu Ser
    305                 310                 315                 320

Gln Asp Thr Val Ala Glu Asn Asp Asp Gly Gly Phe Ser Glu Glu Trp
                    325                 330                 335

Glu Ala Gln Arg Asp Ser His Leu Gly Pro His Arg Ser Thr Pro Glu
                    340                 345                 350

Ser Arg Ala Ala Val Gln Glu Leu Ser Ser Ser Ile Leu Ala Gly Glu
                    355                 360                 365

Asp Pro Glu Glu Arg Gly Val Lys Leu Gly Leu Gly Asp Phe Ile Phe
                370                 375                 380

Tyr Ser Val Leu Val Gly Lys Ala Ser Ala Thr Ala Ser Gly Asp Trp
    385                 390                 395                 400

Asn Thr Thr Ile Ala Cys Phe Val Ala Ile Leu Ile Gly Leu Cys Leu
                    405                 410                 415

Thr Leu Leu Leu Leu Ala Ile Phe Lys Lys Ala Leu Pro Ala Leu Pro
                    420                 425                 430

Ile Ser Ile Thr Phe Gly Leu Val Phe Tyr Phe Ala Thr Asp Tyr Leu
                    435                 440                 445

Val Gln Pro Phe Met Asp Gln Leu Ala Phe His Gln Phe Tyr Ile
                450                 455                 460

<210> SEQ ID NO 24
<211> LENGTH: 448
<212> TYPE: PRT
<213> ORGANISM: Homo sapiens

<400> SEQUENCE: 24

Met Leu Thr Phe Met Ala Ser Asp Ser Glu Glu Val Cys Asp Glu
    1               5                   10                  15

Arg Thr Ser Leu Met Ser Ala Glu Ser Pro Thr Pro Arg Ser Cys Gln
                    20                  25                  30

Glu Gly Arg Gln Gly Pro Glu Asp Gly Glu Asn Thr Ala Gln Trp Arg
                35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
    65                  70                  75                  80

Leu Lys Tyr Gly Ala Lys His Val Ile Met Leu Phe Val Pro Val Thr
                    85                  90                  95

Leu Cys Met Ile Val Val Ala Thr Ile Lys Ser Val Arg Phe Tyr
                    100                 105                 110

Thr Glu Lys Asn Gly Gln Leu Ile Tyr Thr Pro Phe Thr Glu Asp Thr
                115                 120                 125

Pro Ser Val Gly Gln Arg Leu Leu Asn Ser Val Leu Asn Thr Leu Ile
                130                 135                 140
```

-continued

```
Met Ile Ser Val Ile Val Met Thr Ile Phe Leu Val Val Leu Tyr
145                 150                 155                 160

Lys Tyr Arg Cys Tyr Lys Phe Ile His Gly Trp Leu Ile Met Ser Ser
            165                 170                 175

Leu Met Leu Leu Phe Leu Phe Thr Tyr Ile Tyr Leu Gly Glu Val Leu
                180                 185                 190

Lys Thr Tyr Asn Val Ala Met Asp Tyr Pro Thr Leu Leu Thr Val
        195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445

<210> SEQ ID NO 25
<211> LENGTH: 390
<212> TYPE: PRT
<213> ORGANISM: Homo sapiens

<400> SEQUENCE: 25

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80
```

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
            100                 105                 110

Thr Glu Lys Asn Gly Gln Leu Ile Tyr Thr Thr Phe Thr Glu Asp Thr
            115                 120                 125

Pro Ser Val Gly Gln Arg Leu Leu Asn Ser Val Leu Asn Thr Leu Ile
        130                 135                 140

Met Ile Ser Val Ile Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Arg Asn Glu Pro Ile
        275                 280                 285

Phe Pro Ala Leu Ile Tyr Leu Ser Ala Met Val Trp Thr Val Gly Met
        290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Ala Thr Gly Ser Gly Asp
        370                 375                 380

Trp Asn Thr Thr Leu Ala
385                 390

<210> SEQ ID NO 26
<211> LENGTH: 447
<212> TYPE: PRT
<213> ORGANISM: Homo sapiens

<400> SEQUENCE: 26

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val

```
            50                  55                  60
Cys Ser Gly Val Pro Gly Arg Pro Gly Leu Glu Glu Leu Thr
 65                  70                  75                  80

Leu Lys Tyr Gly Ala Lys His Val Ile Met Leu Phe Val Thr
                     85                  90                  95

Leu Cys Met Ile Val Val Ala Thr Ile Lys Ser Val Arg Phe Tyr
                    100                 105                 110

Thr Glu Lys Asn Gly Gln Leu Ile Tyr Thr Pro Phe Thr Glu Asp Thr
                115                 120                 125

Pro Ser Val Gly Gln Arg Leu Leu Asn Ser Val Leu Asn Thr Leu Ile
130                 135                 140

Met Ile Ser Val Ile Val Met Thr Ile Phe Leu Val Val Leu Tyr
145                 150                 155                 160

Lys Tyr Arg Cys Tyr Lys Phe Ile His Gly Trp Leu Ile Met Ser Ser
                    165                 170                 175

Leu Met Leu Leu Phe Leu Phe Thr Tyr Ile Tyr Leu Gly Glu Val Leu
                    180                 185                 190

Lys Thr Tyr Asn Val Ala Met Asp Tyr Pro Thr Leu Leu Leu Thr Val
                    195                 200                 205

Trp Asn Phe Gly Ala Val Gly Met Val Cys Ile His Trp Lys Gly Pro
210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                    245                 250                 255

Gly Ala Ile Ser Val Tyr Asp Leu Val Ala Val Leu Cys Pro Lys Gly
                    260                 265                 270

Pro Leu Arg Met Leu Val Glu Thr Ala Gln Glu Arg Asn Glu Pro Ile
                    275                 280                 285

Phe Pro Ala Leu Ile Tyr Ser Ser Ala Met Val Trp Thr Val Gly Met
                    290                 295                 300

Ala Lys Leu Asp Pro Ser Ser Gln Gly Ala Leu Gln Leu Pro Tyr Asp
305                 310                 315                 320

Pro Glu Met Glu Asp Ser Tyr Asp Ser Phe Gly Glu Pro Ser Tyr Pro
                    325                 330                 335

Glu Val Phe Glu Pro Pro Leu Thr Gly Tyr Pro Gly Glu Glu Leu Glu
                    340                 345                 350

Glu Glu Glu Glu Arg Gly Val Lys Leu Gly Leu Gly Asp Phe Ile Phe
                    355                 360                 365

Tyr Ser Val Leu Val Gly Lys Ala Ala Ala Thr Gly Ser Gly Asp Trp
370                 375                 380

Asn Thr Thr Leu Ala Cys Phe Val Ala Ile Leu Ile Gly Leu Cys Leu
385                 390                 395                 400

Thr Leu Leu Leu Leu Ala Val Phe Lys Lys Ala Leu Pro Ala Leu Pro
                    405                 410                 415

Ile Ser Ile Thr Phe Gly Leu Ile Phe Tyr Phe Ser Thr Asp Asn Leu
                    420                 425                 430

Val Arg Pro Phe Met Asp Thr Leu Ala Ser His Gln Leu Tyr Ile
                    435                 440                 445

<210> SEQ ID NO 27
<211> LENGTH: 359
<212> TYPE: PRT
<213> ORGANISM: Homo sapiens
```

<400> SEQUENCE: 27

Met Leu Phe Val Pro Val Thr Leu Cys Met Ile Val Val Ala Thr
1               5                   10                  15

Ile Lys Ser Val Arg Phe Tyr Thr Glu Lys Asn Gly Gln Leu Ile Tyr
            20                  25                  30

Thr Pro Phe Thr Glu Asp Thr Pro Ser Val Gly Gln Arg Leu Leu Asn
            35                  40                  45

Ser Val Leu Asn Thr Leu Ile Met Ile Ser Val Ile Val Val Met Thr
        50                  55                  60

Ile Phe Leu Val Val Leu Tyr Lys Tyr Arg Cys Tyr Lys Phe Ile His
65                  70                  75                  80

Gly Trp Leu Ile Met Ser Ser Leu Met Leu Leu Phe Leu Phe Thr Tyr
                    85                  90                  95

Ile Tyr Leu Gly Glu Val Leu Lys Thr Tyr Asn Val Ala Met Asp Tyr
                    100                 105                 110

Pro Thr Leu Leu Leu Thr Val Trp Asn Phe Gly Ala Val Gly Met Val
                    115                 120                 125

Cys Ile His Trp Lys Gly Pro Leu Val Leu Gln Gln Ala Tyr Leu Ile
            130                 135                 140

Met Ile Ser Ala Leu Met Ala Leu Val Phe Ile Lys Tyr Leu Pro Glu
145                 150                 155                 160

Trp Ser Ala Trp Val Ile Leu Gly Ala Ile Ser Val Tyr Asp Leu Val
                    165                 170                 175

Ala Val Leu Cys Pro Lys Gly Pro Leu Arg Met Leu Val Glu Thr Ala
                    180                 185                 190

Gln Glu Arg Asn Glu Pro Ile Phe Pro Ala Leu Ile Tyr Ser Ser Ala
            195                 200                 205

Met Val Trp Thr Val Gly Met Ala Lys Leu Asp Pro Ser Ser Gln Gly
210                 215                 220

Ala Leu Gln Leu Pro Tyr Asp Pro Glu Met Glu Glu Asp Ser Tyr Asp
225                 230                 235                 240

Ser Phe Gly Glu Pro Ser Tyr Pro Glu Val Phe Glu Pro Pro Leu Thr
                    245                 250                 255

Gly Tyr Pro Gly Glu Glu Leu Glu Glu Glu Glu Arg Gly Val Lys
                    260                 265                 270

Leu Gly Leu Gly Asp Phe Ile Phe Tyr Ser Val Leu Val Gly Lys Ala
            275                 280                 285

Ala Ala Thr Gly Ser Gly Asp Trp Asn Thr Thr Leu Ala Cys Phe Val
290                 295                 300

Ala Ile Leu Ile Gly Leu Cys Leu Thr Leu Leu Leu Leu Ala Val Phe
305                 310                 315                 320

Lys Lys Ala Leu Pro Ala Leu Pro Ile Ser Ile Thr Phe Gly Leu Ile
                    325                 330                 335

Phe Tyr Phe Ser Thr Asp Asn Leu Val Arg Pro Phe Met Asp Thr Leu
                    340                 345                 350

Ala Ser His Gln Leu Tyr Ile
        355

<210> SEQ ID NO 28
<211> LENGTH: 448
<212> TYPE: PRT
<213> ORGANISM: Homo sapiens

<400> SEQUENCE: 28

```
Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
                100                 105                 110

Thr Glu Lys Asn Gly Gln Leu Ile Tyr Thr Pro Phe Thr Glu Asp Thr
            115                 120                 125

Pro Ser Val Gly Gln Arg Leu Leu Asn Ser Val Leu Asn Thr Leu Ile
130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
            275                 280                 285

Phe Pro Ala Leu Ile Tyr Ser Ser Ala Met Val Trp Thr Val Gly Met
290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Thr Gly Ser Gly Asp
370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415
```

```
Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445

<210> SEQ ID NO 29
<211> LENGTH: 448
<212> TYPE: PRT
<213> ORGANISM: Homo sapiens

<400> SEQUENCE: 29

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Gly Leu Glu Glu Glu Leu Thr
65              70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
                100                 105                 110

Thr Glu Lys Asn Gly Gln Leu Ile Tyr Thr Pro Phe Thr Glu Asp Thr
            115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
                180                 185                 190

Lys Thr Tyr Asn Val Ala Met Asp Tyr Pro Thr Leu Leu Leu Thr Val
            195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
            275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350
```

```
Glu Glu Glu Glu Glu Arg Gly Val Lys Leu Gly Leu Gly Asp Phe Ile
                355                 360                 365

Phe Tyr Ser Val Leu Val Gly Lys Ala Ala Ala Thr Gly Ser Gly Asp
        370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
                420                 425                 430

Leu Val Arg Pro Phe Met Asp Thr Leu Ala Ser His Gln Leu Tyr Ile
            435                 440                 445

<210> SEQ ID NO 30
<211> LENGTH: 448
<212> TYPE: PRT
<213> ORGANISM: Homo sapiens

<400> SEQUENCE: 30

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
                100                 105                 110

Thr Glu Lys Asn Gly Gln Leu Ile Tyr Thr Thr Phe Thr Glu Asp Thr
            115                 120                 125

Pro Ser Val Gly Gln Arg Leu Leu Asn Ser Val Leu Asn Thr Leu Ile
        130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
                180                 185                 190

Lys Thr Tyr Asn Val Ala Met Asp Tyr Pro Thr Leu Leu Leu Thr Val
            195                 200                 205

Trp Asn Phe Gly Ala Val Gly Met Val Cys Ile His Trp Lys Gly Pro
        210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
```

```
                275                 280                 285
Phe Pro Ala Leu Ile Tyr Ser Ser Ala Met Val Trp Thr Val Gly Met
290                 295                 300
Ala Lys Leu Asp Pro Ser Ser Gln Gly Ala Leu Gln Leu Pro Tyr Asp
305                 310                 315                 320
Pro Glu Met Glu Glu Asp Ser Tyr Asp Ser Phe Gly Pro Glu Ser Tyr
                325                 330                 335
Pro Glu Val Phe Glu Pro Pro Leu Thr Gly Tyr Pro Gly Glu Leu
                340                 345                 350
Glu Glu Glu Glu Arg Gly Val Lys Leu Gly Leu Gly Asp Phe Ile
                355                 360                 365
Phe Tyr Ser Val Leu Val Gly Lys Ala Ala Ala Thr Gly Ser Gly Asp
370                 375                 380
Trp Asn Thr Thr Leu Ala Cys Phe Val Ala Ile Leu Ile Gly Leu Cys
385                 390                 395                 400
Leu Thr Leu Leu Leu Leu Ala Val Phe Lys Lys Ala Leu Pro Ala Leu
                405                 410                 415
Pro Ile Ser Ile Thr Phe Gly Leu Ile Phe Tyr Phe Ser Thr Asp Asn
                420                 425                 430
Leu Val Arg Pro Phe Met Asp Thr Leu Ala Ser His Gln Leu Tyr Ile
                435                 440                 445

<210> SEQ ID NO 31
<211> LENGTH: 448
<212> TYPE: PRT
<213> ORGANISM: Homo sapiens

<400> SEQUENCE: 31

Met Leu Thr Phe Met Ala Ser Asp Ser Glu Glu Val Cys Asp Glu
1               5                   10                  15
Arg Thr Ser Leu Met Ser Ala Glu Ser Pro Thr Pro Arg Ser Cys Gln
                20                  25                  30
Glu Gly Arg Gln Gly Pro Glu Asp Gly Glu Asn Thr Ala Gln Trp Arg
            35                  40                  45
Ser Gln Glu Asn Glu Glu Asp Gly Glu Leu Asp Pro Asp Arg Tyr Val
        50                  55                  60
Cys Ser Gly Val Pro Gly Arg Pro Pro Gly Leu Glu Glu Glu Leu Thr
65                  70                  75                  80
Leu Lys Tyr Gly Ala Lys His Val Ile Met Leu Phe Val Pro Val Thr
                85                  90                  95
Leu Cys Met Ile Val Val Val Ala Thr Ile Lys Ser Val Arg Phe Tyr
                100                 105                 110
Thr Glu Lys Asn Gly Gln Leu Ile Tyr Thr Pro Phe Thr Glu Asp Thr
            115                 120                 125
Pro Ser Val Gly Gln Arg Leu Leu Asn Ser Val Leu Asn Thr Leu Ile
        130                 135                 140
Met Ile Ser Val Ile Val Val Met Thr Ile Phe Leu Val Val Leu Tyr
145                 150                 155                 160
Lys Tyr Arg Cys Tyr Lys Phe Ile His Gly Trp Leu Ile Met Ser Ser
                165                 170                 175
Leu Met Leu Leu Phe Leu Phe Thr Tyr Ile Tyr Leu Gly Glu Val Leu
                180                 185                 190
Lys Thr Tyr Asn Val Ala Met Asp Tyr Pro Thr Leu Leu Leu Thr Val
            195                 200                 205
```

```
Trp Asn Phe Gly Ala Val Gly Met Val Cys Ile His Trp Lys Gly Pro
    210                 215                 220
Leu Val Leu Gln Gln Ala Tyr Leu Ile Met Ile Ser Ala Leu Met Ala
225                 230                 235                 240
Leu Val Phe Ile Lys Tyr Leu Pro Glu Trp Ser Ala Trp Val Ile Leu
                245                 250                 255
Gly Ala Ile Ser Val Tyr Asp Leu Val Ala Val Leu Cys Pro Lys Gly
                260                 265                 270
Pro Leu Arg Met Leu Val Glu Thr Ala Gln Glu Arg Asn Glu Pro Ile
            275                 280                 285
Phe Pro Ala Leu Ile Tyr Ser Ser Ala Met Val Trp Thr Val Gly Met
290                 295                 300
Ala Lys Leu Asp Pro Ser Ser Gln Gly Ala Leu Gln Leu Pro Tyr Asp
305                 310                 315                 320
Pro Glu Met Glu Glu Asp Ser Tyr Asp Ser Phe Gly Glu Pro Ser Tyr
                325                 330                 335
Pro Glu Val Phe Glu Pro Pro Leu Thr Gly Tyr Pro Gly Glu Glu Leu
                340                 345                 350
Glu Glu Glu Glu Glu Arg Gly Val Lys Leu Gly Leu Gly Asp Phe Ile
            355                 360                 365
Phe Tyr Ser Val Leu Val Gly Lys Ala Ala Ala Thr Gly Ser Gly Asp
370                 375                 380
Trp Asn Thr Thr Leu Ala Cys Phe Val Ala Ile Leu Ile Gly Leu Cys
385                 390                 395                 400
Leu Thr Leu Leu Leu Leu Ala Val Phe Lys Lys Ala Leu Pro Ala Leu
                405                 410                 415
Pro Ile Ser Ile Thr Phe Gly Leu Ile Phe Tyr Phe Ser Thr Asp Asn
                420                 425                 430
Leu Val Arg Pro Phe Met Asp Thr Leu Ala Ser His Gln Leu Tyr Ile
            435                 440                 445

<210> SEQ ID NO 32
<211> LENGTH: 442
<212> TYPE: PRT
<213> ORGANISM: Homo sapiens

<400> SEQUENCE: 32

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
                100                 105                 110

Thr Glu Lys Asn Gly Gln Leu Ile Tyr Thr Pro Phe Thr Glu Asp Thr
            115                 120                 125

Pro Ser Val Gly Gln Arg Leu Leu Asn Ser Val Leu Asn Thr Leu Ile
130                 135                 140
```

```
Met Ile Ser Val Ile Val Met Thr Ile Phe Leu Val Val Leu Tyr
145                 150                 155                 160

Lys Tyr Arg Cys Tyr Lys Phe Ile His Gly Trp Leu Ile Met Ser Ser
            165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Thr Val
        195                 200                 205

Trp Asn Phe Gly Ala Val Gly Met Val Cys Ile His Trp Lys Gly Pro
        210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
            245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
290                 295                 300

Ala Lys Leu Asp Pro Ser Ser Gln Gly Ala Leu Gln Leu Pro Tyr Asp
305                 310                 315                 320

Pro Glu Met Glu Asp Ser Tyr Asp Ser Phe Gly Pro Ser Tyr Pro
            325                 330                 335

Glu Val Phe Glu Pro Pro Leu Thr Gly Tyr Pro Gly Glu Glu Leu Glu
            340                 345                 350

Glu Glu Glu Glu Ser Gln Gly Gly Val Lys Leu Gly Leu Gly Asp Phe
        355                 360                 365

Ile Phe Tyr Ser Val Leu Val Gly Lys Ala Ala Thr Gly Ser Gly
        370                 375                 380

Asp Trp Asn Thr Thr Leu Ala Cys Phe Val Ala Ile Leu Ile Gly Leu
385                 390                 395                 400

Cys Leu Thr Leu Leu Leu Ala Val Phe Lys Lys Ala Leu Pro Ala
            405                 410                 415

Leu Pro Ile Ser Ile Thr Phe Gly Leu Ile Phe Tyr Phe Ser Thr Asp
        420                 425                 430

Arg Lys His Ser Arg Phe Ile Gln Met Asn
        435                 440

<210> SEQ ID NO 33
<211> LENGTH: 265
<212> TYPE: PRT
<213> ORGANISM: Homo sapiens

<400> SEQUENCE: 33

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
50                  55                  60

Ala Arg Leu Gln Tyr Gly Leu Leu Ile Phe Gly Ala Ala Val Ser Val
```

```
            65                  70                  75                  80
Leu Leu Gln Glu Val Phe Arg Phe Ala Tyr Tyr Lys Leu Leu Lys Lys
                    85                  90                  95

Ala Asp Glu Gly Leu Ala Ser Leu Ser Glu Asp Gly Arg Ser Pro Ile
                100                 105                 110

Ser Ile Arg Gln Met Ala Tyr Val Ser Gly Leu Ser Phe Gly Ile Ile
                115                 120                 125

Ser Gly Val Phe Ser Val Ile Asn Ile Leu Ala Asp Ala Leu Gly Pro
            130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
                180                 185                 190

Val Val Gly Ser His Leu Leu Thr Ser Gly Leu Thr Phe Leu Asn Pro
            195                 200                 205

Trp Tyr Glu Ala Ser Leu Leu Pro Ile Tyr Ala Val Thr Val Ser Met
        210                 215                 220

Gly Leu Trp Ala Phe Ile Thr Ala Gly Gly Ser Leu Arg Ser Ile Gln
225                 230                 235                 240

Arg Ser Leu Leu Cys Arg Arg Gln Glu Asp Ser Arg Val Met Val Tyr
                245                 250                 255

Ser Ala Leu Arg Ile Pro Pro Glu Asp
                260                 265

<210> SEQ ID NO 34
<211> LENGTH: 251
<212> TYPE: PRT
<213> ORGANISM: Homo sapiens

<400> SEQUENCE: 34

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
                20                  25                  30

Ile Ile Leu Val Ala Gly Ala Phe Phe Trp Leu Val Ser Leu Leu Leu
            35                  40                  45

Ala Ser Val Val Trp Phe Ile Leu Val His Val Thr Asp Arg Ser Asp
        50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                    85                  90                  95

Ala Asp Glu Gly Leu Ala Ser Leu Ser Glu Asp Gly Arg Ser Pro Ile
                100                 105                 110

Ser Ile Arg Gln Met Ala Tyr Val Ser Gly Leu Ser Phe Gly Ile Ile
                115                 120                 125

Ser Gly Val Phe Ser Val Ile Asn Ile Leu Ala Asp Ala Leu Gly Pro
            130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175
```

```
Val Phe Phe Asp Ala Cys Glu Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Leu Arg Ser Ile Gln
225                 230                 235                 240

Arg Ser Ser Cys Val Arg Thr Asp Tyr Leu Asp
                245                 250

<210> SEQ ID NO 35
<211> LENGTH: 251
<212> TYPE: PRT
<213> ORGANISM: Homo sapiens

<400> SEQUENCE: 35

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Leu Arg Ser Ile Gln
225                 230                 235                 240

Arg Ser Ser Cys Val Arg Thr Asp Tyr Leu Asp
                245                 250

<210> SEQ ID NO 36
<211> LENGTH: 247
<212> TYPE: PRT
<213> ORGANISM: Homo sapiens

<400> SEQUENCE: 36
```

```
Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
                20                  25                  30

Ile Ile Leu Val Ala Gly Ala Phe Phe Trp Leu Val Ser Leu Leu Leu
            35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
                100                 105                 110

Ser Ile Arg Gln Met Ala Tyr Val Ser Gly Leu Ser Phe Gly Ile Ile
            115                 120                 125

Ser Gly Val Phe Ser Val Ile Asn Ile Leu Ala Asp Ala Leu Gly Pro
        130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
                180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
                245

<210> SEQ ID NO 37
<211> LENGTH: 247
<212> TYPE: PRT
<213> ORGANISM: Homo sapiens

<400> SEQUENCE: 37

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
                20                  25                  30

Ile Ile Leu Val Ala Gly Ala Phe Phe Trp Leu Val Ser Leu Leu Leu
            35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
                100                 105                 110

Ser Ile Arg Gln Met Ala Tyr Val Ser Gly Leu Ser Phe Gly Ile Ile
            115                 120                 125
```

```
Ser Gly Val Phe Ser Val Ile Asn Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
                180                 185                 190

Val Val Gly Ser His Leu Leu Thr Ser Gly Leu Thr Phe Leu Asn Pro
            195                 200                 205

Trp Tyr Glu Ala Ser Leu Leu Pro Ile Tyr Ala Val Thr Val Ser Met
        210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
                245

<210> SEQ ID NO 38
<211> LENGTH: 247
<212> TYPE: PRT
<213> ORGANISM: Homo sapiens

<400> SEQUENCE: 38

Met Gly Ala Ala Val Phe Cys Gly Cys Thr Phe Val Ala Phe Gly Pro
1               5                   10                  15

Ala Phe Ala Leu Phe Leu Ile Thr Val Ala Gly Asp Pro Leu Arg Val
                20                  25                  30

Ile Ile Leu Val Ala Gly Ala Phe Phe Trp Leu Val Ser Leu Leu Leu
                35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
                100                 105                 110

Ser Ile Arg Gln Met Ala Tyr Val Ser Gly Leu Ser Phe Gly Ile Ile
            115                 120                 125

Ser Gly Val Phe Ser Val Ile Ser Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
                180                 185                 190

Val Val Gly Ser His Leu Leu Thr Ser Gly Leu Thr Phe Leu Asn Pro
            195                 200                 205

Trp Tyr Glu Ala Ser Leu Leu Pro Ile Tyr Ala Val Thr Val Ser Met
        210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
```

<210> SEQ ID NO 39
<211> LENGTH: 131
<212> TYPE: PRT
<213> ORGANISM: Homo sapiens

<400> SEQUENCE: 39

Met Ala Tyr Val Ser Gly Leu Ser Phe Gly Ile Ile Ser Gly Val Phe
1               5                   10                  15

Ser Val Ile Asn Ile Leu Ala Asp Ala Leu Gly Pro Gly Val Val Gly
            20                  25                  30

Ile His Gly Asp Ser Pro Tyr Tyr Phe Leu Thr Ser Ala Phe Leu Thr
        35                  40                  45

Ala Ala Ile Ile Leu Leu His Thr Phe Trp Gly Val Val Phe Phe Asp
    50                  55                  60

Ala Cys Glu Arg Arg Tyr Trp Ala Leu Gly Leu Val Val Gly Ser
65                  70                  75                  80

His Leu Leu Thr Ser Gly Leu Thr Phe Leu Asn Pro Trp Tyr Glu Ala
                85                  90                  95

Ser Leu Leu Pro Ile Tyr Ala Val Thr Val Ser Met Gly Leu Trp Ala
            100                 105                 110

Phe Ile Thr Ala Gly Gly Ser Leu Arg Ser Ile Gln Arg Ser Leu Leu
        115                 120                 125

Cys Lys Asp
    130

<210> SEQ ID NO 40
<211> LENGTH: 195
<212> TYPE: PRT
<213> ORGANISM: Homo sapiens

<400> SEQUENCE: 40

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Arg Cys Ser Ala Leu Pro Thr Thr Ser Cys
        35                  40                  45

Leu Ile Ser Gly Leu Ser Phe Gly Ile Ile Ser Gly Val Phe Ser Val
    50                  55                  60

Ile Asn Ile Leu Ala Asp Ala Leu Gly Pro Gly Val Val Gly Ile His
65                  70                  75                  80

Gly Asp Ser Pro Tyr Tyr Phe Leu Thr Ser Ala Phe Leu Thr Ala Ala
                85                  90                  95

Ile Ile Leu Leu His Thr Phe Trp Gly Val Val Phe Asp Ala Cys
            100                 105                 110

Glu Arg Arg Arg Tyr Trp Ala Leu Gly Leu Val Val Gly Ser His Leu
        115                 120                 125

Leu Thr Ser Gly Leu Thr Phe Leu Asn Pro Trp Tyr Glu Ala Ser Leu
    130                 135                 140

Leu Pro Ile Tyr Ala Val Thr Val Ser Met Gly Leu Trp Ala Phe Ile
145                 150                 155                 160

Thr Ala Gly Gly Ser Leu Arg Ser Ile Gln Arg Ser Leu Leu Cys Arg
                165                 170                 175

Arg Gln Glu Asp Ser Arg Val Met Val Tyr Ser Ala Leu Arg Ile Pro

```
                180                 185                 190

Pro Glu Asp
        195

<210> SEQ ID NO 41
<211> LENGTH: 114
<212> TYPE: PRT
<213> ORGANISM: Homo sapiens

<400> SEQUENCE: 41

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Asn Phe
                85                  90                  95

Trp Ser Leu Leu Arg Tyr His Gln Trp Cys Leu Leu Cys Tyr Gln Tyr
            100                 105                 110

Phe Gly

<210> SEQ ID NO 42
<211> LENGTH: 190
<212> TYPE: PRT
<213> ORGANISM: Homo sapiens

<400> SEQUENCE: 42

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Lys Ala Asp Glu Gly Leu Ala Ser Leu Ser
        35                  40                  45

Glu Asp Gly Arg Ser Pro Ile Ser Ile Arg Gln Met Ala Tyr Val Ser
    50                  55                  60

Gly Leu Ser Phe Gly Ile Ile Ser Gly Val Phe Ser Val Ile Asn Ile
65                  70                  75                  80

Leu Ala Asp Ala Leu Gly Pro Gly Val Val Gly Ile His Gly Asp Ser
                85                  90                  95

Pro Tyr Tyr Phe Leu Thr Ser Ala Phe Leu Thr Ala Ala Ile Ile Leu
            100                 105                 110

Leu His Thr Phe Trp Gly Val Val Phe Phe Asp Ala Cys Glu Arg Arg
        115                 120                 125

Arg Tyr Trp Ala Leu Gly Leu Val Val Gly Ser His Leu Leu Thr Ser
    130                 135                 140

Gly Leu Thr Phe Leu Asn Pro Trp Tyr Glu Ala Ser Leu Leu Pro Ile
145                 150                 155                 160

Tyr Ala Val Thr Val Ser Met Gly Leu Trp Ala Phe Ile Thr Ala Gly
                165                 170                 175

Gly Ser Leu Arg Ser Ile Gln Arg Ser Leu Leu Cys Lys Asp
            180                 185                 190
```

<210> SEQ ID NO 43
<211> LENGTH: 247
<212> TYPE: PRT
<213> ORGANISM: Homo sapiens

<400> SEQUENCE: 43

```
Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
                245
```

<210> SEQ ID NO 44
<211> LENGTH: 265
<212> TYPE: PRT
<213> ORGANISM: Homo sapiens

<400> SEQUENCE: 44

```
Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80
```

```
Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Ser Leu Arg Ser Ile Gln
225                 230                 235                 240

Arg Ser Leu Leu Cys Arg Arg Gln Glu Asp Ser Arg Val Met Val Tyr
                245                 250                 255

Ser Ala Leu Arg Ile Pro Pro Glu Asp
                260                 265

<210> SEQ ID NO 45
<211> LENGTH: 247
<212> TYPE: PRT
<213> ORGANISM: Homo sapiens

<400> SEQUENCE: 45

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
                20                  25                  30

Ile Ile Leu Val Ala Gly Ala Phe Phe Trp Leu Val Ser Leu Leu Leu
            35                  40                  45

Ala Ser Val Val Trp Phe Ile Leu Val His Val Thr Asp Arg Ser Asp
        50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
```

```
                    180                 185                 190
Val Val Gly Ser His Leu Leu Thr Ser Gly Leu Thr Phe Leu Asn Pro
            195                 200                 205

Trp Tyr Glu Ala Ser Leu Leu Pro Ile Tyr Ala Val Thr Val Ser Met
210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
                245

<210> SEQ ID NO 46
<211> LENGTH: 265
<212> TYPE: PRT
<213> ORGANISM: Homo sapiens

<400> SEQUENCE: 46

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
210                 215                 220

Gly Leu Trp Ala Phe Ile Thr Ala Gly Gly Ser Leu Arg Ser Ile Gln
225                 230                 235                 240

Arg Ser Leu Leu Cys Arg Arg Gln Glu Asp Ser Arg Val Met Val Tyr
                245                 250                 255

Ser Ala Leu Arg Ile Pro Pro Glu Asp
            260                 265

<210> SEQ ID NO 47
<211> LENGTH: 247
<212> TYPE: PRT
<213> ORGANISM: Homo sapiens
```

<400> SEQUENCE: 47

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
            85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
            115                 120                 125

Ser Gly Val Phe Ser Val Ile Asn Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
                245

<210> SEQ ID NO 48
<211> LENGTH: 265
<212> TYPE: PRT
<213> ORGANISM: Homo sapiens

<400> SEQUENCE: 48

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
            85                  90                  95

Ala Asp Glu Gly Leu Ala Ser Leu Ser Glu Asp Gly Arg Ser Pro Ile
            100                 105                 110

```
Ser Ile Arg Gln Met Ala Tyr Val Ser Gly Leu Ser Phe Gly Ile Ile
            115                 120                 125

Ser Gly Val Phe Ser Val Ile Asn Ile Leu Ala Asp Ala Leu Gly Pro
        130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Ile Arg Ser Ile Gln
225                 230                 235                 240

Arg Ser Leu Leu Cys Arg Arg Gln Glu Asp Ser Arg Val Met Val Tyr
                245                 250                 255

Ser Ala Leu Arg Ile Pro Pro Glu Asp
                260                 265

<210> SEQ ID NO 49
<211> LENGTH: 247
<212> TYPE: PRT
<213> ORGANISM: Homo sapiens

<400> SEQUENCE: 49

Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
                20                  25                  30

Ile Ile Leu Val Ala Gly Ala Phe Phe Trp Leu Val Ser Leu Leu Leu
            35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
                100                 105                 110

Ser Ile Arg Gln Met Ala Tyr Val Ser Gly Leu Ser Phe Gly Ile Ile
            115                 120                 125

Ser Gly Val Phe Ser Val Ile Asn Ile Leu Ala Asp Ala Leu Gly Pro
        130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220
```

```
Gly Leu Trp Ala Phe Ile Thr Ala Gly Gly Ser Leu Arg Ser Ile Gln
225                 230                 235                 240

Arg Ser Leu Leu Cys Lys Asp
                245
```

<210> SEQ ID NO 50
<211> LENGTH: 247
<212> TYPE: PRT
<213> ORGANISM: Homo sapiens

<400> SEQUENCE: 50

```
Met Gly Ala Ala Val Phe Phe Gly Cys Thr Phe Val Ala Phe Gly Pro
1               5                   10                  15

Ala Phe Ala Leu Phe Leu Ile Thr Val Ala Gly Asp Pro Leu Arg Val
            20                  25                  30

Ile Ile Leu Val Ala Gly Ala Phe Phe Trp Leu Val Ser Leu Leu Leu
        35                  40                  45

Ala Ser Val Val Trp Phe Ile Leu Val His Val Thr Asp Arg Ser Asp
    50                  55                  60

Ala Arg Leu Gln Tyr Gly Leu Leu Ile Phe Gly Ala Ala Val Ser Val
65                  70                  75                  80

Leu Leu Gln Glu Val Phe Arg Phe Ala Tyr Tyr Lys Leu Leu Lys Lys
                85                  90                  95

Ala Asp Glu Gly Leu Ala Ser Leu Ser Glu Asp Gly Arg Ser Pro Ile
            100                 105                 110

Ser Ile Arg Gln Met Ala Tyr Val Ser Gly Leu Ser Phe Gly Ile Ile
        115                 120                 125

Ser Gly Val Phe Ser Val Ile Asn Ile Leu Ala Asp Ala Leu Gly Pro
    130                 135                 140

Gly Val Val Gly Ile His Gly Asp Ser Pro Tyr Tyr Phe Leu Thr Ser
145                 150                 155                 160

Ala Phe Leu Thr Ala Ala Ile Ile Leu Leu His Thr Phe Trp Gly Val
                165                 170                 175

Val Phe Phe Asp Ala Cys Glu Arg Arg Arg Tyr Trp Ala Leu Gly Leu
            180                 185                 190

Val Val Gly Ser His Leu Leu Thr Ser Gly Leu Thr Phe Leu Asn Pro
        195                 200                 205

Trp Tyr Glu Ala Ser Leu Leu Pro Ile Tyr Ala Val Thr Val Ser Met
    210                 215                 220

Gly Leu Trp Ala Phe Ile Thr Ala Gly Gly Ser Leu Arg Ser Ile Gln
225                 230                 235                 240

Arg Ser Leu Leu Cys Lys Asp
                245
```

<210> SEQ ID NO 51
<211> LENGTH: 257
<212> TYPE: PRT
<213> ORGANISM: Homo sapiens

<400> SEQUENCE: 51

```
Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45
```

Ser Ser Leu Val Trp Phe Met Ala Arg Val Ile Ile Asp Asn Lys Asp
        50                      55                      60

Gly Pro Thr Gln Lys Tyr Leu Leu Ile Phe Gly Ala Phe Val Ser Val
65                      70                      75                      80

Tyr Ile Gln Glu Met Phe Arg Phe Ala Tyr Tyr Lys Leu Leu Lys Lys
                        85                      90                      95

Ala Ser Glu Gly Leu Lys Ser Ile Asn Pro Gly Glu Thr Ala Pro Ser
                100                     105                     110

Met Arg Leu Leu Ala Tyr Val Ser Gly Leu Gly Phe Gly Ile Met Ser
                115                     120                     125

Gly Val Phe Ser Phe Val Asn Thr Leu Ser Asp Ser Leu Gly Pro Gly
                130                     135                     140

Thr Val Gly Ile His Gly Asp Ser Pro Gln Phe Phe Leu Tyr Ser Ala
145                     150                     155                     160

Phe Met Thr Leu Val Ile Ile Leu Leu His Val Phe Trp Gly Ile Val
                165                     170                     175

Phe Phe Asp Gly Cys Glu Lys Lys Lys Trp Gly Ile Leu Leu Ile Val
                180                     185                     190

Leu Leu Thr His Leu Leu Val Ser Ala Gln Thr Phe Ile Ser Ser Tyr
                195                     200                     205

Tyr Gly Ile Asn Leu Ala Ser Ala Phe Ile Ile Leu Val Leu Met Gly
                210                     215                     220

Thr Trp Ala Phe Leu Ala Ala Gly Gly Ser Cys Arg Ser Leu Lys Leu
225                     230                     235                     240

Cys Leu Leu Cys Gln Asp Lys Asn Phe Leu Leu Tyr Asn Gln Arg Ser
                245                     250                     255

Arg

<210> SEQ ID NO 52
<211> LENGTH: 216
<212> TYPE: PRT
<213> ORGANISM: Homo sapiens

<400> SEQUENCE: 52

Met Thr Ala Ala Val Phe Phe Gly Cys Ala Phe Ile Ala Phe Gly Pro
1               5                       10                      15

Ala Leu Ala Leu Tyr Val Phe Thr Ile Ala Thr Glu Pro Leu Arg Ile
                20                      25                      30

Ile Phe Leu Ile Ala Gly Ala Phe Phe Trp Leu Val Ser Leu Leu Ile
                35                      40                      45

Ser Ser Leu Val Trp Phe Met Ala Arg Val Ile Ile Asp Asn Lys Asp
        50                      55                      60

Gly Pro Thr Gln Lys Tyr Leu Leu Ile Phe Gly Ala Phe Val Ser Val
65                      70                      75                      80

Tyr Ile Gln Glu Met Phe Arg Phe Ala Tyr Tyr Lys Leu Leu Lys Lys
                85                      90                      95

Ala Ser Glu Gly Leu Lys Ser Ile Asn Pro Gly Glu Thr Ala Pro Ser
                100                     105                     110

Met Arg Leu Leu Ala Tyr Ala Phe Met Thr Leu Val Ile Ile Leu Leu
                115                     120                     125

His Val Phe Trp Gly Ile Val Phe Phe Asp Gly Cys Glu Lys Lys Lys
                130                     135                     140

Trp Gly Ile Leu Leu Ile Val Leu Leu Thr His Leu Leu Val Ser Ala
145                     150                     155                     160

```
Gln Thr Phe Ile Ser Ser Tyr Gly Ile Asn Leu Ala Ser Ala Phe
                165                 170                 175

Ile Ile Leu Val Leu Met Gly Thr Trp Ala Phe Leu Ala Ala Gly Gly
            180                 185                 190

Ser Cys Arg Ser Leu Lys Leu Cys Leu Leu Cys Gln Asp Lys Asn Phe
        195                 200                 205

Leu Leu Tyr Asn Gln Arg Ser Arg
    210                 215

<210> SEQ ID NO 53
<211> LENGTH: 81
<212> TYPE: PRT
<213> ORGANISM: Homo sapiens

<400> SEQUENCE: 53

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Arg Arg Val Glu Thr Cys Lys Asn Thr Glu
        35                  40                  45

Ala Pro Asp Cys Ala Ser Pro Ser Gly Ser Leu Ser Phe Leu Leu Val
    50                  55                  60

Gly Val Ser Thr Asp Phe Val Pro Cys Leu Val His Gly Lys Ser His
65                  70                  75                  80

Tyr

<210> SEQ ID NO 54
<211> LENGTH: 257
<212> TYPE: PRT
<213> ORGANISM: Homo sapiens

<400> SEQUENCE: 54

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Arg Glu Met Phe Arg Phe Ala Tyr Tyr Lys Leu Leu Lys Lys
            85                  90                  95

Ala Ser Glu Gly Leu Lys Ser Ile Asn Pro Gly Glu Thr Ala Pro Ser
        100                 105                 110

Met Arg Leu Leu Ala Tyr Val Ser Gly Leu Gly Phe Gly Ile Met Ser
    115                 120                 125

Gly Val Phe Ser Phe Val Asn Thr Leu Ser Asp Ser Leu Gly Pro Gly
130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
            165                 170                 175
```

```
Phe Phe Asp Gly Cys Glu Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Leu Tyr Asn Gln Arg Ser
                245                 250                 255

Arg

<210> SEQ ID NO 55
<211> LENGTH: 257
<212> TYPE: PRT
<213> ORGANISM: Homo sapiens

<400> SEQUENCE: 55

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Gln Glu Met Phe Arg Phe Ala Tyr Tyr Lys Leu Leu Lys Lys
                85                  90                  95

Ala Ser Glu Gly Leu Lys Ser Ile Asn Pro Gly Glu Thr Ala Pro Ser
            100                 105                 110

Met Arg Leu Leu Ala Tyr Val Ser Gly Leu Gly Phe Gly Ile Met Ser
        115                 120                 125

Gly Val Phe Ser Phe Val Asn Thr Leu Ser Asp Ser Leu Gly Pro Gly
    130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Leu Tyr Asn Gln Arg Ser
                245                 250                 255

Arg

<210> SEQ ID NO 56
<211> LENGTH: 257
<212> TYPE: PRT
```

-continued

<213> ORGANISM: Homo sapiens

<400> SEQUENCE: 56

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Arg Glu Met Phe Arg Phe Ala Tyr Tyr Lys Leu Leu Lys Lys
                85                  90                  95

Ala Ser Glu Gly Leu Lys Ser Ile Asn Pro Gly Glu Thr Ala Pro Ser
            100                 105                 110

Met Arg Leu Leu Ala Tyr Val Ser Gly Leu Gly Phe Gly Ile Met Ser
        115                 120                 125

Gly Val Phe Ser Phe Val Asn Thr Leu Ser Asp Ser Leu Gly Pro Gly
130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Tyr Asn Gln Arg Ser
                245                 250                 255

Arg

<210> SEQ ID NO 57
<211> LENGTH: 257
<212> TYPE: PRT
<213> ORGANISM: Homo sapiens

<400> SEQUENCE: 57

Met Thr Ala Ala Val Phe Phe Gly Cys Ala Phe Ile Ala Phe Gly Pro
1               5                   10                  15

Ala Leu Ala Leu Tyr Val Phe Thr Ile Ala Ile Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Gln Glu Met Phe Arg Phe Ala Tyr Tyr Lys Leu Leu Lys Lys
                85                  90                  95

```
Ala Ser Glu Gly Leu Lys Ser Ile Asn Pro Gly Glu Thr Ala Pro Ser
                100                 105                 110

Met Arg Leu Leu Ala Tyr Val Ser Gly Leu Gly Phe Gly Ile Met Ser
            115                 120                 125

Gly Val Phe Ser Phe Val Asn Thr Leu Ser Asp Ser Leu Gly Pro Gly
        130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Tyr Asn Gln Arg Ser
                245                 250                 255

Arg

<210> SEQ ID NO 58
<211> LENGTH: 257
<212> TYPE: PRT
<213> ORGANISM: Homo sapiens

<400> SEQUENCE: 58

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Phe Trp Leu Val Ser Leu Leu Ile
        35                  40                  45

Ser Ser Leu Val Trp Phe Met Ala Arg Val Ile Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Gln Glu Met Phe Arg Phe Ala Tyr Tyr Lys Leu Leu Lys Lys
                85                  90                  95

Ala Ser Glu Gly Leu Lys Ser Ile Asn Pro Gly Glu Thr Ala Pro Ser
                100                 105                 110

Met Arg Leu Leu Ala Tyr Val Ser Gly Leu Gly Phe Gly Ile Met Ser
            115                 120                 125

Gly Val Phe Ser Phe Val Asn Thr Leu Ser Asp Ser Leu Gly Pro Gly
        130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205
```

```
Tyr Gly Ile Asn Leu Ala Ser Ala Phe Ile Ile Leu Val Leu Met Gly
        210             215                 220

Thr Trp Ala Phe Leu Ala Ala Gly Gly Ser Cys Arg Ser Leu Lys Leu
225             230             235                 240

Cys Leu Leu Cys Gln Asp Lys Asn Phe Leu Leu Tyr Asn Gln Arg Ser
                245             250             255

Arg

<210> SEQ ID NO 59
<211> LENGTH: 21
<212> TYPE: DNA
<213> ORGANISM: Rattus norvegicus

<400> SEQUENCE: 59
ctccttccac aatcggtatt a                                        21
```

GAMMA-SECRETASE INHIBITION REDUCE APOC3 LEVELS AND PLASMA TRIGLYCERIDES

CROSS-REFERENCE TO RELATED APPLICATIONS

This application is a § 371 national stage of PCT International Application No. PCT/US2015/014481, filed Feb. 5, 2015, claiming the benefit of U.S. Provisional Application Nos. 62/032,324, filed Aug. 5, 2014, and 61/936,279, filed Feb. 5, 2014, the contents of each of which are hereby incorporated by reference in its entirety.

This invention was made with government support under grant number DK093604 awarded by the National Institutes of Health. The U.S. government has certain rights in the invention.

REFERENCE TO A SEQUENCE LISTING

This application incorporates by reference nucleotide and/or amino acid sequences which are present in the file named "180411 86108-A-PCT-US Substitute Sequence Listing AWS.txt" which is 164 kilobytes in size, and which was created Apr. 11, 2018 in the IBM-PC machine format, having an operating system compatibility with MS-Windows, which is contained in the text file filed on Apr. 11, 2018.

All publications and other references mentioned herein are incorporated by reference in their entirety, as if each individual publication or reference were specifically and individually indicated to be incorporated by reference. Publications and references cited herein are not admitted to be prior art.

BACKGROUND OF THE INVENTION

Obesity has reached epidemic status in the United States. The Centers for Disease Control has stated that more than ⅓ of American adults are obese, and estimated the medical costs attributable to obesity at $147 billion in 2008, a number that is likely to be significantly higher today and in the future. One of the core components of obesity-induced metabolic syndrome is excess plasma triglycerides. Elevated plasma triglyceride level, or hypertriglyceridemia, is an independent risk factor for coronary heart disease, above and beyond other obesity-related complications (e.g., high LDL cholesterol, low HDL cholesterol and Type 2 Diabetes). Many patients are unable to get to plasma triglyceride targets with currently available therapies.

Thus, new therapies for reducing plasma triglycerides are needed.

SUMMARY OF THE INVENTION

The invention provides a method of reducing a subject's plasma triglyceride level, comprising administering to a subject in need thereof a gamma-secretase inhibitor in an amount effective to reduce the subject's plasma triglyceride level.

The invention also provides a method of treating a subject afflicted with hypertriglyceridemia, comprising administering to the subject a gamma-secretase inhibitor in an amount effective to treat the subject.

The invention also provides a method of reducing a subject's plasma glucose level, comprising administering to a subject in need thereof a gamma-secretase inhibitor in an amount effective to reduce the subject's glucose level.

The invention also provides a method of reducing a subject's ApoC3 level, comprising administering to a subject in need thereof a gamma-secretase inhibitor in an amount effective to reduce the subject's ApoC3 level.

DETAILED DESCRIPTION OF THE INVENTION

Figure 1:
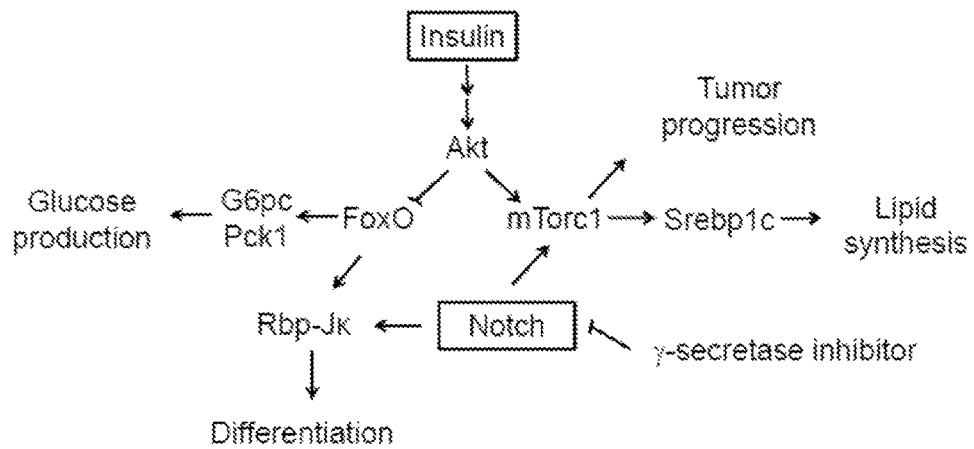
FIG. 1: Bifurcation model of hepatic insulin signaling illustrating how reduction in Notch signaling with γ-secretase inhibitor (GSI) treatment blocks mTorc1 activation, and tumorigenesis.

The invention provides a method of reducing a subject's plasma triglyceride level, comprising administering to a subject in need thereof a gamma-secretase inhibitor in an amount effective to reduce the subject's plasma triglyceride level.

The invention also provides a method of treating a subject afflicted with hypertriglyceridemia, comprising administering to the subject a gamma-secretase inhibitor in an amount effective to treat the subject.

In some embodiments, the administration reduces the triglyceride level in the subject's very low-density lipoprotein (VLDL) plasma fraction.

In some embodiments, the administration reduces the subject's plasma triglyceride level and apolipoprotein C3 (ApoC3) level.

In some embodiments, the administration reduces the subject's plasma triglyceride level and serum apolipoprotein C3 (ApoC3) level.

In some embodiments, the administration reduces the subject's serum triglyceride level.

In some embodiments, the administration reduces the triglyceride level in the subject's very low-density lipoprotein (VLDL) serum fraction.

In some embodiments, the administration reduces the subject's serum triglyceride level and apolipoprotein C3 (ApoC3) level.

In some embodiments, the administration reduces the subject's serum triglyceride level and serum apolipoprotein C3 (ApoC3) level.

The invention also provides a method of reducing a subject's ApoC3 level, comprising administering to a subject in need thereof a gamma-secretase inhibitor in an amount effective to reduce the subject's ApoC3 level.

In some embodiments, the administration reduces the subject's hepatic ApoC3 level.

In some embodiments, the administration reduces the subject's plasma ApoC3 level.

In some embodiments, the administration reduces the subject's serum ApoC3 level.

In some embodiments, the administration reduces the ApoC3 level in the subject's HDL or VLDL serum fraction.

In some embodiments, the administration reduces the ApoC3 level in the subject's VLDL serum fraction.

In some embodiments, the administration reduces the subject's serum ApoC3 level and serum triglyceride level.

The invention also provides a method of reducing a subject's plasma glucose level, comprising administering to a subject in need thereof a gamma-secretase inhibitor in an amount effective to reduce the subject's glucose level.

In some embodiments, the administration of the gamma-secretase inhibitor inhibits whole-body gamma-secretase.

In some embodiments, the administration of the gamma-secretase inhibitor inhibits liver gamma-secretase without significantly inhibiting gamma-secretase elsewhere in the subject.

In an embodiment, administration of the gamma-secretase inhibitor inhibits liver gamma-secretase without significantly inhibiting whole-body gamma-secretase.

In some embodiments, the administration of the gamma-secretase inhibitor targets the gamma-secretase inhibitor to the liver.

In some embodiments, the administration of the gamma-secretase inhibitor targets the gamma-secretase inhibitor to hepatocytes.

In some embodiments, the gamma-secretase inhibitor is (i) coupled to a ligand molecule targeted to a receptor on a hepatic cell, or (ii) administered by a bio-nanocapsule.

In some embodiments, the gastrointestinal Notch inhibition is substantially uninhibited.

In some embodiments, the gamma-secretase inhibitor is a small molecule inhibitor, an antisense oligonucleotide, or an adenoviral vector.

In some embodiments, the gamma-secretase inhibitor is a small molecule inhibitor, an oligonucleotide or an adenoviral vector.

In some embodiments, the gamma-secretase inhibitor is an oligonucleotide.

In some embodiments, the oligonucleotide is an antisense oligonucleotide, an RNA-interference inducing compound, or a ribozyme.

In some embodiments, the oligonucleotide is targeted to hepatocytes.

In some embodiments, the oligonucleotide comprises 1, 2, 3, 4, or 5 or more stretches of nucleotides in a sequence that is complementary to nicastrin-encoding mRNA, presenilin 1-encoding mRNA and presenilin 2-encoding mRNA, or APH1A-encoding mRNA and APH1B-encoding mRNA, wherein each stretch of complementary contiguous nucleotides is at least at least 4, 5, 6, 7, 8, 9, 10, 11, 12, 13, 14, 15, 16, 17, 18, 19, 20, 21, 22, 23, 24, 25 or more nucleotides in length.

In some embodiments, the oligonucleotide comprises 1, 2, 3, 4, or 5 or more stretches of nucleotides in a sequence that is complementary to nicastrin-encoding mRNA, presenilin 1-encoding mRNA, presenilin 2-encoding mRNA, APH1A-encoding mRNA, or APH1B-encoding mRNA, wherein each stretch of complementary contiguous nucleotides is at least at least 4, 5, 6, 7, 8, 9, 10, 11, 12, 13, 14, 15, 16, 17, 18, 19, 20, 21, 22, 23, 24, 25 or more nucleotides in length.

In some embodiments, the oligonucleotide is modified to increase its stability in vivo.

In some embodiments, the small molecule inhibitor is 804929097, PF-3084014, BMS-708163, LY450139, or MK-0752.

In some embodiments, the gamma-secretase inhibitor is a small molecule inhibitor.

In some embodiments, the small molecule inhibitor is 2,2-dimethyl-N—((S)-6-oxo-6,7-dihydro-5H-dibenzo[b,d]azepin-7-yl)-N'-(2,2,3,3,3-pentafluoro-propyl)-malonamide, (S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide, bis(fluoroalkyl)-1,4-benzodiazepinone, (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide, cis-3-[4-[(4-chlorophenyl)sulfonyl]-4-(2,5-difluorophenyl) cyclohexyl]propanoic acid, dual anti-platelet study, bis(fluoroalkyl)-1,4-benzodiazepinone, or N-[(1S)-2-[[(7S)-6,7-dihydro-5-methyl-6-oxo-5H-dibenz[b,d]azepin-7-yl]

amino]-1-methyl-2-oxoethyl]-3,5-difluoro-benzeneacetamide.

In some embodiments, the subject is obese.

In some embodiments, the subject has hypertriglyceridemia.

In some embodiments, the hypertriglyceridemia is obesity-induced hypertriglyceridemia.

In some embodiments, the subject has fatty liver disease.

In some embodiments, the subject has non-alcoholic fatty liver disease.

In some embodiments, the subject has atherosclerosis.

In some embodiments, the subject has coronary heart disease.

In some embodiments, the subject has diabetes.

In some embodiments, the subject has Type 2 Diabetes.

In some embodiments, the subject is a human.

In some embodiments, the subject's plasma triglyceride level is >150 mg/dL.

In some embodiments, the subject's plasma triglyceride level is >500 mg/dL, about 200 to 499 mg/dL, or about 150 to 199 mg/dL.

In some embodiments, the subject's plasma triglyceride level is reduced by at least 20%, at least 25%, at least 30%, at least 35%, at least 40%, at least 45%, at least 50%, at least 55%, at least 60%, at least 65%, at least 70%, or at least 75%, relative to the level prior to administration of the gamma-secretase inhibitor.

In some embodiments, the subject's serum triglyceride level is reduced by at least 20%, at least 25%, at least 30%, at least 35%, at least 40%, at least 45%, at least 50%, at least 55%, at least 60%, at least 65%, at least 70%, or at least 75%, relative to the level prior to administration of the gamma-secretase inhibitor.

In some embodiments, the subject's glucose level while fasting is >100 mg/dL.

In some embodiments, the subject's glucose level two hours after eating is >140 mg/dL.

In some embodiments, the subject's plasma triglyceride level is reduced by at least 5%, at least 10%, at least 15%, at least 20%, or at least 25%, relative to the level prior to administration of the gamma-secretase inhibitor.

In some embodiments, the subject's serum triglyceride level is reduced by at least 5%, at least 10%, at least 15%, at least 20%, or at least 25%, relative to the level prior to administration of the gamma-secretase inhibitor.

Each embodiment disclosed herein is contemplated as being applicable to each of the other disclosed embodiments. Thus, all combinations of the various elements described herein are within the scope of the invention.

Unless otherwise defined, all technical and scientific terms used herein have the same meaning as commonly understood by a person of ordinary skill in the art to which this invention belongs.

TERMS

As used herein, "about" in the context of a numerical value or range means ±10% of the numerical value or range recited or claimed, unless the context requires a more limited range.

As used herein, "effective" when referring to an amount of a gamma-secretase inhibitor refers to the quantity of gamma-secretase inhibitor which is sufficient to yield a desired therapeutic response without undue adverse side effects (such as toxicity, irritation, or allergic response) commensurate with a reasonable benefit/risk ratio when used in the manner of this invention.

As used herein, "treating a subject afflicted with hypertriglyceridemia" encompasses, e.g., reducing the subject's plasma or serum triglyceride level to less than 500 mg/dL, less than 200 mg/dL or less than 150 mg/dL.

As used herein, "a subject in need thereof" encompasses, e.g., a subject with plasma or serum triglyceride level greater than 150 mg/dL, greater than 200 mg/dL, or to greater than 500 mg/dL.

As used herein, a "gamma-secretase inhibitor" is an agent which reduces in vivo activity of a gamma-secretase complex. A gamma-secretase inhibitor may be, e.g., a small molecule, an anti-sense oligonucleotide, or an adenoviral vector.

Methods of Inhibiting Gamma-Secretase

In some embodiments, each compound administered to the subject is, independently, an organic compound having a molecular weight less than 1000 Daltons, a DNA aptamer, an RNA aptamer, a polypeptide, an antibody, an oligonucleotide, an interfering RNA (RNAi) molecule, a ribozyme, or a small molecule inhibitor.

In some embodiments, a compound that is capable of inhibiting gamma-secretase is administered to the subject.

In some embodiments, the compound which is capable of inhibiting gamma-secretase is an organic compound having a molecular weight less than 1000 Daltons.

Small Molecule Inhibitor

A small molecule inhibitor may administered herein to inhibit activity of gamma-secretase.

As used herein, "RO4929097" refers to 2,2-dimethyl-N—((S)-6-oxo-6,7-dihydro-5H-dibenzo[b,d]azepin-7-yl)-N'-(2,2,3,3,3-pentafluoro-propyl)-malonamide. The CAS Registry Number for 804929097 is 847925-91-1. The structure of 804929097 is:

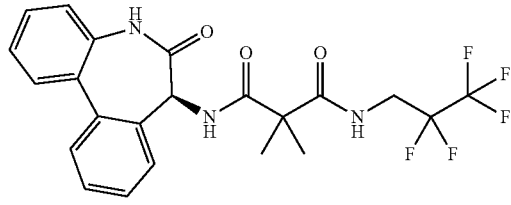 [SMILES: CC(C)(C(=O)NCC(F)(F)C(F)(F)F)C(=O)N[C@@H]1C(=O)Nc2ccccc2-c2ccccc21]

As used herein, "PF-3084014" refers to (S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide. The CAS Registry Number for PF-03084014 is 865773-15-5. The structure of PF-03084014 is:

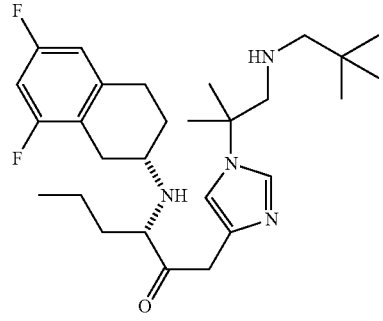

As used herein, "BMS-708163" refers to (R)-2-(4-chloro-N-(2-fluoro-4-(1,2,4-oxadiazol-3-yl)benzyl)phenylsulfonamido)-5,5,5-trifluoropentanamide. The CAS Registry Number for BMS-708163 is 1146699-66-2. The structure of BMS-708163 is:

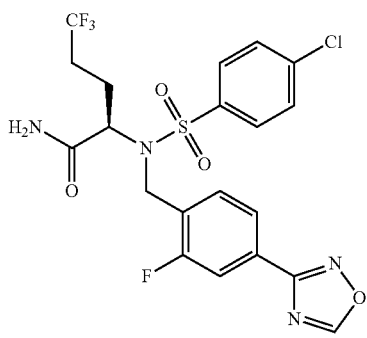 [SMILES: NC(=O)[C@@H](CCC(F)(F)F)N(Cc1ccc(-c2ncon2)cc1F)S(=O)(=O)c1ccc(Cl)cc1]

As used herein, "LY450139" refers to (2S)-2-hydroxy-3-methyl-N-(1S)-1-methyl-2-{[(1S)-3-methyl-2-oxo-2,3,4,5-tetrahydro-1H-3-benzazepin-1-yl]amino}-2-oxoethyl)butanamide. The CAS Registry Number for LY450139 is 425386-60-3. The structure of LY450139 is:

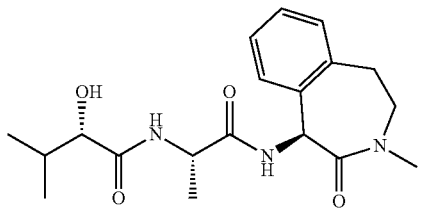 [SMILES: CC(C)[C@H](O)C(=O)N[C@@H](C)C(=O)N[C@@H]1C(=O)N(C)CCc2ccccc21]

As used herein, "MK-0752" refers to cis-3-[4-[(4-chlorophenyl)sulfonyl]-4-(2,5-difluorophenyl)cyclohexyl]propanoic acid. The CAS Registry Number for MK0752 is 471905-41-6. The structure of MK0752 is:

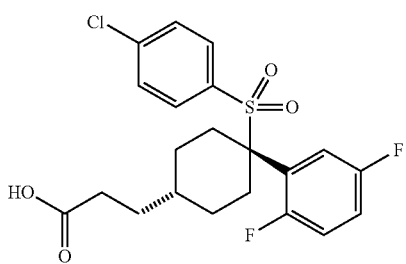

As used herein, dual anti-platelet study or "DAPT" refers to N—[N-(3,5-difluorophenacetyl)-1-alanyl]-S-phenylglycine t-butyl ester. The CAS Registry Number for DAPT is 208255-80-5. The structure of DAPT is:

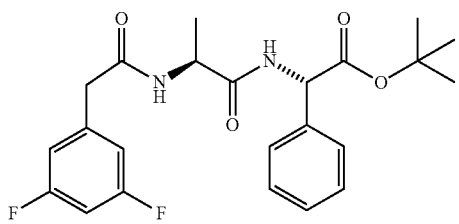

As used herein, "BMS-906024" refers to bis(fluoroalkyl)-1,4-benzodiazepinone. The CAS Registry Number for BMS-906024 is 1401066-79-2. The structure of BMS-906024 is:

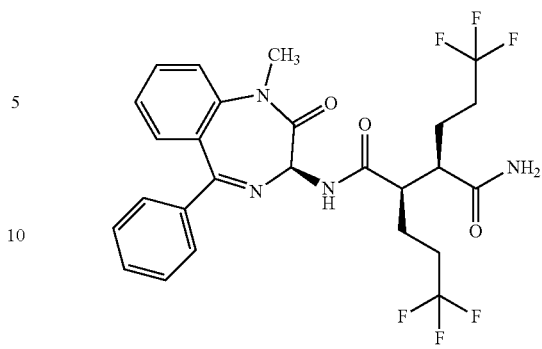

As used herein, dibenzazepine or "YO-01027", refers to N-[(1S)-2-[[(7S)-6,7-dihydro-5-methyl-6-oxo-5H-dibenz[b,d]azepin-7-yl]amino]-1-methyl-2-oxoethyl]-3,5-difluorobenzeneacetamide. The CAS Registry Number for dibenzazepine is 209984-56-5. The structure of dibenzazepine is:

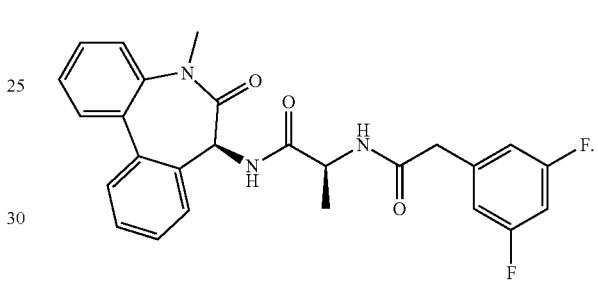

Non-limiting examples of gamma-secretase modulators which are described, for example, in the publication, Bergmans and Strooper, 2010, of which are hereby incorporated by reference in their entireties.

Non-limiting examples of gamma-secretase inhibitors which are described, for example, in the following publications: Andersson and Lendahl, 2014, Bergmans and De Strooper, 2010, Real et al., 2009, all of which are hereby incorporated by reference in their entireties.

Inhibiting Expression of Gamma-Secretase

In some embodiments, the compound which is capable of inhibiting gamma-secretase expression silences expression of a gene or silences transcription.

Oligonucleotide

Non-limiting examples of oligonucleotides capable of inhibition gamma-seretase expression include antisense oligonucleotides, ribozymes, and RNA interference molecules.

The amino acid sequence of nicastrin, NCSTN, is accessible in public databases by the GenBank accession number Q92542, and is set forth herein as SEQ ID NO: 1. The nucleotide sequence of NCSTN is also accessible in public databases by the GenBank accession number AF240468, and is set forth herein as SEQ ID NO: 2. The nucleotide sequence of NCSTN is also accessible in public databases by the GenBank accession number AK296153 and is set forth herein as SEQ ID NO: 3. The nucleotide sequence of NCSTN is also accessible in public databases by the GenBank accession number AK299142, and is set forth herein as SEQ ID NO: 4. The nucleotide sequence of NCSTN is also accessible in public databases by the GenBank accession number AK310741, and is set forth herein as SEQ ID NO: 5. The nucleotide sequence of NCSTN is also accessible in public databases by the GenBank accession number AK314764 and is set forth herein as SEQ ID NO: 6. The nucleotide sequence of NCSTN is also accessible in public databases by the accession number AY359120, and is set forth herein as SEQ ID NO: 7. The nucleotide sequence of NCSTN is also accessible in public databases by the Genbank accession number BC047621, and is set forth herein as SEQ ID NO: 8. The nucleotide sequence of NCSTN is also accessible in public databases by the GenBank accession number BC100024, and is set forth herein as SEQ ID NO: 9. The nucleotide sequence of NCSTN is also accessible in public databases by the GenBank accession number CN429672, and is set forth herein as SEQ ID NO: 10. The nucleotide sequence of nicastrin, NCSTN, is accessible in public databases by the GenBank accession number D87442, and is set forth herein as SEQ ID NO: 11.

The amino acid sequence of presenilin 1, PSEN1, is accessible in public databases by the GenBank accession number P49768, and is set forth herein as SEQ ID NO: 12. The amino acid sequence of PSEN1 is also accessible in public databases by the GenBank accession number AAL16811, and is set forth herein as SEQ ID NO: 13. The amino acid sequence which encodes NCSTN is accessible in public databases by the GenBank accession number CAA07825, and is set forth herein as SEQ ID NO: 14. The amino acid sequence of PSEN1 is also accessible in public databases by the GenBank accession number BAD96893, and is set forth herein as SEQ ID NO: 15. The amino acid sequence of PSEN1 is also accessible in public databases by the GenBank accession number BAH14071, and is set forth herein as SEQ ID NO: 16. The amino acid sequence which encodes PSEN1 is also accessible in public databases by the GenBank accession number BAG35430, and is set forth herein as SEQ ID NO: 17. The amino acid sequence which encodes PSEN1 is also accessible in public databases by the GenBank accession number AAH11729, and is set forth herein as SEQ ID NO: 18. The amino acid sequence which encodes PSEN1 is also accessible in public databases by the GenBank accession number AAB46416, and is set forth herein as SEQ ID NO 19. The amino acid sequence which encodes PSEN1 is also accessible in public databases by the GenBank accession number AAB46370, and is set forth herein as SEQ ID NO: 20. The amino acid sequence which encodes PSEN1 is also accessible in public databases by the GenBank accession number AAB05894, and is set forth herein as SEQ ID NO 21. The amino acid sequence which encodes PSEN1 is also accessible in public databases by the GenBank accession number AAB05895, and is set forth herein as SEQ ID NO: 22. The amino acid sequence which encodes PSEN1 is also accessible in public databases by the GenBank accession number CAA07825, and is set forth herein as SEQ ID NO: 23.

The amino acid sequence of presenilin 2, PSEN2, is accessible in public databases by the GenBank accession number P49810, and is set forth herein as SEQ ID NO: 24. The amino acid sequence of presenilin 2, PSEN2, is accessible in public databases by the GenBank accession number AAL16812, and is set forth herein as SEQ ID NO: 25. The amino acid sequence of PSEN2 is also accessible in public databases by the GenBank accession number BAF84988, and is set forth herein as SEQ ID NO: 26. The amino acid sequence of PSEN2 is also accessible in public databases by the GenBank accession number BAG62735, and is set forth herein as SEQ ID NO: 27. The amino acid sequence of PSEN2 is also accessible in public databases by the GenBank accession number AAH06365, and is set forth herein as SEQ ID NO: 28. The amino acid sequence of PSEN2 is also accessible in public, databases by the GenBank accession number AAP35630, and is set forth herein as SEQ ID NO: 29. The amino acid sequence of PSEN2 is also accessible in public databases by the GenBank accession number AAB59557, and is set forth herein as SEQ ID NO: 30. The amino acid sequence of PSEN2 is also accessible in public databases by the GenBank accession number AAC42012, and is set forth herein as SEQ ID NO: 31. The amino acid sequence of PSEN2 is also accessible in public databases by, the GenBank accession number AAC50290, and is set forth herein as SEQ ID NO: 32.

The amino acid sequence of APH1A gamma secretase subunit, APH1A, is accessible in public databases by the GenBank accession number Q96BI3, and is set forth herein as SEQ ID NO: 33. The amino acid sequence of APH1A is accessible in public databases by the GenBank accession number AAD34072, and is set forth herein as SEQ ID NO: 34. The amino acid sequence of APH1A is also accessible in public databases by the GenBank accession number AAN63816, and is set forth herein as SEQ ID NO: 35. The amino acid sequence of APH1A is also accessible in public databases by the GenBank accession number BAG51389, and is set forth herein as SEQ ID NO: 36. The amino acid sequence of APH1A is also accessible in public databases by the GenBank accession number BAC11529, and is set forth herein as SEQ ID NO: 37. The amino acid sequence of APH1A is also accessible in public databases by the GenBank accession number BAG52142, and is set forth herein as SEQ ID NO: 38. The amino acid sequence of APH1A is also accessible in public databases by the GenBank accession number BAG60040, and is set forth herein as SEQ ID NO: 39. The amino acid sequence of APH1A is also accessible in public databases by the GenBank accession number BAG60962, and is set forth herein as SEQ ID NO: 40. The amino acid sequence of APH1A is also accessible in public databases by the GenBank accession number BAG60993, and is set forth herein as SEQ ID NO: 41. The amino acid sequence of APH1A is also accessible in public databases by the GenBank accession number BAG62329, and is set forth herein as SEQ ID NO: 42. The amino acid sequence of APH1A is also accessible in public databases by the GenBank accession number CAE11677, and is set forth herein as SEQ ID NO: 43. The amino acid sequence of APH1A is also accessible in public databases by the GenBank accession number CAE11678, and is set forth herein as SEQ ID NO: 44. The amino acid sequence of APH1A is also accessible in public databases by the GenBank accession number AAM61955, and is set forth herein as SEQ ID NO: 45. The amino acid sequence of APH1A is also accessible in public databases by the GenBank accession number AAM61956, and is set forth herein as SEQ ID NO: 46. The amino acid sequence of APH1A is also accessible in public databases by the GenBank accession number AAQ89310, and is set forth herein as SEQ ID NO: 47. The amino acid sequence of APH1A is also accessible in public databases by the GenBank accession number AAH01230, and is set forth herein as SEQ ID NO: 48. The amino acid sequence of APH1A is also accessible in public databases by the GenBank accession number AAH08732, and is set forth herein as SEQ ID NO: 49. The amino acid sequence of APH1A is also accessible in public databases by the GenBank accession number AAH09501, and is set forth herein as SEQ ID NO: 50.

The amino acid sequence of APH1B gamma secretase subunit, APH1B, is accessible in public databases by the accession number Q8WW43, and is set forth herein as SEQ ID NO: 51. The amino acid sequence of APH1B is also accessible in public databases by the accession number BAD95573, and is net forth herein as SEQ ID NO: 52. The amino acid sequence of APH1B is also accessible in public databases by the accession number BAE02660, and is set forth herein as SEQ ID NO: 53. The amino acid sequence of APH1B is also accessible in public databases by the accession number AAN63817, and is set forth herein as SEQ ID NO: 54. The amino acid sequence of APH1B is also accessible in public databases by the accession number BAF83893, and is set forth herein as SEQ ID NO: 55. The amino acid sequence of APH1B is also accessible in public databases by the accession number CAB66606, and is set forth herein as SEQ ID NO: 56. The amino acid sequence of APH1B is also accessible in public databases by the accession number AAQ89061, and is set forth herein as SEQ ID NO: 57. The amino acid sequence of APH1B is also accessible in public databases by the accession number AAH20905, and is set forth herein as SEQ ID NO: 58.

In some embodiments, the compound which is capable of inhibiting gamma-secretase expression is an antisense oligonucleotide, a ribozyme, or an RNA interference molecule.

Antisense Oligonucleotide

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of target gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of gene expression can be obtained by designing antisense oligonucleotides which will form duplexes to the control, 5', or regulatory regions of the gene. Oligonucleotides derived from the transcription initiation site, e.g., between, positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (Nicholls et al., 1993, J Immunol Meth 165:81-91). An antisense oligonucleotide also can be designed to block translation of mRNA by preventing the transcript from binding to ribosomes.

Precise complementarity is not required for successful complex formation between an antisense oligonucleotide and the complementary sequence of a target polynucleotide. Antisense oligonucleotides which comprise, for example, 1, 2, 3, 4, or 5 or more stretches of contiguous nucleotides which are precisely complementary to a target polynucleotide, each separated by a stretch of contiguous nucleotides which are not complementary to adjacent nucleotides, can provide sufficient targeting specificity for a target mRNA. Preferably, each stretch of complementary contiguous nucleotides is at least 4, 5, 6, 7, 8, 9, 10, 11, 12, 13, 14, 15, 16, 17, 18, 19, 20, 21, 22, 23, 24, 25, or more nucleotides in length. Noncomplementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular target polynucleotide sequence. Antisense oligonucleotides can be modified without affecting their ability to hybridize to a target polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art.

Ribozymes

Ribozymes are RNA molecules with catalytic activity (Uhlmann et al., 1987, Tetrahedron. Lett. 215, 3539-3542). Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a polynucleotide can be used to generate ribozymes which will specifically bind to mRNA transcribed from the polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within an RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease target gene expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or VAS element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

RNA Interference

An interfering RNA (RNAi) molecule involves mRNA degradation. The use of RNAi has been described in Fire et al., 1998, Carthew et al., 2001, and Elbashir et al., 2001, the contents of which are incorporated herein by reference.

Interfering RNA or small inhibitory RNA (RNAi) molecules include short interfering RNAs (siRNAs), repeat-associated siRNAs (rasiRNAs), and micro-RNAs (miRNAs) in all stages of processing, including shRNAs, pri-miRNAs, and pre-miRNAs. These molecules have different origins: siRNAs are processed from double-stranded precursors (dsRNAs) with two distinct strands of base-paired RNA; siRNAs that are derived from repetitive sequences in the genome are called rasiRNAs; miRNAs are derived from a single transcript that forms base-paired hairpins. Base pairing of siRNAs and miRNAs can be perfect (i.e., fully complementary) or imperfect, including bulges in the duplex region.

Interfering RNA molecules encoded by recombinase-dependent transgenes of the invention can be based on existing shRNA, siRNA, piwi-interacting RNA (piRNA), micro RNA (miRNA), double-stranded RNA (dsRNA), anti-sense RNA, or any other RNA species that can be cleaved inside a cell to form interfering RNAs, with compatible modifications described herein.

As used herein, an "shRNA molecule" includes a conventional stem-loop shRNA, which forms a precursor miRNA (pre-miRNA). "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. When transcribed, a shRNA may form a primary miRNA (pri-miRNA) or a structure very similar to a natural pri-miRNA. The pri-miRNA is subsequently processed by Drosha and its cofactors into pre-miRNA. Therefore, the term "shRNA" includes pri-miRNA (shRNA-mir) molecules and pre-miRNA molecules.

A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches.

"RNAi-expressing construct" or "RNAi construct" is a generic term that includes nucleic acid preparations designed to achieve an RNA interference effect. An RNAi-expressing construct comprises an RNAi molecule that can be cleaved in vivo to form an siRNA or a mature shRNA. For example, an RNAi construct is an expression vector capable of giving rise to a siRNA or a mature shRNA in vivo. Non-limiting examples of vectors that may be used in accordance with the present invention are described herein and will be well known to a person having ordinary skill in the art. Exemplary methods of making and delivering long or short RNAi constructs can be found, for example, in WO01/68836 and WO01/75164.

RNAi is a powerful tool for in vitro and in vivo studies of gene function in mammalian cells and for therapy in both human and veterinary contexts. Inhibition of a target gene is sequence-specific in that gene sequences corresponding to a portion of the RNAi sequence, and the target gene itself, are specifically targeted for genetic inhibition. Multiple mechanisms of utilizing RNAi in mammalian cells have been described. The first is cytoplasmic delivery of siRNA molecules, which are either chemically synthesized or generated by DICER-digestion of dsRNA. These siRNAs are introduced into cells using standard transfection methods. The siRNAs enter the RISC to silence target mRNA expression.

Another mechanism is nuclear delivery, via viral vectors, of gene expression cassettes expressing a short hairpin RNA (shRNA). The shRNA is modeled on micro interfering RNA (miRNA), an endogenous trigger of the RNAi pathway (Lu et al., 2005, *Advances in Genetics* 54: 117-142, Fewell et al., 2006, *Drug Discovery Today* 11: 975-982). Conventional shRNAs, which mimic pre-miRNA, are transcribed by RNA Polymerase II or III as single-stranded molecules that form stem-loop structures. Once produced, they exit the nucleus, are cleaved by DICER, and enter the RISC as siRNAs.

Another mechanism is identical to the second mechanism, except that the shRNA is modeled on primary miRNA (shRNAmir), rather than pre-miRNA transcripts (Fewell et al., 2006). An example is the miR-30 miRNA construct. The use of this transcript produces a more physiological shRNA that reduces toxic effects.

The shRNAmir is first cleaved to produce shRNA, and then cleaved again by DICER to produce siRNA. The siRNA is then incorporated into the RISC for target mRNA degradation. However, aspects of the present invention relate to RNAi molecules that do not require DICER cleavage. See, e.g., U.S. Pat. No. 8,273,871, the entire contents of which are incorporated herein by reference.

For mRNA degradation, translational repression, or deadenylation, mature miRNAs or siRNAs are loaded into the RNA Induced Silencing Complex (RISC) by the RISC-loading complex (RLC). Subsequently, the guide strand leads the RISC to cognate target mRNAs in a sequence-specific manner and the Slicer component of RISC hydrolyses the phosphodiester bound coupling the target mRNA nucleotides paired to nucleotide 10 and 11 of the RNA guide strand. Slicer forms together with distinct classes of small RNAs the RNAi effector complex, which is the core of RISC. Therefore, the "guide strand" is that portion of the double-stranded RNA that associates with RISC, as opposed to the "passenger strand," which is not associated with RISC.

It is not necessary that there be perfect correspondence of the sequences, but the correspondence must be sufficient to enable the RNA to direct RNAi inhibition by cleavage or blocking expression of the target mRNA. In preferred RNA molecules, the number of nucleotides which is complementary to a target sequence is 16 to 29, 18 to 23, or 21-23, or 15, 16, 17, 18, 19, 20, 21, 22, 23, 24, or 25.

Isolated RNA molecules can mediate RNAi. That is, the isolated RNA molecules of the present invention mediate degradation or block expression of mRNA that is the transcriptional product of the gene. For convenience, such mRNA may also be referred to herein as mRNA to be degraded. The terms RNA, RNA molecule(s), RNA segment(s) and RNA fragment(s) may be used interchangeably to refer to RNA that mediates RNA interference. These terms include double-stranded RNA, small interfering RNA (siRNA), hairpin RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules are referred to as analogs or analogs of naturally-occurring RNA. RNA of the present invention need only be, sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA.

In some embodiments, an RNAi molecule of the invention is introduced into a mammalian cell in an amount sufficient to attenuate target gene expression in a sequence specific manner. The RNAi molecules of the invention can be introduced into the cell directly, or can be complexed with cationic lipids, packaged within liposomes, or otherwise delivered to the cell. In certain embodiments the RNAi molecule can be a synthetic RNAi molecule, including RNAi molecules incorporating modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or "locked nucleic acid" (LNA) modifications. In some embodiments, an RNAi molecule of the invention contains modified nucleotides that increase the stability or half-life of the RNAi molecule in vivo and/or in vitro. Alternatively, the RNAi molecule can comprise one or more aptamers, which interact(s) with a target of interest to form an aptamer:target complex. The aptamer can be at the 5' or the 3' end of the RNAi molecule. Aptamers can be developed through the SELEX screening process and chemically synthesized. An aptamer is generally chosen to preferentially bind to a target. Suitable targets include small organic molecules, polynucleotides, polypeptides, and proteins. Proteins can be cell surface proteins, extracellular proteins, membrane proteins, or serum proteins, such as albumin. Such target molecules may be internalized by a cell, thus effecting cellular uptake of the shRNA. Other potential targets include organelles, viruses, and cells.

As noted above, the RNA molecules of the present invention in general comprise an RNA portion and some additional portion, for example a deoxyribonucleotide portion. The total number of nucleotides in the RNA molecule is suitably less than in order to be effective mediators of RNAi. In preferred RNA molecules, the number of nucleotides is 16 to 29, more preferably 18 to 23, and most preferably 21-23.

Adenoviral Vector

An adenoviral vector encodes an oligonucleotide. The use of adenoviral vectors in gene therapy and tissue-specific targeting has been described in Beatty and Curiel, 2012, Barnett et al., 2002, and Rots et al., 2003, the contents of which are incorporated herein by reference.

Methods of Administration

"Administering" compounds in embodiments of the invention can be effected or performed using any of the various methods and delivery systems known to those skilled in the art. The administering can be, for example, intravenous, oral intramuscular, intravascular, intra-arterial, intracoronary, intramyocardial, intraperitoneal, and subcutaneous. Other non-limiting examples include topical administration, or coating of a device to be placed within the subject.

Injectable Drug Delivery

Injectable drug delivery systems may be employed in the methods described herein include solutions, suspensions, gels.

Oral Drug Delivery

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

For oral administration in liquid dosage form, a gamma-secretase inhibitor may be combined with any oral, non-toxic, pharmaceutically acceptable inert carrier such as ethanol, glycerol, water, and the like.

Naked Administration

The compounds used in embodiments of the present invention can be administered by naked administration.

Pharmaceutically Acceptable Carrier

The compounds used in embodiments of the present invention can be administered in a pharmaceutically acceptable carrier. As used herein, a "pharmaceutically acceptable carrier" is a pharmaceutically acceptable solvent, suspending agent or vehicle, for delivering the compounds to the subject. The carrier may be liquid or solid and is selected with the planned manner of administration in mind. Liposomes such as small unilamellar vesicles, large unilamallar vesicles, and multilamellar vesicles are also a pharmaceutically acceptable carrier. Liposomes can be formed from a variety of phospholipids, such as cholesterol, stearylamine, or phosphatidylcholines. The compounds may be administered as components of tissue-targeted emulsions. Examples of lipid carriers for antisense delivery are disclosed in U.S. Pat. Nos. 5,855,911 and 5,417,978, which are incorporated herein by reference. The compounds used in the methods of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

A compound of the invention can be administered in a mixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297, issued Sep. 2, 1975.

Tablets

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Specific Administration to Liver

Embodiments of the invention relate to specific administration to the liver or hepatocytes.

In some embodiments, a compound may specifically target the liver.

In some embodiments, a compound may specifically target hepatocytes.

In some embodiments, a compound may be specifically targeted to the liver by coupling the compound to ligand molecules, targeting the compound to a receptor on a hepatic cell, or administering the compound by a bio-nanocapsule.

A compound of the invention can also be administered by coupling of ligand molecules, such as coupling or targeting moieties on preformed nanocarriers, such as (PGA-PLA nanoparticles, PLGA nanoparticles, cyclic RGD-doxorubicin-nanoparticles, and poly(ethylene glycol)-coated biodegradable nanoparticles), by the post-insertion method, by the Avidin-Biotin complex, or before nanocarriers formulation, or by targeting receptors present on various hepatic cell, such as Asialoglycoproein receptor (ASGP-R), HDL-R, LDL-R, IgA-R, Scavenger R, Transferrin R, and Insulin R, as described in: Mishra et al., (2013) Efficient Hepatic Delivery of Drugs: Novel Strategies and Their Significance, BioMed Research International 2013: 382184, dx.doi.org/10.1155/2013/382184, the entire contents of which are incorporated herein by reference.

A compound of the invention can also be administered by bio-nanocapsule, as described in Yu et al., (2005) The Specific delivery of proteins to human liver cells by engineered bio-nanocapsules, FEES Journal 272:3651-3660, dx.doi.org/10.1111/j.1742-4658.2005.04790.x, the entire contents of which are incorporated herein by reference.

In some embodiments, an oligonucleotide specifically, targets the liver.

In some embodiments, an oligonucleotide specifically targets hepatocytes.

Antisense oligonucleotides of the invention can also be targeted to hepatocytes, as described in: Prakash et al., (2014) Targeted delivery of antisense oligonucleotides to hepatocytes using triantennary N-acetyl galactosamine improves potency 10-fold in mice, Nucleic Acids Research 42(13): 8796-8807, dx.doi.org/10.1093/nar/gku531, the entire contents which are incorporated herein by reference.

As used herein, the term "effective amount" refers to the quantity of a component that is sufficient to treat a subject without undue adverse side effects (such as toxicity, irritation, or allergic response) commensurate with a reasonable benefit/risk ratio when used in the manner of this invention, i.e. a therapeutically effective amount. The specific effective amount will vary with such factors as the particular condition being treated, the physical condition of the patient, the type of subject being treated, the duration of the treatment, the nature of concurrent therapy (if any), and the specific formulations employed and the structure of the compounds or its derivatives.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The dosage of a compound of the invention administered in treatment will vary depending upon factors such as the pharmacodynamic characteristics of the compound and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds of the invention may comprise a compound alone, or mixtures of a compound with additional compounds used to treat cancer. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the eye, all using dosage forms well known to those of ordinary skill in the pharmaceutical arts.

In an embodiment, the gamma-secretase inhibitor may be administered once a day, twice a day, every other day, once weekly, or twice weekly.

In an embodiment, 0.01 to 1000 mg of a gamma-secretase inhibitor is administered per administration.

A subject's triglyceride level may be expressed herein as plasma triglyceride or serum triglyceride.

A subject's apolipoprotein C3 (ApoC3) level may be expressed herein as plasma ApoC3 or serum ApoC3.

Where a range is given in the specification it is understood that the range includes all integers and 0.1 units within that range, and any sub-range thereof. For example, a range of 1 to 5 is a disclosure of 1.0, 1.1, 1.2, etc.

This invention will be better understood by reference to the Examples which follow, but those skilled in the art will readily appreciate that the specific experiments detailed are only illustrative of the invention as described more fully in the claims which follow thereafter.

EXAMPLE 1

Figure 2:
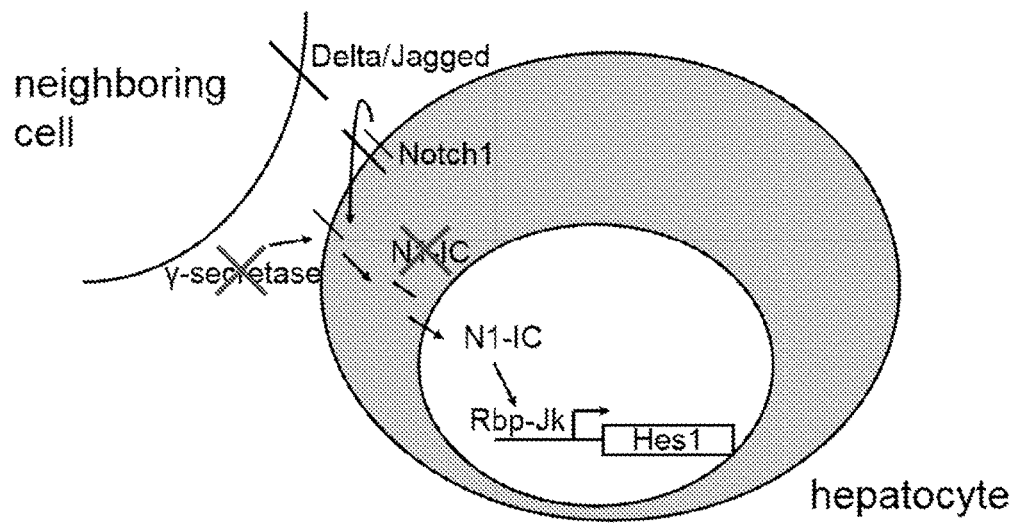
FIG. 2: Gamma-secretase inhibitors (GSIs) are pharmacologic inhibitors of Notch signaling.

Pharmacologic Notch Inhibition Decreases Blood Glucose in Lean and Obese Mice without Affecting Weight The Notch signaling pathway is a highly conserved cell signaling system present in most multicellular organisms. Notch signaling is well-established as critical for cell-cell communication and control of differentiation during normal development. Notch signaling is, frequently upregulated in tumors, and a variety of Notch inhibitors are in clinical development, some as advanced as Phase I/II trials, for cancer. Notch stimulates mTorc1 activity in T-cell leukemia, and reduction in Notch signaling with gamma-secretase inhibitor (GSI) treatment blocks mTorc1 activation, and tumorigenesis, as illustrated in FIG. 1. Gamma-secretase inhibitors (GSIs) are pharmacologic inhibitors of Notch signaling (FIG. 2).

There are interactions between Notch signaling and key metabolic mediators of obesity-related disease, and hepatic Notch signaling is elevated in mouse models and patients with Type 2 Diabetes (T2D) and non-alcoholic fatty liver disease (NAFLD). We hypothesized that Notch may reciprocally affect FoxO1- or mTorc1-dependent signaling, and thus carbon flux towards glucose and lipid production, and hypothesized that Notch inhibitors may be repurposed for treatment of diabetes and fatty liver disease.

Lean mice, diet induced obese (DIO) mice, and leptin-deficient obese (ob/ob) mice were administered either vehicle or GSI. GSI treatment decreased blood glucose in lean and obese mice without affecting weight as, shown in Table 1.

TABLE 1

Lean mice, diet induced obese (DIO) mice, and leptin-deficient obese (ob/ob) mice administered gamma secretase inhibitor (GSI), dibenzazepine (DBZ). Vehicle control for all experiments is normal saline containing 0.5% methoxycellulose/0.1% Tween-80.

| Cohort | Treatment | Weight (grams) | Glucose (mg/dl) | Insulin (ng/ml) |
|---|---|---|---|---|
| lean | vehicle | 22 ± 0.5 | 79 ± 4 | 0.45 ± 0.15 |
|  | GSI | 22 ± 0.6 | 64 ± 2*** | 0.49 ± 0.04 |
| DIO | vehicle | 34 ± 0.9 | 135 ± 12 | 1.62 ± 1.18 |
|  | GSI | 33 ± 0.7 | 72 ± 5*** | 1.33 ± 0.32 |
| ob/ob | vehicle | 49 ± 0.9 | 313 ± 33 | 23.2 ± 3.11 |
|  | GSI | 48 ± 0.9 | 98 ± 6*** | 15.6 ± 3.25* |

*$p < 0.05$
**$p < 0.01$
***$p < 0.001$ vs. vehicle

Figure 3:
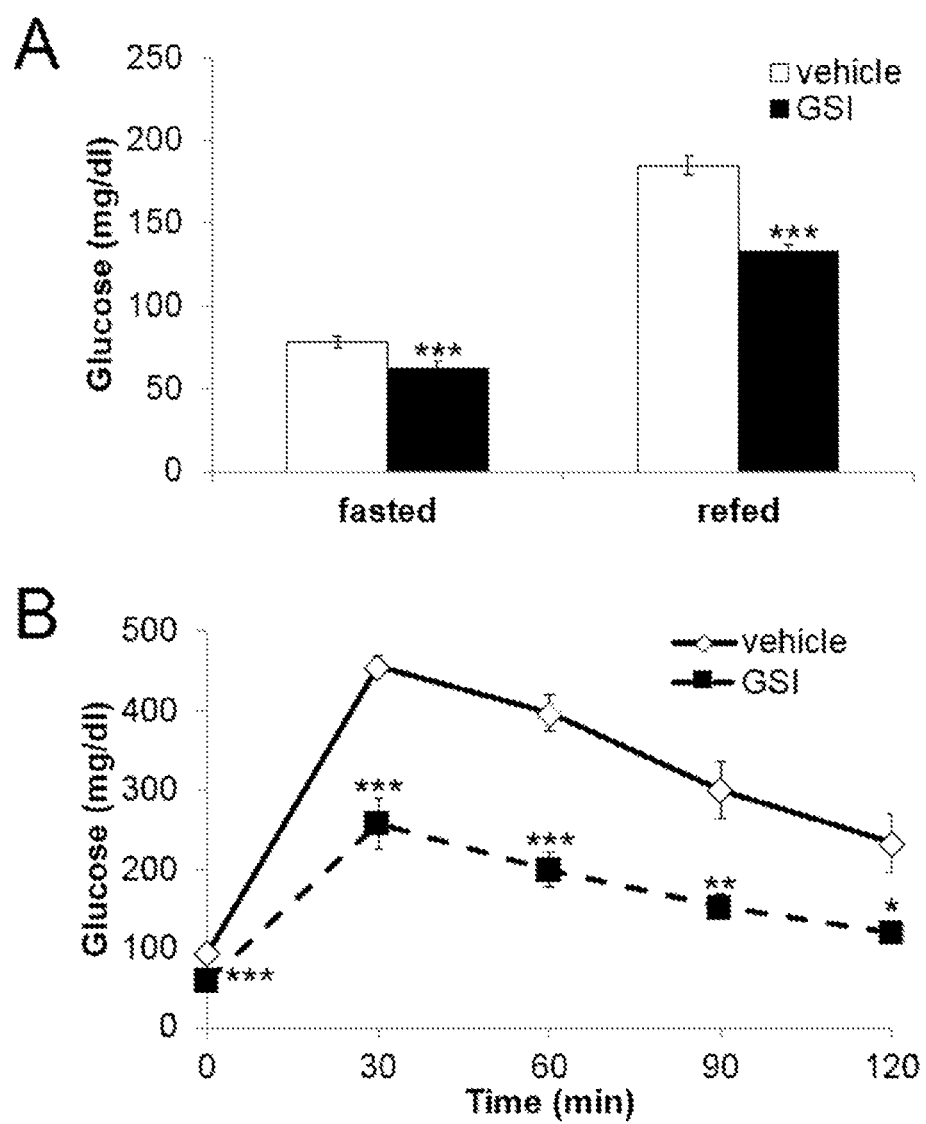
FIG. 3: Plasma glucose levels of GSI and vehicle treated mice. $*p<0.05$ $p<0.01$ $*p<0.001$ vs. vehicle.

GSI (which will be used interchangeably with the specific drug name, dibenzazepine, DBZ) treatment reduced both fasted as well as refed (or exogenous) glucose in DIO mice as compared to vehicle (normal saline containing 0.5% methoxycellulose/0.1% Tween-80) (FIG. 3). Treatment of mice with the gamma-secretase inhibitor, dibenzazepine (DBZ) reduces fasted or refed plasma glucose (FIG. 3 Panel A), and improves glucose clearance (FIG. 3 Panel B).

EXAMPLE 2

GSI Lowers Serum Triglycerides (TG)

Mice were administered GSI or vehicle alone to determine the effect of GSI treatment on serum triglyceride levels.

Figure 4:
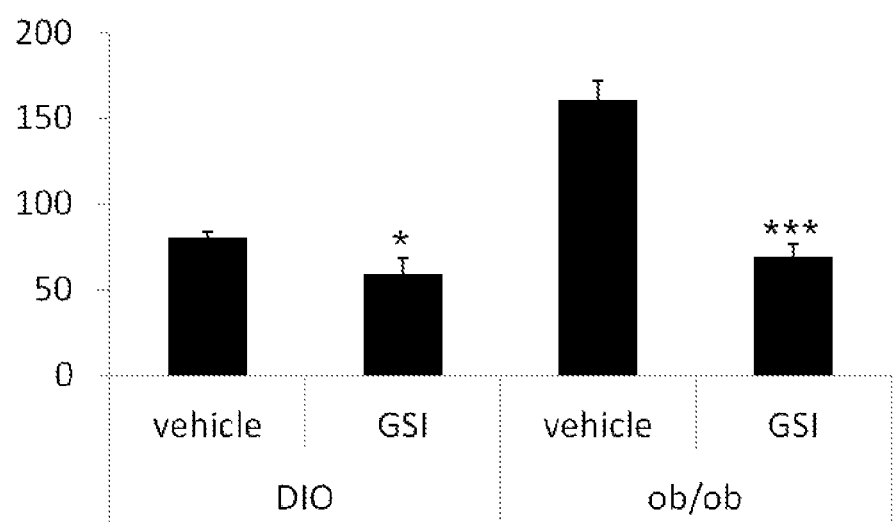
FIG. 4: Serum triglyceride levels in mice treated with GSI or vehicle only. $*p<0.05$ $p<0.01$ $*p<0.001$ vs. vehicle.
Figure 5:
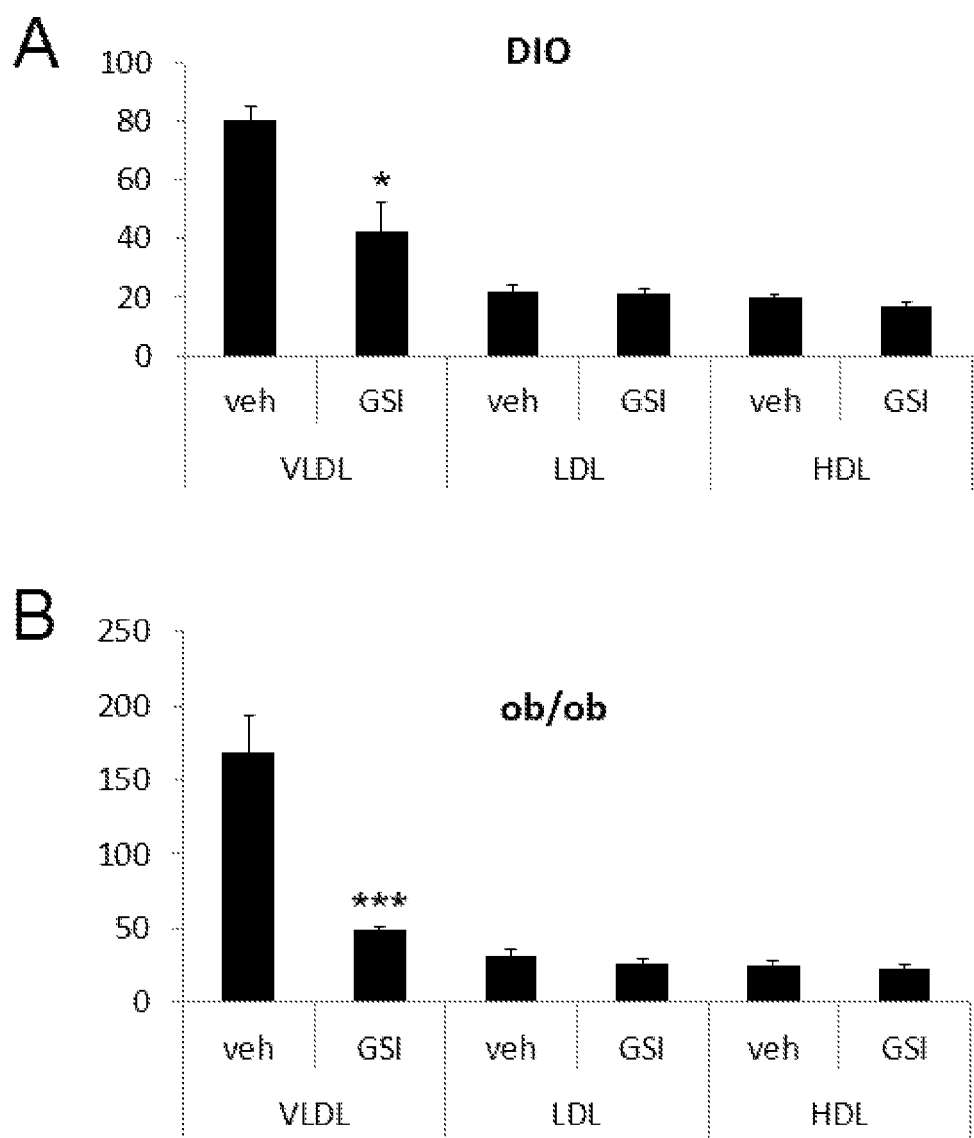
FIG. 5: VLDL, LDL, and HDL fraction serum triglyceride levels of mice administered GSI or vehicle only. $*p<0.05$ $p<0.01$ $*p<0.001$ vs. vehicle.
Figure 6:
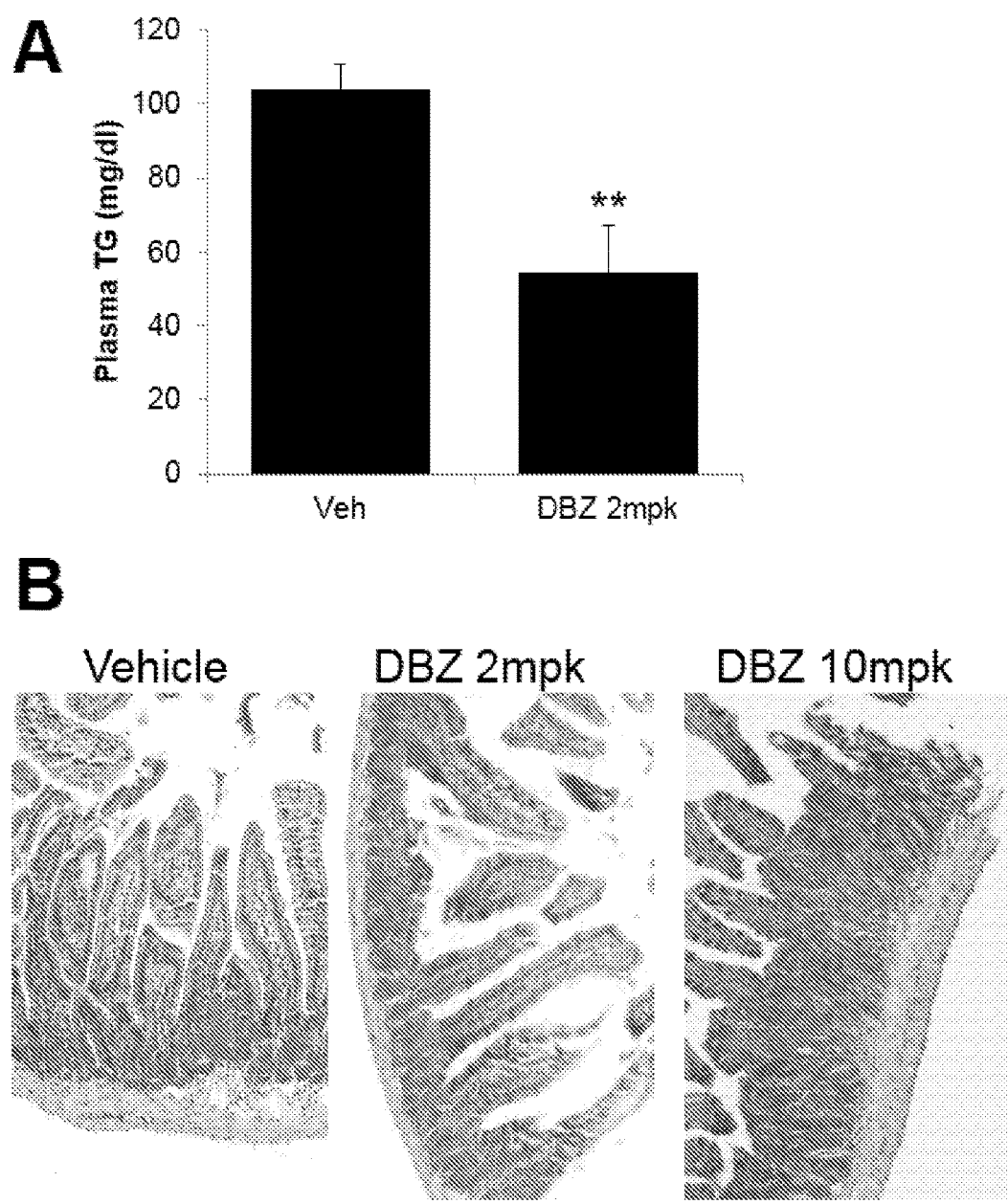
FIG. 6: Lower plasma TG levels with low dose DBZ not associated with apparent GI toxicity. $*p<0.05$ $p<0.01$ $*p<0.001$ vs. vehicle.

Mice administered GSI had lower plasma triglycerides than mice administered vehicle alone (FIG. 4). DBZ-treated obese mice, diet-induced obese (DIO) and leptin-deficient obese (ob/ob), show lower plasma triglyceride (TG) as compared to vehicle treatment. Analysis of VLDL, LDL, and HDL fractions showed that GSI lowered triglycerides in the VLDL fraction (FIG. 5). Lower plasma TG levels with low dose DNZ was not associated with apparent gastrointestinal (GI) toxicity (FIG. 6).

Figure 7:
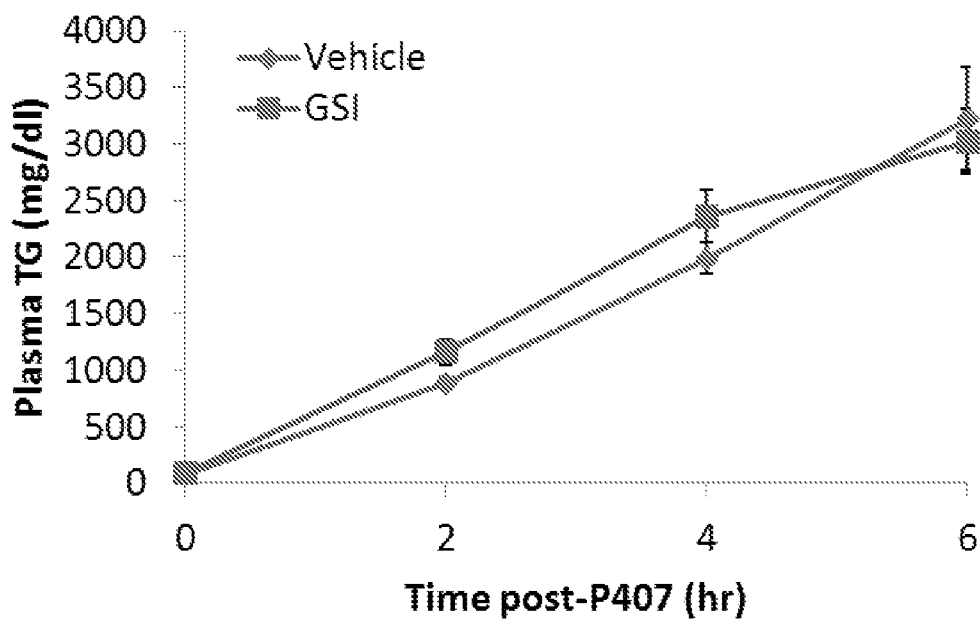
FIG. 7: Time course of plasma triglyceride levels of mice administered GSI or vehicle only.
Figure 8:
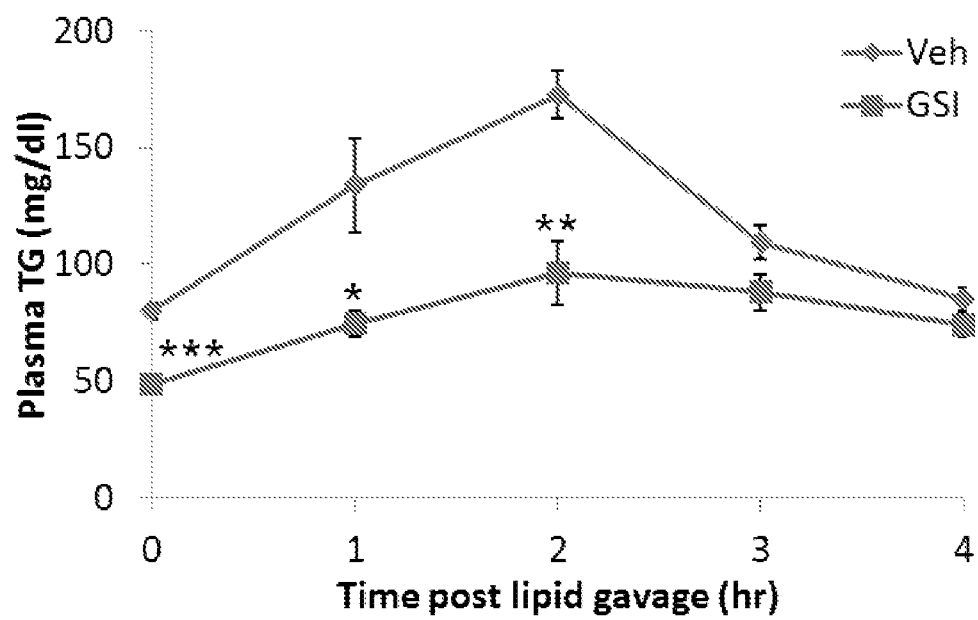
FIG. 8: Time course of plasma triglyceride excursion following lipid gavage in mice administered GSI or vehicle only. $*p<0.05$ $p<0.01$ $*p<0.001$ vs. vehicle.

DBZ-induced lower plasma TG in diet-induced obese (DIO) and leptin-deficient obese (ob/ob) mice is in the VLDL fraction. GSI treated mice showed normal triglyceride secretion (FIG. 7). Normal plasma TG levels after lipoprotein lipase inhibition with Poloxamer 407 (P407) indicates that DBZ does not affect TG secretion. GSI treated mice showed less plasma triglyceride excursion after lipid gavage compared to mice administered vehicle only (FIG. 8). Lower plasma TG levels after oral olive oil gavage indicates that DBZ increases TG clearance. The combination of these pieces of data (normal TG secretion, less fasted TG and lower TG in serum after gavage) suggests either: (1) Adipose phenotype, i.e., less lipolysis of fat stores, or (2) Liver phenotype, i.e., increased TG uptake from circulation. To differentiate these—we created a liver-specific gamma-secretase knockout mouse.

EXAMPLE 3

Hepatocyte-specific Gamma-secretase Deficiency Reduces Plasma Triglycerides

To elucidate the mechanism of the results of Example 2, a mouse that had gamma-secretase deficiency specifically in hepatocytes was created (Albumin-cre:Nicastrin fl/fl mice, henceforth L-Ncst).

Figure 9:
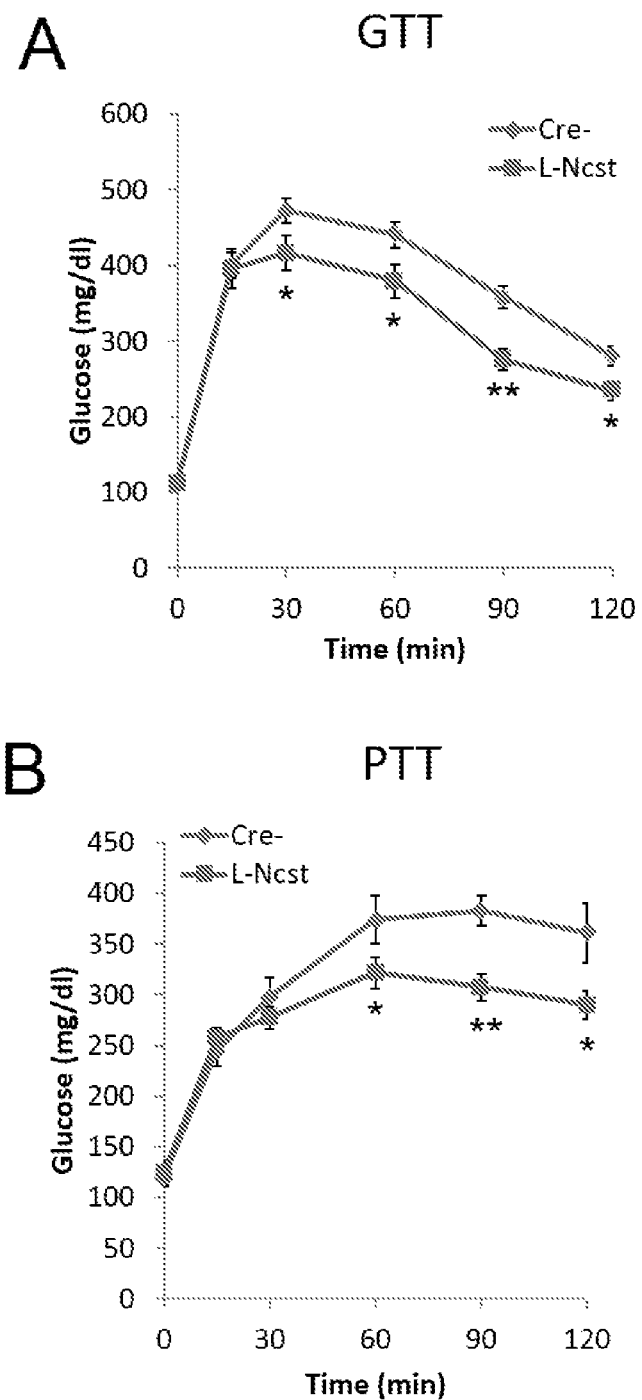
FIG. 9: Glucose tolerance test (GTT) and pyruvate tolerance test (PTT) plots for control and L-Ncst mice. $*p<0.05$ $p<0.01$ $*p<0.001$ vs. Cre-.

L-Ncst mice showed similar glucose improvement to GSI-treated mice according to glucose tolerance test (GTT) and pyruvate tolerance test (PTT) (FIG. 9). L-Ncst (hepatocyte-specific gamma-secretase knockout) mice showed improved glucose clearance as compared to Cre-control mice, similar GSI-treatment, when challenged with either an intraperitoneal glucose (GTT) or pyruvate (PTT) load.

Figure 10:
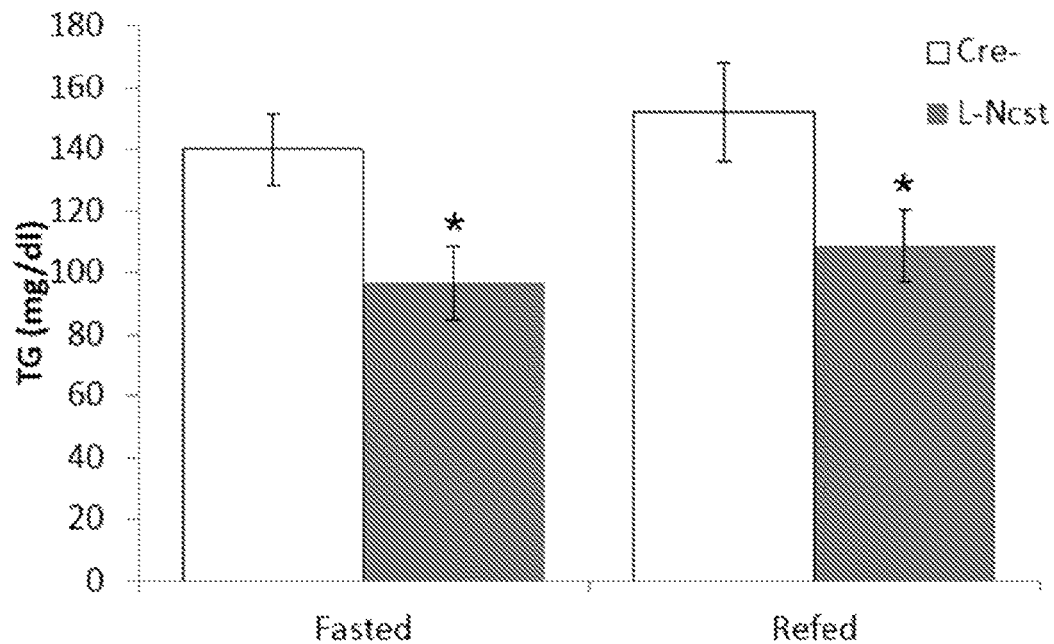
FIG. 10: Serum triglyceride levels for fasted and refed chow-fed L-Ncst mice.

Chow-fed L-Ncst mice had lower plasma TG (FIG. 10). These data prove that liver γ-secretase is involved in TG clearance from circulation, or in the production of a secreted protein (hepatokine) that alters TG metabolism. Of these, the likeliest target is ApoC3, an apolipoprotein produced exclusively in liver that has been proven to affect TGs. People or mice with ApoC3 deficiency show very low plasma TG, and low risk for coronary disease (CAD). Conversely, excessive production of ApoC3 is associated with high serum TG and excess CAD.

Figure 11:
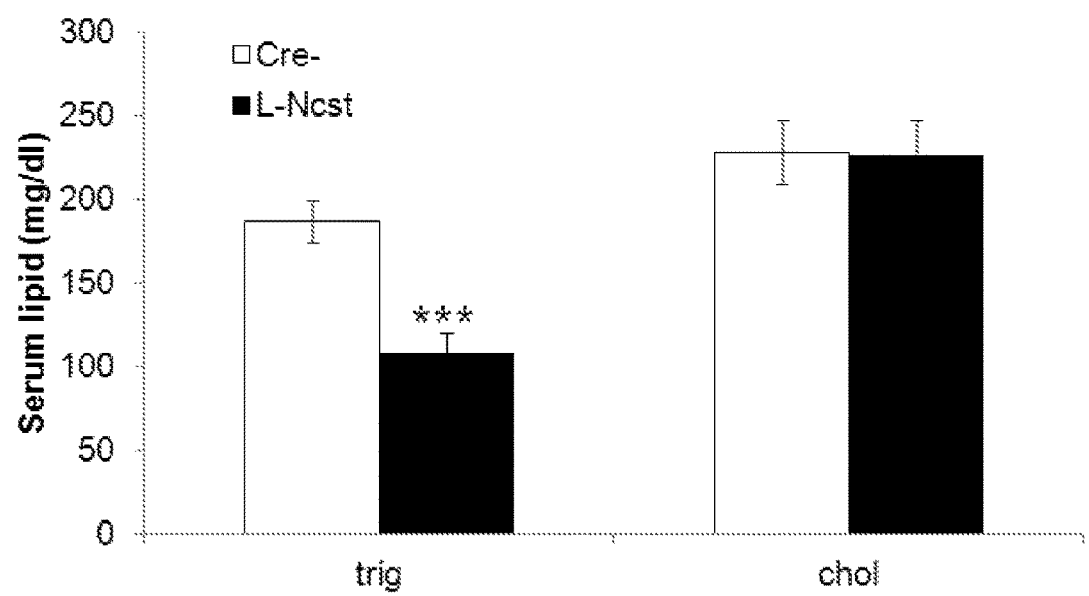
FIG. 11: Serum lipid levels for control and L-Ncst mice. $*p<0.05$ $p<0.01$ $*p<0.001$ vs. Cre-.
Figure 12:
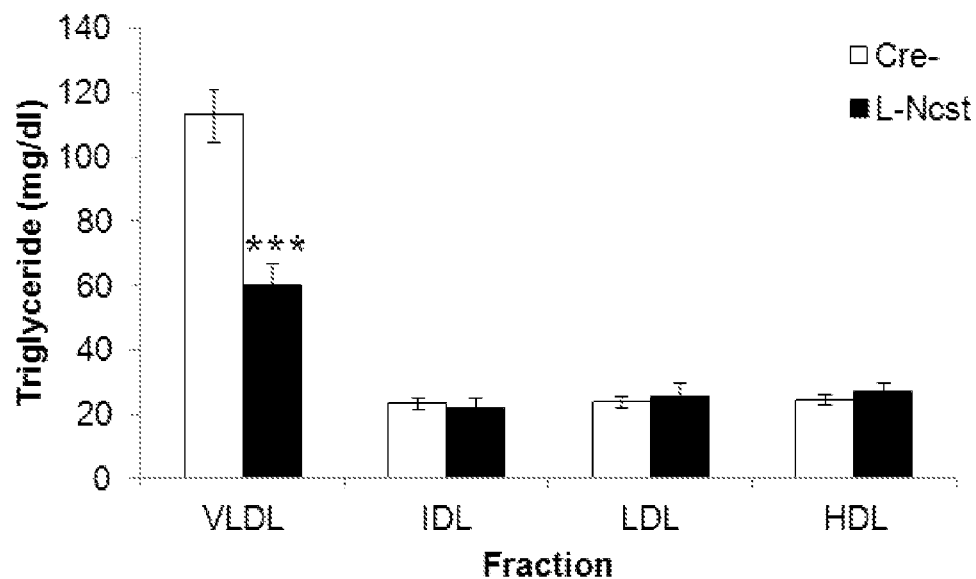
FIG. 12: Triglyceride levels by plasma fraction for control and L-Ncst mice. $*p<0.05$ $p<0.01$ $*p<0.001$ vs. Cre-.
Figure 13:
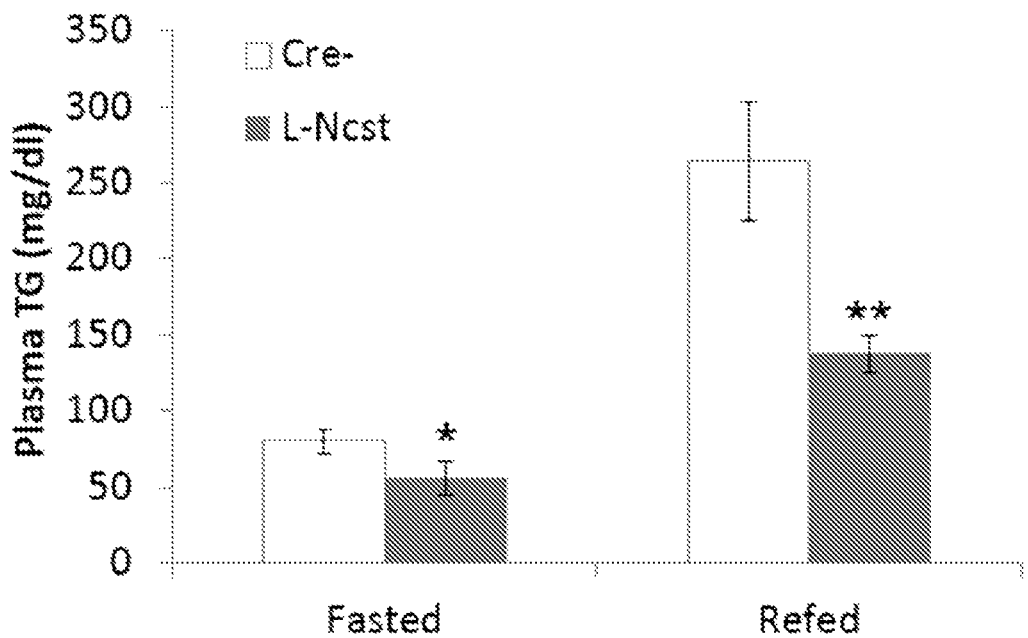
FIG. 13: Plasma triglyceride levels of fasted and refed control and L-Ncst mice. $*p<0.05$ $p<0.01$ $*p<0.001$ vs. Cre-.
Figure 14:
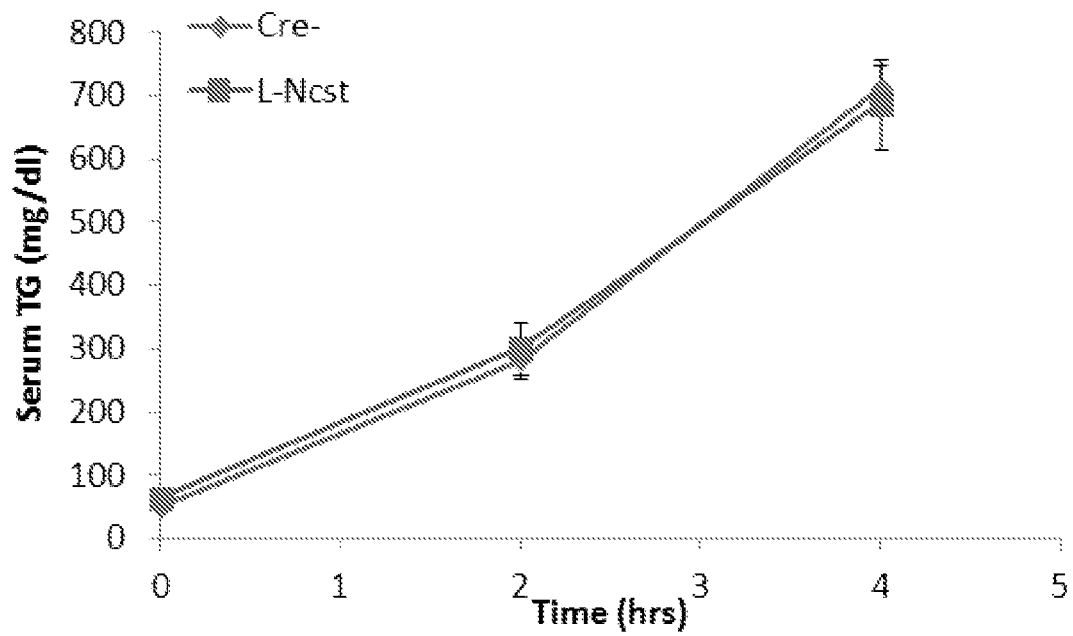
FIG. 14: Serum triglyceride levels in HFD-fed control and L-Ncst mice.
Figure 15:
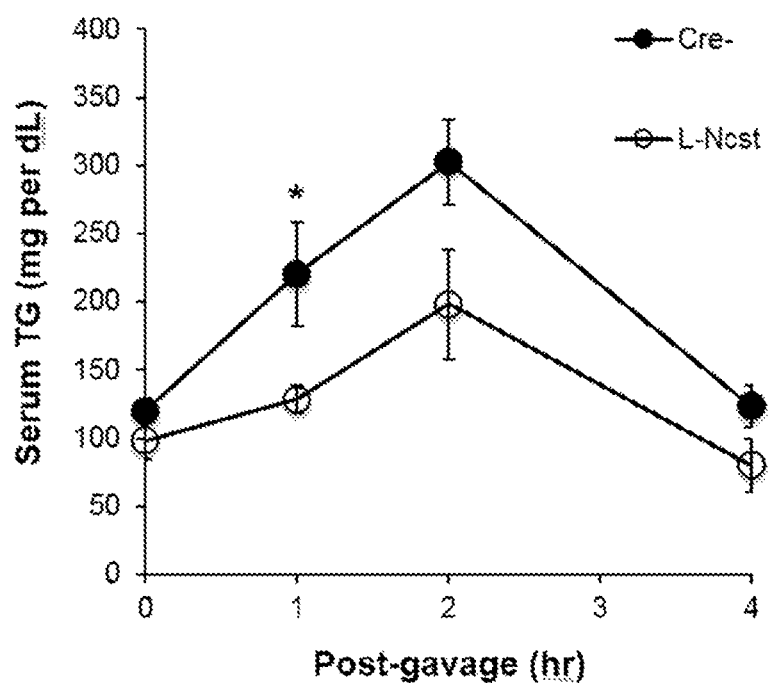
FIG. 15: Time course of serum triglyceride levels in control and L-Ncst mice. $*p<0.05$ $p<0.01$ $*p<0.001$ vs. Cre-.

High fat diet (HFD) fed L-Ncst mice had lower refed serum triglycerides compared to control mice (FIG. 11). L-Ncst mice showed lower serum TG compared to Cre-control mice, similar to GSI-treated mice. HFD feeding increased the difference between Cre- and L-Ncst mice in serum TG. Lower p triglycerides were observed in the VLDL fraction (FIG. 12). As with GSI treatment, reduced plasma TG seen in L-Ncst mice as compared to Cre-control mice is in the VLDL fraction. Both fasted, but more markedly refed plasma triglycerides, were lower in L-Ncst mice compared to control mice (FIG. 13). Both fasted and refed serum TG are lower in L-Ncst mice than in Cre-control mice. Triglyceride secretion was unchanged in HFD-fed L-Ncst mice compared to control mice (FIG. 14). As with GSI treatment, comparable serum TG levels after lipoprotein lipase inhibition with Poloxamer 407 (P407) indicates that L-Ncst mice show similar TG secretion as Cre-control mice. As with GSI treatment, serum TG levels after olive oil gavage in L-Ncst mice as compared to Cre-controls proves that L-Ncst mice show increased TG clearance (FIG. 15).

EXAMPLE 4

Lower Serum TG Observed in L-Ncst Mice is by Lower ApoC3

Figure 16:
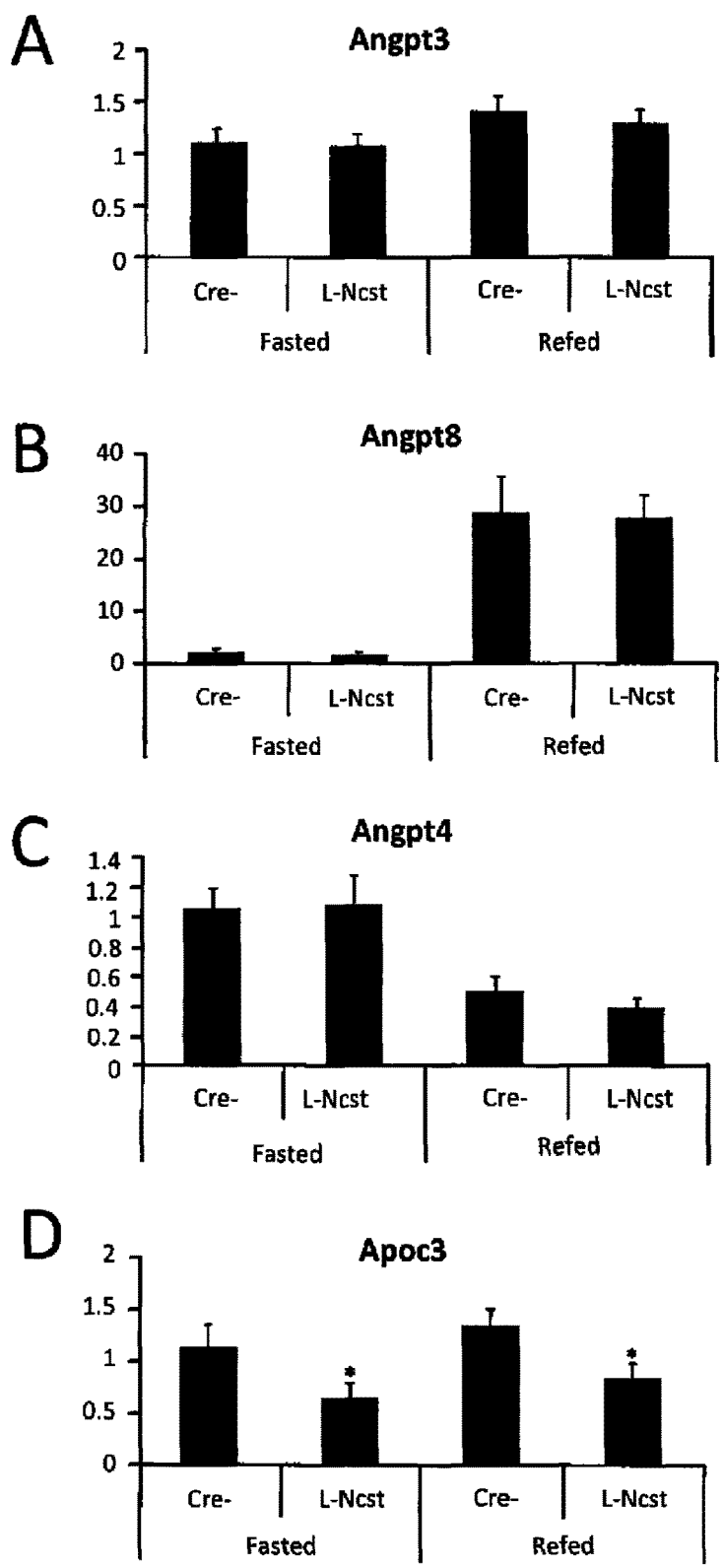
FIG. 16: Relative gene expression levels of fasted and refed control and L-Ncst mice.
Figure 17:
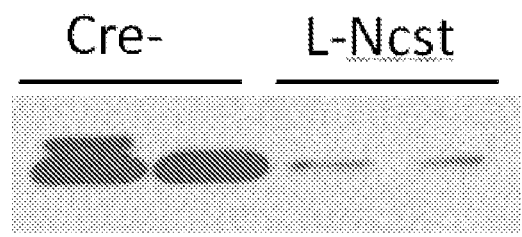
FIG. 17: Western blot for ApoC3 serum levels in HFD-fed control and L-Ncst mice.
Figure 18:
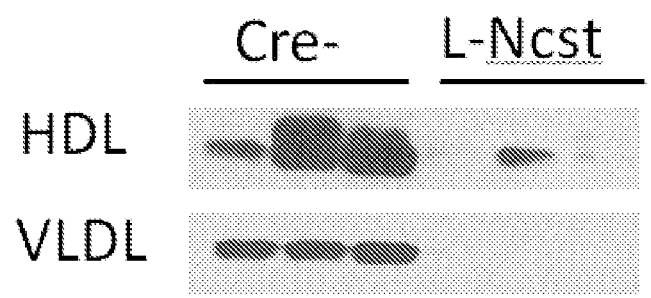
FIG. 18: Western blot for ApoC3 levels in HDL and VLDL serum fractions in HFD-fed control and L-Ncst mice.
Figure 19:
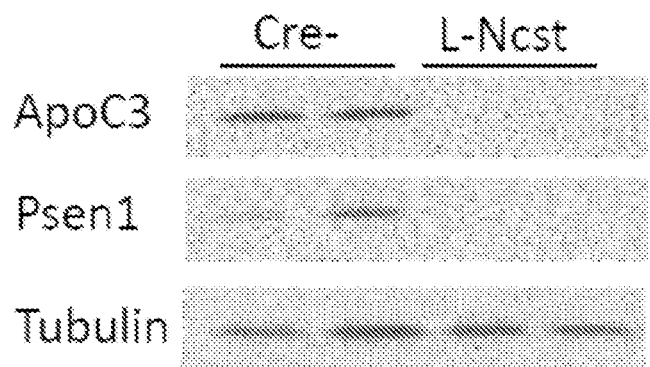
FIG. 19: Western blot for hepatic ApoC3 levels in control and L-Ncst mice.

A gene expression analysis of hepatic genes that affect serum triglycerides showed that only Apoc3 expression was altered in the L-Ncst mice (FIG. 16). Serum ApoC3 levels were lower in HFD-fed L-Ncst mice compared to Cre-control mice (FIG. 17). Serum levels of the apolipoprotein ApoC3 levels were lower in both HDL and VLDL fractions in HFD-fed L-Ncst mice compared to Cre-control mice (FIG. 18). Hepatic ApoC3 levels were also decreased in L-Ncst mice compared to control mice (FIG. 19).

Figure 20:
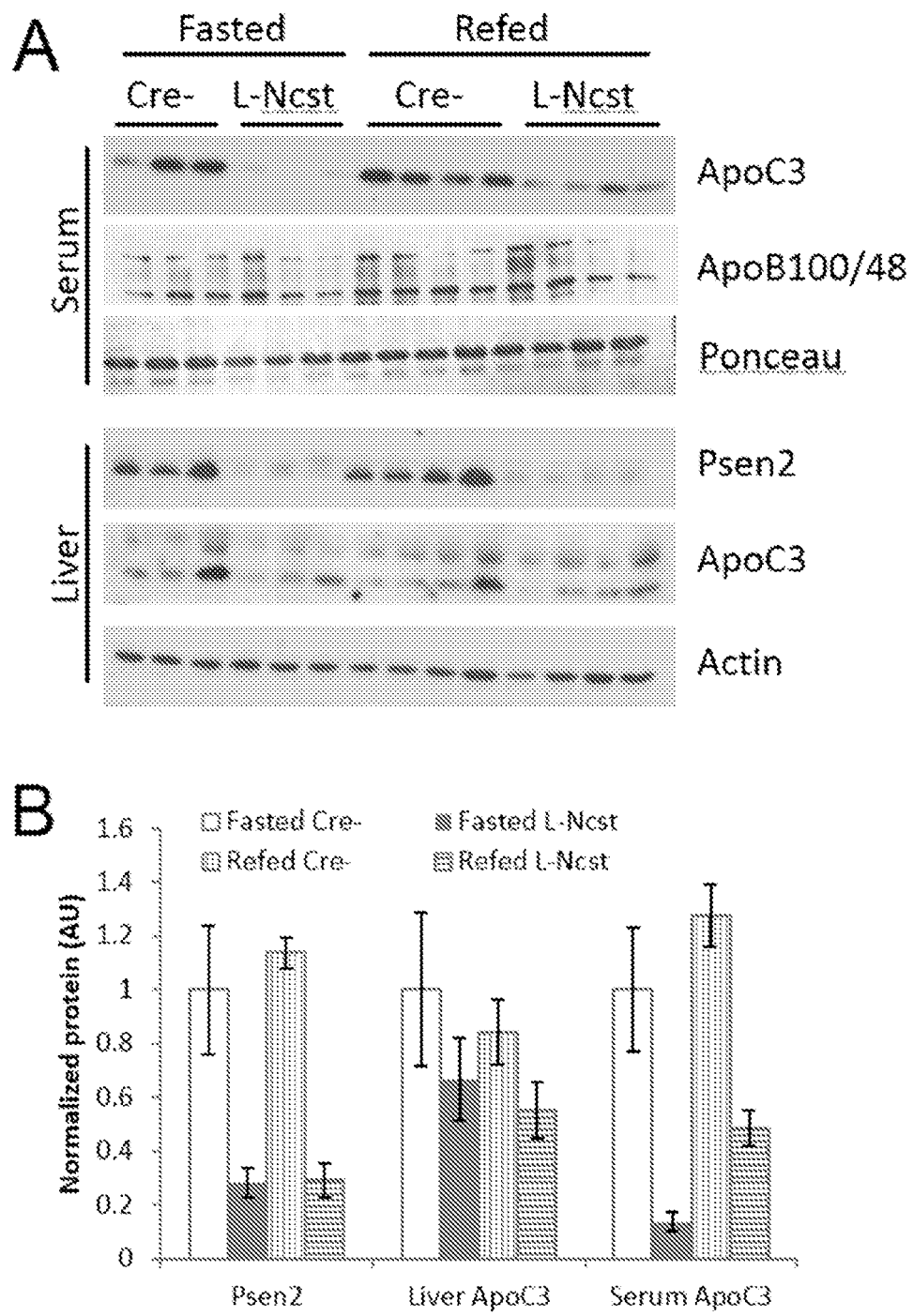
FIG. 20: Western blot for hepatic ApoC3 levels in L-Ncst mice.
Figure 21:
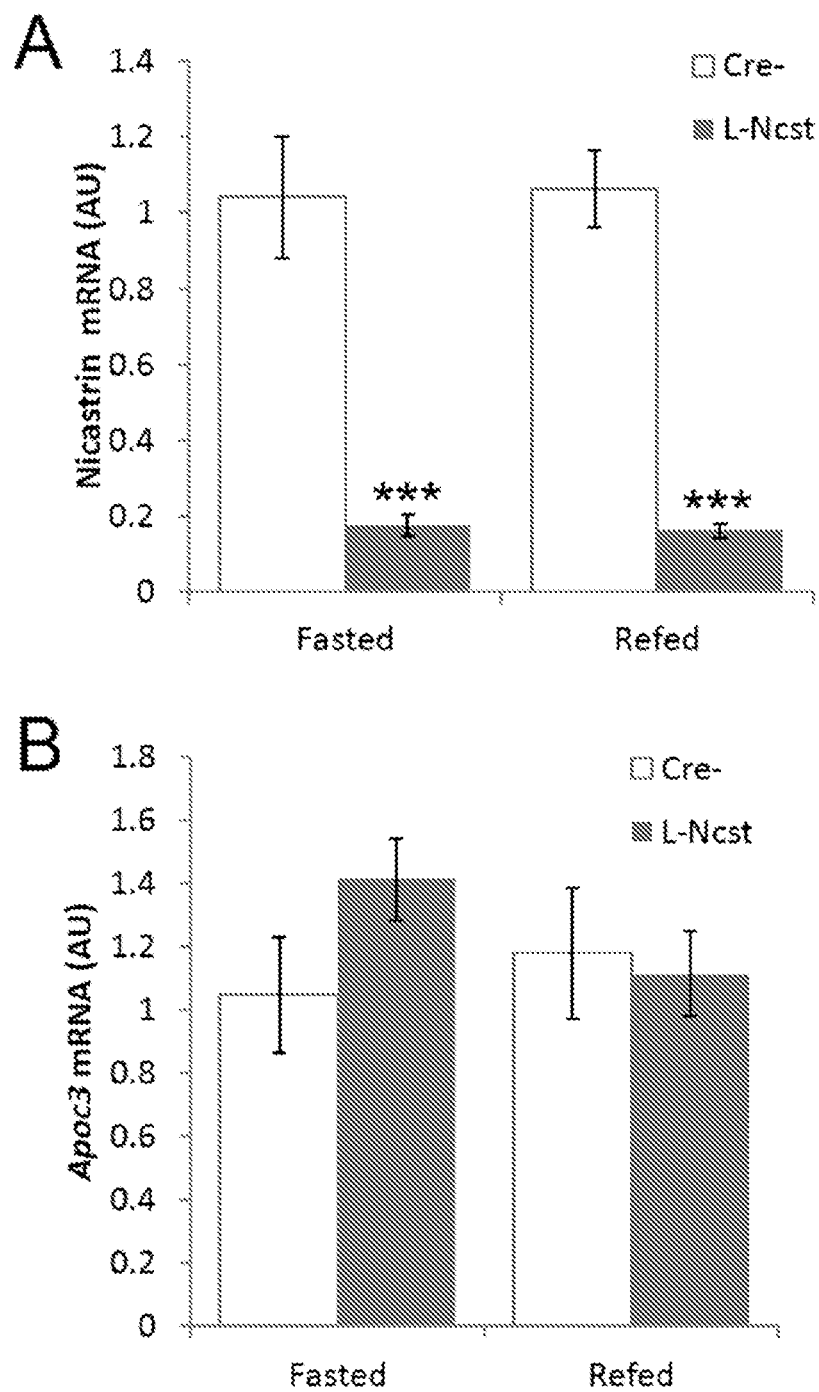
FIG. 21: mRNA expression of Nicastrin and ApoC3 in fasted and refed control and L-Ncst mice.

In fasted and refed L-Ncst mice, ApoC3 protein expression was decreased in serum and liver compared to fasted and refed control mice (FIG. 20). Serum levels of the apolipoprotein ApoC3 were lower in L-Ncst mice even though liver mRNA and protein for ApoC3 were unaffected. Also, Psen2 protein expression was decreased in liver, but no change in hepatic protein, ApoB100/48 in fasted and refed L-Ncst mice compared to control mice. Correspondingly, there was no change in Apoc3 mRNA in chow-fed L-Ncst mice (FIG. 21).

Figure 22:
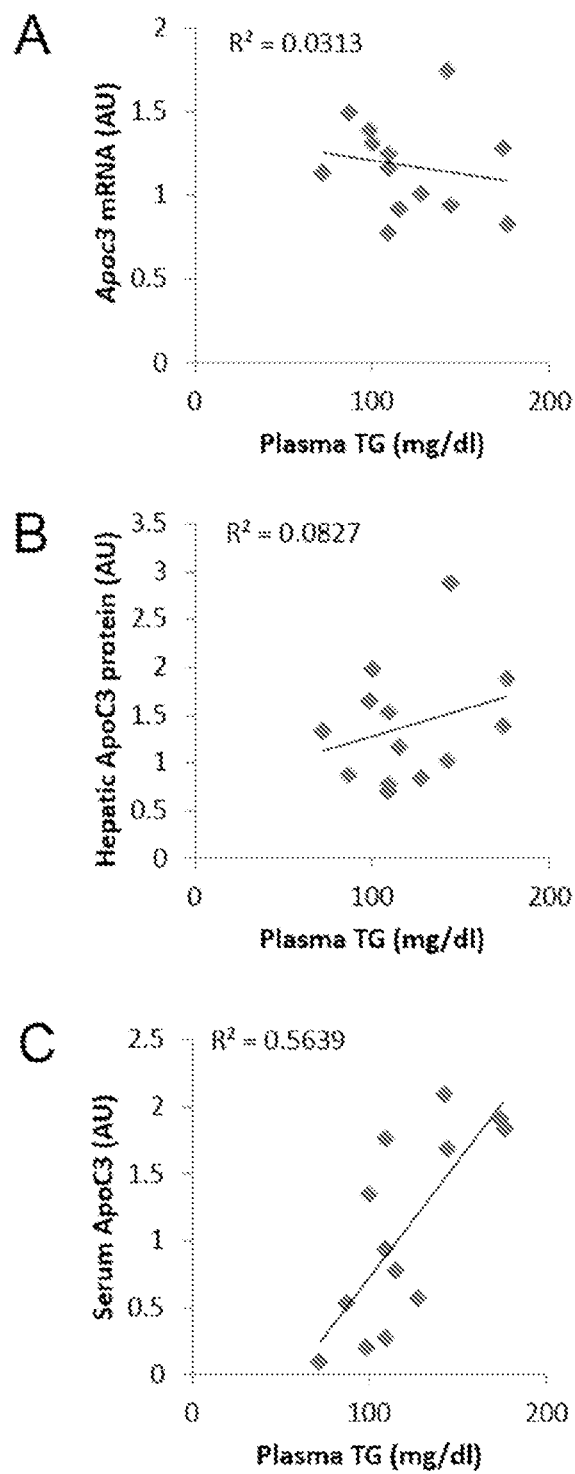
FIG. 22: Correlation between ApoC3 (hepatic Apoc3 mRNA, hepatic ApoC3 protein, and serum ApoC3) with Plasma triglyceride.

Serum ApoC3 correlated with plasma TG, but hepatic ApoC3 and Apoc3 mRNA did not correlate with plasma TG (FIG. 22). These data suggest that liver gamma-secretase is involved in either ApoC3 secretion or clearance from circulation, as only serum ApoC3 (but not hepatic Apoc3 mRNA or hepatic ApoC3 protein) are reduced in L-Ncst mice.

EXAMPLE 5

Figure 23:
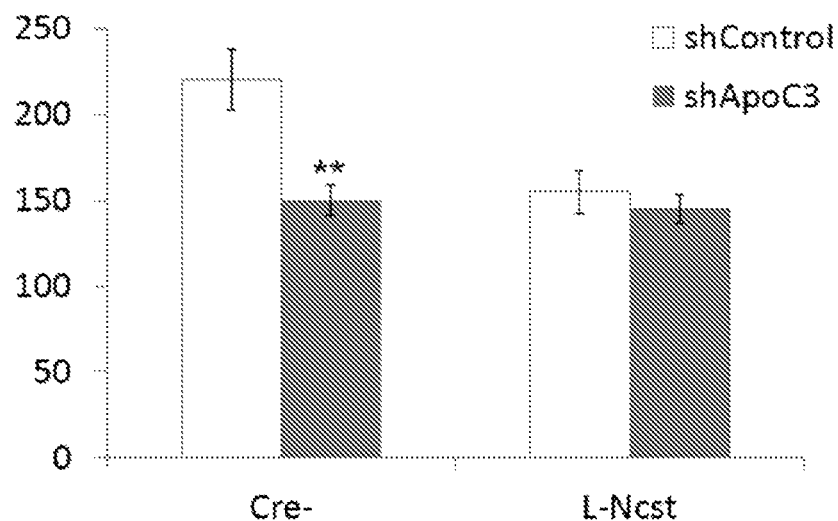
FIG. 23: Serum triglyceride levels in HFD-fed control and L-Ncst mice following liver ApoC3 knockdown by adeno-delivered shRNA. $*p<0.05$ $p<0.01$ $*p<0.001$ vs. Cre-.
Figure 23:
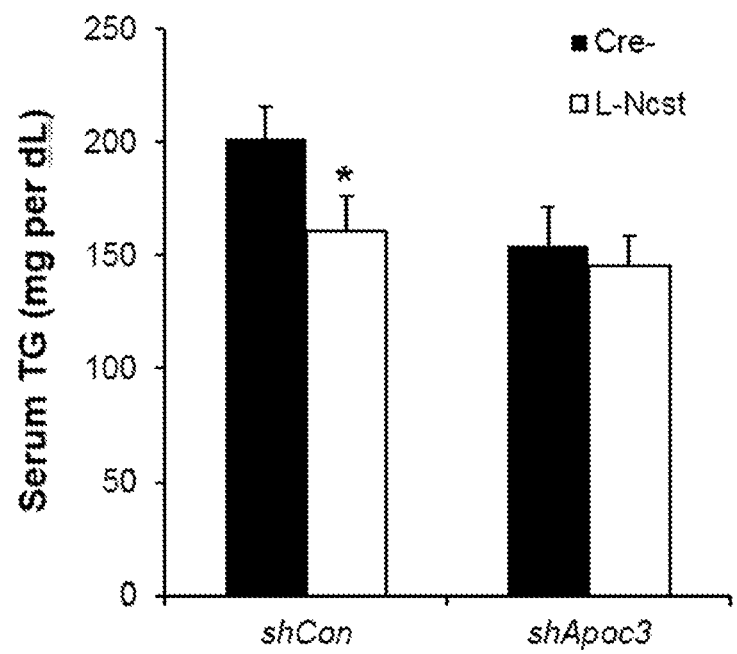

Adenoviral Transduction of Cre-control and L-Ncst Mice and shRNA Mediated Knockdown in Rat Hepatocytes Liver ApoC3 knockdown (with adeno-delivered shRNA) eliminates difference between HFD-fed Cre- and L-Ncst mice (FIG. 23). Serum, but not hepatic, ApoC3 protein levels correlate with plasma TG. These data prove that lower serum TG observed in L-Ncst mice is by lower ApoC3. Future work will be to determine the mechanism by which this happens.

Figure 24:
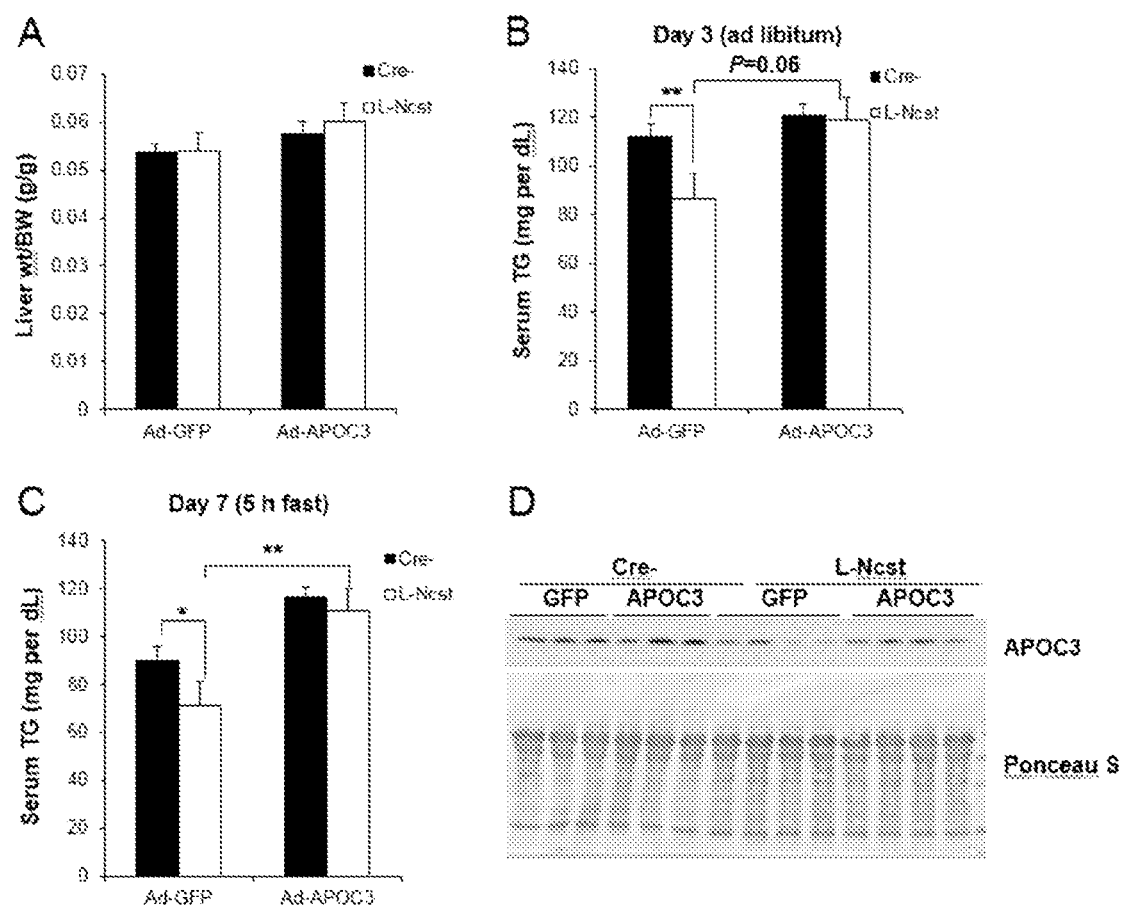
FIG. 24: Adenoviral transduction of L-Ncst mice with ApoC3 increases plasma TG to levels comparable to Cre-control mice. p<0.05 p<0.01 *p<0.001 vs. Cre-Ad-GFP mice.
Figure 25:
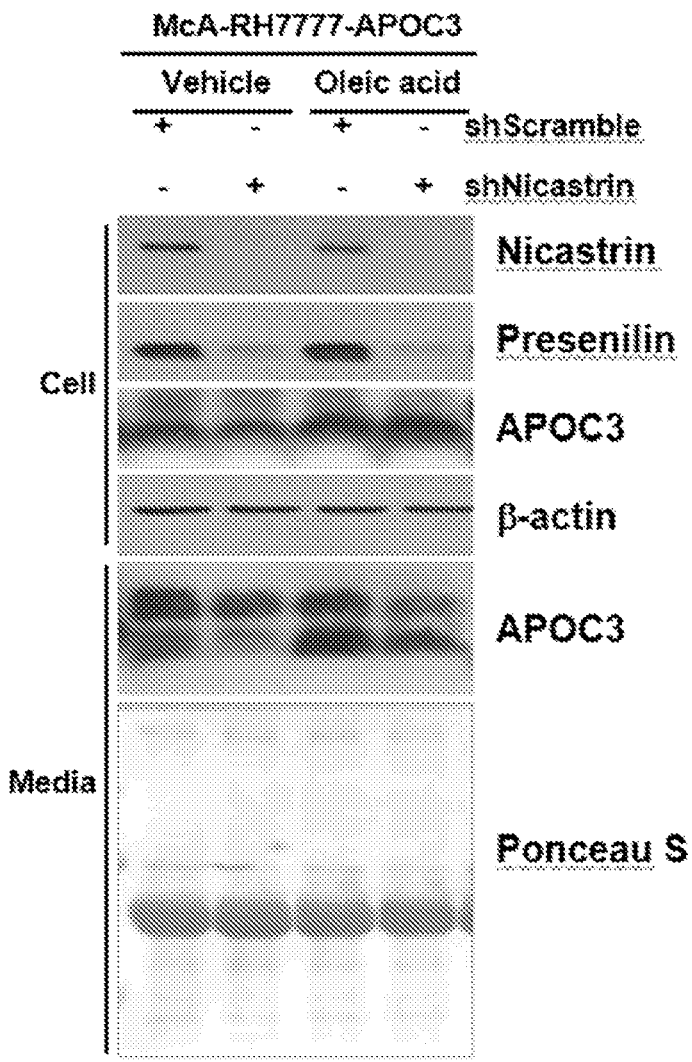
FIG. 25: shRNA-mediated knockdown of Nicastrin (sequence of shRNA: CTCCTTCCACAATCGGTATTA SEQ ID NO. 59) in mouse hepatocytes reduces ApoC3 secretion.

Adenoviral transduction of L-Ncst mice with ApoC3 increases serum TG to levels comparable to Cre-control mice (FIG. 24). shRNA-mediated knockdown of Nicastrin (sequence of shRNA: CTCCTTCCACAATCGGTATTA SEQ ID NO. 59) in mouse hepatocytes reduces ApoC3 secretion (FIG. 25).

Discussion

Hypertriglyceridemia is not easily treated. Currently available therapies include fibrates (fenofibrate, gemfibrozil)

and other less potent triglyceride-lowering agents such as bile acid sequesterants, niacin and statins. Fibrates have been shown to reduce cardiovascular risk, but many patients are unable to reach plasma triglyceride treatment goals with these medications. As such, novel molecular targets to reduce plasma triglycerides have been long-sought.

Recent work has shown that the liver-secreted apolipoprotein, ApoC3, may impact plasma triglyceride levels. Humans with genetic variants that confer partial ApoC3 deficiency, including several Amish and Ashkenazi Jewish populations, exhibit lower plasma triglyceride levels, leading to lower risk of coronary heart disease (Pollin T I, Science, 2008). These human studies have been confirmed with mouse data—ApoC3 knockout mice demonstrate markedly lower plasma triglyceride levels (Jong et, al, J Lipid Res, 2001), whereas mouse models of ApoC3 overexpression given rise to massive hypertriglyceridemia and excess atherosclerosis (Masucci-Magoulas L, et al, Science, 1997). This data was so compelling that various pharmaceutical companies are targeting ApoC3 as a potentially novel means to reduce plasma triglycerides (Gaudet D et al., N Engl J Med, 2014), and hopefully reduce atherosclerosis and consequent coronary heart disease.

The above Examples show that inhibition of the gamma-secretase complex in liver reduces both liver, and circulating ApoC3, leading to lower plasma triglycerides. Gamma-secretase is a enzymatic complex composed of targeting (Nicastrin), catalytic (Presenlin) as well as regulatory subunits (Aph1, PEN2) (Tolia and De Strooper, Semin Cell Dev Biol, 2009). This enzyme is the prototype for intramembrane proteases, and its known targets include Notch receptors, Alzheimer's precursor protein (APP), and others (De Strooper and Annaert, Annu Rev Cel Dev Biol, 2010). Gamma-secretase inhibitors were developed, in part, to reduce APP cleavage to beta-amyloid, in a failed attempt to treat Alzheimer's disease (De Strooper B et al., Nat Rev Neurol, 2010). The present invention provides a new use for GSIs in the treatment of metabolic disease.

It was found that treatment of lean mice reduces plasma triglyceride in a dose-dependent manner. Plasma triglyceride lowering in genetic (leptin deficient ob/ob mice) or diet-induced mouse models of obesity was even more profound, with reductions approaching 75% of vehicle-treated animals. To elucidate the mechanism of this result, we created the L-Ncst mouse that had gamma-secretase deficiency specifically in hepatocytes. L-Ncst mice had similar reductions in plasma triglyceride as GSI-treated mice, proof that the mechanism of GSI-induced reduction in plasma triglyceride is through effects on liver. L-Ncst mice had approximately 40% reduced plasma triglyceride as compared to control mice when fed normal chow, but this rises to a staggering 70% reduction when mice were challenged with high-fat diet feeding. In both GSI-treated and L-Ncst mice, plasma ApoC3 levels were markedly and proportionately reduced to plasma triglyceride lowering, suggesting that this effect is ApoC3-mediated. Interestingly, plasma ApoC3 levels positively correlate with plasma triglyceride, whereas hepatic ApoC3 gene expression or protein levels do not at all. This suggests that reducing plasma ApoC3 levels, not necessarily by reducing liver ApoC3 expression, reduces plasma triglyceride. As such, gamma-secretase inhibition with GSIs or liver-specific gamma-secretase blockers would be predicted to have a greater, and perhaps synergistic, effect in reducing plasma triglyceride as compared to drugs that solely target ApoC3 expression.

It is expected that antagonism of liver or whole-body gamma-secretase in humans will reduce both hepatic and plasma ApoC3 levels, will reduce plasma glucose levels, will reduce plasma triglycerides, and will protect from obesity induced hypertriglyceridemia. As GSI-treated and L-Ncst mice show similar reductions in plasma triglyceride, this implicates gamma-secretase function in the liver as the relevant mechanism underlying this effect. GSIs have significant gut toxicity, leading to dose- and time-dependent goblet cell metaplasia (Milano J et al., Toxicol Sci; Real P J et al., Nature Medicine, 2009). This level of GI toxicity has been deemed acceptable for cancer therapy (Andersson and Lendahl, Nat Rev Drug Disc, 2014), and perhaps even for Alzheimer's Disease (Imbimbo B P et al., Expert Opin Investig Drugs, 2011), but unlikely for chronic treatment of hypertriglyceridemia. As such, liver-specific inhibitors of the gamma-secretase, by methods described above, would be advantageous to maintain efficacy while limiting or even eliminating GI toxicity.

REFERENCES

Andersson E R and Lendahl U. Therapeutic modulation of Notch signaling—are we there yet? Nature Reviews Drug Discovery 13: 357-378 (2014).

Bergmans B A and De Strooper B. Gamma-secretases: from cell biology to therapeutic strategies. Lancet Neurol 9: 215-226 (2010).

Chan S M, Weng A P, Tibshirani R, Aster J C, and Utz P J. Notch signals positively regulate activity of the mTOR pathway in T-cell acute lumphoblastic leukemia. Blood 110(1): 278-286 (2007).

De Strooper and Annaert W. Novel research horizons for presenilins and gamma-secretases in cell biology. Annu Rev Cell Dev Biol 26: 235-260 (2010).

De Strooper B, Vassar R, and Golde T. The secretases: enzymes with therapeutic potential in Alzheimer disease. Nat Rev Neurol 6(2): 99-107 (2010).

Efferson C L, Einkwlmann C T, Ware C, Sullivan T, Giampaoli S, Tammam J, Patel S, Mesiti G, Reilly J F, Gibson R E, Buser C, Yeatman T, Coppola D, Winter C, Clark E A, Draetta G F, Strack P R, and Majumder P K. Downregulation of Notch pathway by a gamma-secretase inhibitor attenuates AKT/mammalian target of rapamycin signaling and glucose uptake in an ERBB2 transgenix breast cancer model. Cancer Res 70(6): 2476-2484 (2010).

Gaudet D, Brisson D, Trembley K, Alexander V J, Singleton W, Hughes S G, Geary R S, Baker B F, Graham M J, Crooke R M, and Witzum J L. Targeting APOC3 in the familial chylomicronemia syndrome. N Engl J Med 371 (3):2200-2206 (2014).

Jong M C, Rensen P C, Dahlmans V E, van der Boom H, Berkel T J, and Havekes L M. Apolipoprotein C-III deficiency accelerates triglyceride hydrolysis by lipoprotein lipase in wild-type and apoE knockoutmice. J Lipid Res 42(10): 1578-1585 (2001).

Kitamura T, Kitamura Y I, Funahashi Y, Shawber C J, Castrillon D H, Kollipara R, DePinho R A, Kitajewski J, and Accili D. A Foxo/Notch pathway controls myogenic differentiation and fiber type specification. J Clin Invest 117(9): 2477-2485 (2007).

Li S, Brown M S, Goldstein J L. Bifurcation of insulin signaling pathway in rat liver: mTORC1 required for stimulation of lipogenesis, but not inhibition of gluconeogenesis. Proc Natl Acad Sci USA 107(8):3441-3446 (2010).

Masucci-Magoulas L, Goldberg I J, Bisgaier C L, Serajuddin H, Francone O L, Breslow J L, Tall A R. A mouse model with features of familial combine hyperlipidemia. Science 275(5298): 391-394 (1997).

Mishra N, Yadav N P, Rai V K, Sinha P, Yadav K S, Jain S, and Arora S. Efficient Hepatic Delivery of Drugs: Novel Strategies and Their Significance. BioMed Research International 2013: 382184 (2013).

Pollin T I, Damcott C M, Shen H, Ott S H, Horenstein R B, Post W, McLenithan J C, Bielak L F, Peyser P A, Mitchell B D, Miller M, O'Connell J R, Shuldiner A R. A null mutation in human APOC3 confer a favorable lipid profile and apparent cardioprotection. Science 322(5908): 1702-1705 (2008).

Prakash T P, Graham M J, Yu J, Carty R, Low A, Chappell A, Schmidt K, Zhao C, Aghajan M, Murray H F, Riney S, Booten S L, Murray S F, Gaus H, Crosby J, Lima W F, Guo S, Monia B P, Swayze E E, and Seth P P. Targeted delivery of antisense oligonucleotides to hepatocytes using triantennary N-acetyl galactosamine improves potency 10-fold in mice. Nucleic Acids Research 42(13): 8796-8807 (2014).

Real P J, Tosello V, Palmero T, Castillo M, Hernando E, de Stanchina E, Sulis M L, Barnes K, Sawai C, Homminga I, Meijerink J, Aifantis I, Basso G, Cordon-Cardo C, Ai W, and Ferrando A. Gamma secretase inhibitors reverse glucocorticoid resistance in T-ALL. Nat. Med 15(1): 50-58 (2009).

Sengupta S, Peterson T R, Laplante M, Oh S, Sabatini D M. mTORC1 controls fasting-induced ketogenesis and its modulation by ageing. Nature 468(7327): 1100-1104 (2010).

Tolia A and De Strooper B. Structure and function of gamma-secretase. Semin Cell Dev Biol 20(2): 211-218 (2009).

Valenti L, Mendoza R M, Rametta R, Maggioni M, Kitajewski C, Shawber C J, and Pajvani U B. Hepatic notch signaling correlates with insulin resistance and nonalcoholic fatty liver disease. Diabetes 62(12): 4052-4062 (2013).

Yu D, Amano C, Fukuda T, Yamada T, Kuroda S, Tanizawa K, Kondo A, Ueda M, Yamada H, Tada H, and Seno M. The specific delivery of proteins to human liver cells by engineered bio-nanocapsules. FEBS Journal 272: 3651-3660 (2005).

What is claimed is:

1. A method of treating a subject afflicted with hypertriglyceridemia, comprising administering to the subject a gamma-secretase inhibitor in an amount effective to treat the hypertriglyceridemia in the subject.

2. The method of claim 1, wherein the administration reduces the subject's serum triglyceride level.

3. The method of claim 2, wherein the administration reduces the triglyceride level in the subject's very low-density lipoprotein (VLDL) serum fraction.

4. The method of claim 2, wherein the administration reduces the subject's serum triglyceride level and serum apolipoprotein C3(ApoC3) level.

5. The method of claim 1, wherein administration of the gamma-secretase inhibitor inhibits whole-body gamma-secretase.

6. The method of claim 1, wherein administration of the gamma-secretase inhibitor inhibits liver gamma-secretase more than inhibiting gamma-secretase elsewhere in the subject.

7. The method of claim 1, wherein the administration of the gamma-secretase inhibitor targets the gamma-secretase inhibitor to the liver.

8. The method of claim 1, wherein the administration of the gamma-secretase inhibitor targets the gamma-secretase inhibitor to hepatocytes.

9. The method of claim 6, wherein the gamma-secretase inhibitor is (i) coupled to a ligand molecule targeted to a receptor on a hepatic cell, or (ii) administered by a bionanocapsule.

10. The method of claim 6, wherein gastrointestinal Notch activity is substantially uninhibited.

11. The method of claim 1, wherein the gamma-secretase inhibitor is a small molecule inhibitor, an oligonucleotide capable of hybridizing to an RNA encoding a subunit of gamma secretase in a cell, or an adenoviral vector capable of expressing the oligonucleotide.

12. The method of claim 11, wherein the gamma-secretase inhibitor is an oligonucleotide.

13. The method of claim 12, wherein the oligonucleotide is an antisense oligonucleotide, an RNA-interference inducing compound, or a ribozyme.

14. The method of claim 12, wherein the oligonucleotide is targeted to hepatocytes.

15. The method of claim 12, wherein the oligonucleotide comprises 1, 2, 3, 4, or 5 or more stretches of nucleotides in a sequence that is complementary to nicastrin-encoding mRNA, presenilin 1-encoding mRNA and presenilin 2-encoding mRNA, or APH1A-encoding mRNA and APH1B-encoding mRNA, wherein each stretch of complementary contiguous nucleotides is at least 4, 5, 6, 7, 8, 9, 10, 11, 12, 13, 14, 15, 16, 17, 18, 19, 20, 21, 22, 23, 24, 25 or more nucleotides in length.

16. The method of claim 12, wherein the oligonucleotide is modified to increase its stability in vivo.

17. The method of claim 11, wherein the gamma-secretase inhibitor is a small molecule inhibitor.

18. The method of claim 17, wherein the small molecule inhibitor is 2,2-dimethyl-N—((S)-6-oxo-6,7-dihydro-5H-dibenzo[b,d]azepin-7-yl)-N'-(2,2,3,3,3-pentafluoro-propyl)-malonamide, (S)-2-((S)-5,7-difluoro-1,2,3,4-tetrahydronaphthalen-3-ylamino)-N-(1-(2-methyl-1-(neopentylamino)propan-2-yl)-1H-imidazol-4-yl) pentanamide, bis(fluoroalkyl)-1,4-benzodiazepinone, (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide, cis-3-[4-[(4-chlorophenyl)sulfonyl]-4-(2,5-difluorophenyl)cyclohexyl] propanoic acid, N-[N-(3,5-difluorophenacetyl)-1-alanyl]-S-phenylglycine t-butyl ester, bis(fluoroalkyl)-1,4-benzodiazepinone, or N-[(1S)-2-[[(7S)-6,7-dihydro-5-methyl-6-oxo-5H-dibenz[b,d]azepin-7-yl]amino]-1-methyl-2-oxoethyl]-3,5-difluoro-benzeneacetamide.

19. A method of reducing a subject's plasma glucose level, comprising administering to a subject in need thereof a gamma-secretase inhibitor in an amount effective to reduce the subject's glucose level.

* * * * *